United States Patent [19]
Ryan et al.

[11] Patent Number: 5,589,385
[45] Date of Patent: Dec. 31, 1996

[54] CLONING OF THE BIOSYNTHETIC PATHWAY FOR CHLORTETRACYCLINE AND TETRACYCLINE FORMATION AND COSMIDS USEFUL THEREIN

[75] Inventors: Michael J. Ryan, West Milford; Jason A. Lotvin, Union, both of N.J.; Nancy Strathy, Monsey, N.Y.; Susan E. Fantini, Ridgewood, N.J.

[73] Assignee: American Cyanamid Company, Wayne, N.J.

[21] Appl. No.: 125,468

[22] Filed: Sep. 22, 1993

Related U.S. Application Data

[63] Continuation-in-part of Ser. No. 821,109, Jan. 15, 1992, abandoned, and Ser. No. 821,419, Jan. 15, 1992, abandoned, which is a continuation of Ser. No. 558,039, Jul. 26, 1990, abandoned, said Ser. No. 821,109, is a continuation of Ser. No. 558,040, Jul. 26, 1990, abandoned.

[51] Int. Cl.$^6$ ............................ C12N 1/21; C12N 15/52; C12N 15/76
[52] U.S. Cl. .................. 435/258.35; 435/252.3; 435/252.31; 435/252.32; 435/252.33; 435/320.1; 536/23.223.7
[58] Field of Search .................. 435/252.3, 252.31, 435/252.32, 252.33, 252.35, 320.1; 536/23.2, 23.7

[56] References Cited

U.S. PATENT DOCUMENTS

| | | | |
|---|---|---|---|
| 4,892,819 | 1/1990 | Carr et al. | 435/69.1 |
| 4,935,340 | 6/1990 | Baltz et al. | 435/6 |
| 4,950,603 | 8/1990 | Ingolia et al. | 435/320.1 |
| 4,952,502 | 8/1990 | Epp et al. | 435/76 |
| 5,098,837 | 3/1992 | Beckmann et al. | 435/172.3 |
| 5,108,918 | 4/1992 | Groenen et al. | 435/172.3 |
| 5,149,638 | 9/1992 | Beckmann et al. | 435/76 |

FOREIGN PATENT DOCUMENTS

| | | | |
|---|---|---|---|
| 0346000 | 12/1989 | European Pat. Off. | C12N 15/00 |
| 0468217A2 | 1/1992 | European Pat. Off. | C12N 15/76 |

OTHER PUBLICATIONS

Binnie et al., Bacteriology 171(2): 887–895 (Feb. 1989).
Motamedi et al., Proc. Natl. Acad. Sci. USA 84:4445–4449 (Jul. 1987).
Fayerman, Biotechnology 4(9):786–789 (Sep. 1986).
Stanzak et al., Biotechnology, 4:229–232 (1986).
Reynes et al., J. General Microbiology, 134:585–598 (1988).
Butler et al., Mol. Gen. Genetics, 215:231–238 (1989).
Rao et al., Cosmid Shuttle Vectors for Cloning and Analysis of Streptomyces DNA, Methods in Enzymology, Academic Press, 1987, vol. 153, pp. 166–198.

Primary Examiner—Mindy Fleisher
Assistant Examiner—Philip W. Carter
Attorney, Agent, or Firm—Anne M. Rosenblum

[57] ABSTRACT

The present invention describes a purified and isolated nucleic acid molecule which encodes for the biosynthetic pathway of tetracycline, chlortetracycline or an analogue thereof. The invention relates to the isolation and cloning of the nucleic acid molecule in an isolated fragment from *Streptomyces aureofaciens* and the expression of the biosynthetic gene in a heterologous host such as *Streptomyces lividans*.

13 Claims, 16 Drawing Sheets

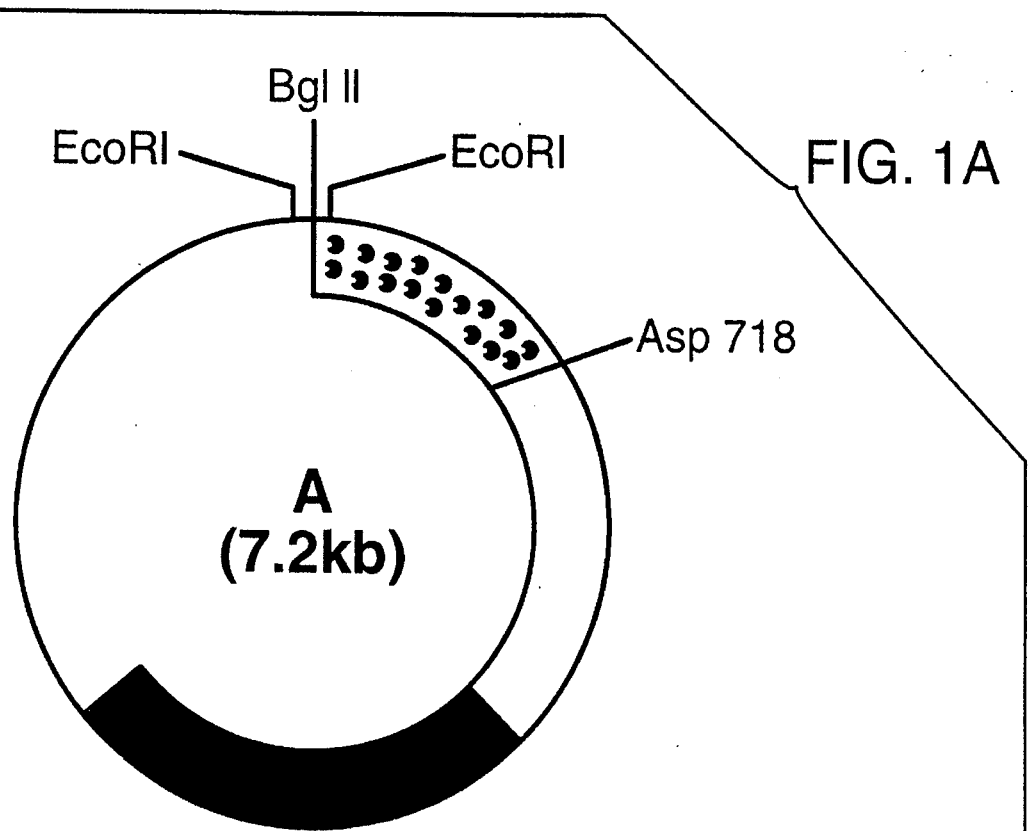
FIG. 1A
↓ Asp 718 DIGESTION
↓ TREATMENT WITH CIAP
↓ Bgl II DIGESTION
↓ AGAROSE GEL ELECTROPHORESIS
↓ ISOLATE 6.1kb FRAGMENT

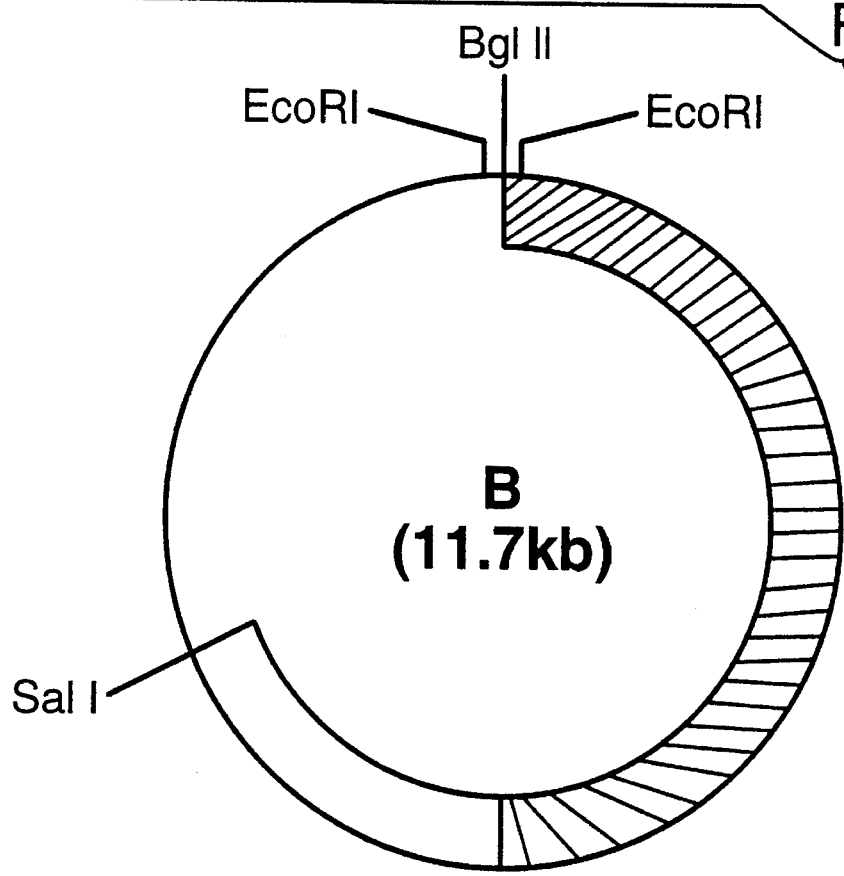
FIG. 1B
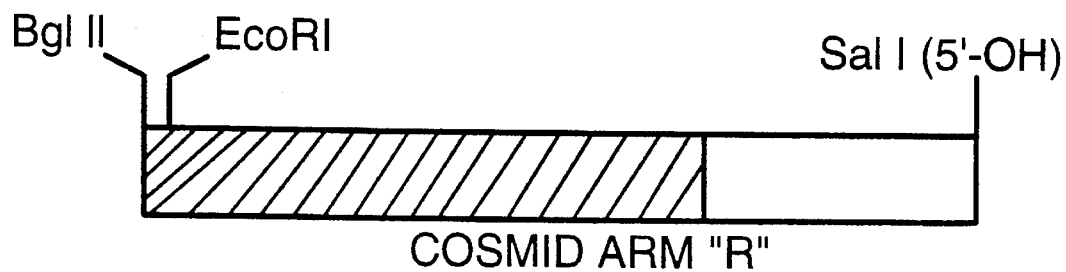

FIG. 4A

| | | | | | |
|---|---|---|---|---|---|
| GATCGGCCGA | CGGCTCCAGG | ACAGCCCGGG | CCGTCCCGGC | CCCCGCGGCA | 50 |
| CGGCCCACCC | CGCAGCGACC | CCGGCCCGGC | CGCTCCACGG | CCCGCTCCCG | 100 |
| GCCCGCACAC | CTTCCGGGCC | CCACTCCGAA | GAATCGGTTC | TCTTGGGCCC | 150 |
| GTCACCGGGC | CCGGGGCGTC | CACCGCACCG | CCCGCCGCGG | CCAGCCCGGA | 200 |
| TCGCTCCACT | CATCGGTCAC | TCGCGCCTGT | CGCCATCGGG | GGTCAACCGT | 250 |
| GTCAGTCGGC | AACAACCATC | CGTCGGTTCT | CGTCGTCGAG | GACAACGTCC | 300 |
| TGCTGCGCAC | GGGCCTGCAG | GCCCTGCTGT | CGGCCGAGCC | CGACCTCGTC | 350 |
| CTCCGCGCCG | CCGTCGGCGG | CGTGGACGAA | GCACTCGCCG | TCATGGCCGG | 400 |
| GCACCCCGTG | GACGTCGTGG | TGTACGGAGC | GGGCGAGTCG | GTGGCCGACA | 450 |
| CCGAGCGGGG | CCTCGAGCGC | CTGCTCGACC | GGGGCACCCG | GGTGGTCGTA | 500 |
| CTGAGCCGGC | GGGACCACCC | CGGCGAGATG | GAGACGTACC | TCAGCAGCGG | 550 |
| TGTGCACGCC | TACCTGGCAG | AGGACGCGGC | CGGGGAGTGC | CTCGGCTCGG | 600 |
| TGATCCGGGG | CCTGACCTCG | GACCGGGAGC | GGGTCTACAT | CATGGCCTCG | 650 |
| CGCTCCGGCC | TCGACTGGAT | GGCCGGCCAG | CGCGGCAACC | GCCTGTCCGG | 700 |
| ACGCGAGCGG | GAGGTCATGG | GCCTGGTCGC | GAACGGGCTG | AGCAACTCGG | 750 |
| CCATCGCGGG | CCGGCTCTGC | ATCTCGCCCG | GCACCGTCAA | GCGCCATCTC | 800 |
| CGGAACGTGT | TCGTCAAGCT | CAACGCCGTC | TCCCGGATCG | ACGCCGTGAA | 850 |
| CAAGGCCCGG | GCCGCTTCCA | TGCTGGTCCC | GGCCGGCCGG | GCCTGAGCCC | 900 |
| CGCGGACCGG | TCCGGCGCGG | ATCCGTCCGC | GGTGGACCGG | TCCGGCGCGG | 950 |
| ACCCCTGCGG | GGACGACGGC | CCGGCAGGGA | GCGGAGCAGG | GCTCGGCCGG | 1000 |
| GACGGGCCTC | AGGCCGAACG | GGCCCGCAGG | CCCTGCTCCA | TCGCCCGCGC | 1050 |
| GGCAAGCGCC | TGGAACTCCT | GCCGAGTGGG | CGACGTGCCG | CTGAGCAGGT | 1100 |
| CGTTGTGCAG | CTCCTGCAGC | GGTCGGGAGG | GGGCGATGCC | GAGGTCCTCG | 1150 |
| TCGAGCCGGC | GGTAGAGCAC | GCGGTAGACG | TGCAGGGCCT | CGCTCCGCCG | 1200 |
| CCCGGCGCGT | CCCAGGGCGA | GCATGAGCTG | CTCGTGGTAC | CACTCGTTCA | 1250 |
| TCGGCTGGTG | CAGGGTCAAC | AGTCTGAGTT | CGGGGATGAG | TTCCCGGTGG | 1300 |
| CGCCCGAGCT | GCCGGTCGGC | CAGGATGCGG | TGCTCCAGGG | CGCGCAGGCG | 1350 |
| CATCTCCTCC | AGGACGGCGA | CGTGACCGGC | GAGCGGAGCA | CCCCACCGGG | 1400 |
| ATGTCCGCCA | GGCGGTGCCC | CGCCACAGGT | CCAGCGCCTG | CCGCAGCCGC | 1450 |
| TGGGCGGCCG | CCTCGGGGTG | GCCGGCGGCC | AGCAGCCGGT | CCCCCTCGTG | 1500 |
| GTGCAGCCGC | TCGAACTCCT | GGGCGTCCAG | CTCCTCCTCC | CCCAGCAGCA | 1550 |
| GCACGTAGCC | GGGGGCCTTG | GTGAGGATGA | CCTCGCGGCC | CAGCGGACGG | 1600 |
| CAGAGCTTGC | GCAGTTGGTA | GATGTACGTC | TGCGCGGTGG | TGACCACCGT | 1650 |
| GCGTGGCGGG | CTGCTGCCCC | AGATCTCCTC | GATGATGAGG | CCGAGGTCCA | 1700 |
| CGATCCGGTT | CGCGTTCATG | AGCAGGACCG | CCAGCGTCCA | GCGGACCTTC | 1750 |
| AGCGCGCTCG | GGGTACACGG | AATTCCCTTG | TCGAGGACTT | CCAGCGGACC | 1800 |
| CAGAATGTTG | AACTTCACCA | TGCCTCCGAT | GTCGCTCGGA | TTCCCTCGGC | 1850 |
| CCCAGGTATA | TCCGGGTCCG | CGGACGGGTC | TCAAGAGGAA | TCCGCACAAG | 1900 |
| GTGGCAGGCG | CGCAATTCCA | AGGTGGCACC | GACGCATTTC | CAGAGCGGTC | 1950 |
| CGGCTCCCTG | TCCCGAGGGA | AACACCCCG | CCGACCGACC | CCGCCGATC | 2000 |
| GGCTGGCGGA | TCGACAAGTC | CTGTTAGGGT | GGGGGCGGTT | GGCCCCATGG | 2050 |
| GCCGGGCACC | AGTCACCTGA | TACCCGCGAG | ACAGAGCCAC | GAGGAGAAGG | 2100 |
| ACGTGCCCCC | GAAAGATCCG | TGTTGCTCCG | GTAATCCGTA | CGAAGACCGC | 2150 |
| AGAACTAGGG | GACACACGTC | TTGACAACCG | TGAACATCGG | AATCCTGGCC | 2200 |
| CATGTCGACG | CCGGTAAGAC | CAGCCTGACC | GAGCGACTGC | TGCACACCGC | 2250 |
| CGGCGTCATC | GACCGGGTCG | GCAGCGTCGA | CCGCGGCGAC | ACCCAGACCG | 2300 |
| ACTCGCACGA | ACTCGAGCGC | CAGCGCGGCA | TCACCATCCG | GTCCGCGGTG | 2350 |
| GTGTCCTTCA | CCGTGGGCGA | CGTCAAGGTC | AACCTCATCG | ACACCCCCGG | 2400 |
| CCACCCGGAC | TTCATCTCCG | AGGTGGAACG | GGCCCTCGGC | GTGCTCGACG | 2450 |
| GCGTGGTGCT | GGTCATCTCC | GCCGTGGAGG | GCGTACAGGC | CCAGACCCGG | 2500 |
| CTGCTGATGC | GCACGCTGGT | GAAACTGCGC | ATGCCGGTCA | TCCTCTTCGT | 2550 |

FIG. 4B

```
CAACAAGATC GACAGGATGG GCGCGCGCTA CCACGAGCTC CTGGACGAGA    2600
TCCGCTCCGA GCTCACCCCG GCCGTCGTCG CCCTGACCCG GGTCGAAGGG    2650
CCGGGCACCC CCGGAGCACG GGCGTTCGCC CGGACCGTCG GGACCGACGA    2700
CCCCGACTTC GCCGCCGAAC TGGCCGACGT CCTGGCCGAG CACGGCGACG    2750
ACTTCCTGGC CCGCTACCTC GAGGACGAGA CCTCCCTGAC CGCGCAGGAC    2800
TACAGCGCGG AACTCGCCCG CCAGGCGGCC CGGGCCCAGC TCTACCCGGT    2850
GCTCTTCGGC TCGGCCGTGG CCGGCGCCGG CATCGATGCC CTGGTCGACG    2900
GGATCACCAG GCTGTTTCCG GTCAATCACG GCGGCTCCGG GGGCACCCTC    2950
CGCGGTACCG TGTTCAAGAT CGAGCGCGGG TGGGCGGGCG AGAAGGTCGC    3000
CTACGTCCGG TTGCACGGGG GCGAGCTCGG GTCGCGGGAG AAGGTGTCCG    3050
TGTTCCGGCG CGACCAGCAC GGAGCCGTCA CCGAGATTCC CGGCCGCACC    3100
ACGGTGGTCG AGGTGTTCGA CCGGGCTCG GCCGTCGTCG AGTCGCGGGC    3150
CCGGGCCGGG GACATCGCCA AGGTCTGGGG GCTCAAGGGC ATCCGGATCG    3200
GCGACCGGCT CGGTTCGGCC GAGGGGCTGG ACGGGGAGCA CCTGTTCGCG    3250
CCGCCGAGCC TGGAGACCGT GATCCGACCC TCCCGGCCCA GCGCGATGCC    3300
CGAACTGTAC GACGCGCTGC TGCAGTTGGC CGACCAGCAC CCGTTCATCA    3350
ACGTCCGCAA GGACGACGAG GAGCAGGAGA TCGCCGTCTC GCTCTACGGT    3400
GAGGTGCAGA AGGAGGTCAT CGCGGCCACG CTCGCCGACG AGTTCAAGCT    3450
GGACGTGGCC TTCGAGGGCA CCCGGATCAT CTGTGTCGAG CGCCCGATCG    3500
GGGTCGGCGA GTCGGTGGAG GAGATCGACT ACCGGAGCAA GACCTTCTTC    3550
TGGGCCACGA TCGGCCTGCG GGTGGAACCC GGGGAGCCGG GATCAGGGGT    3600
CGTGTTCCGC CGCTCGGTGG AGCTCGGCTC GCTGCCGCAC GCATTCCACA    3650
AGGCCGTCGA GGAGGCCGTG CGGGCCACCC TGCAGCAGGG GCTGAACGGC    3700
TGGGAGGTGC TGGACATCCT GGTGACCCTC ACCCGTTCCG GGTTCGCCAG    3750
CCCGGTGAGC GCGGCGGGCG ACTTCCGCAA GCTCACGCCG CTCGTGCTGA    3800
TGAACGCGCT CAAGCAGGCG GGCACGCAGG TGTACGAACC GGTCAACCGC    3850
TTCGAGCTGG AGGTGCCGGG TGAGAACGCC AGCGCCGCCC TGCTGAGCCT    3900
GGTGGAGTGC GGCGCCACCC CGGAGAGCAC CCGGGGCCTG GCAGCAGCT    3950
GCCTGGTGGA GGGGACGATC CCGGCCCGCA CGGTGCAGGA GTTCGAGCAG    4000
CGGCTGCCGG GCCTGAGCCA GGGCCAGGGC GTGCTGGTCA CCCGGTTCCA    4050
CAGCTTCCAG CCGGTGGTCG GGGCGGCGCC GAGGCGGCGG CGGACCGACC    4100
TCAACCCGGT GGACCGCTCG GAGTACATGC TGCGGGCCTT CGGCGGGATC    4150
TGACGGGACG TCGCGAAAGT GAGGGCCCGA CCACCGTGAC GGTGGTCGGG    4200
CCCTCAGCCG TGGCGCACTC CGTCCTCAGT CGAGCAGTGC CACCGCTCGC    4250
GTCCAACCCG CCCCCGCCCC GGCGATCTTG ACCGGGAACG CCTGCACGGT    4300
GAACCCGGTC GGCGCGGGCA GTGCGCCCAG ATTGCTCAGA CGCTCGATCT    4350
GGCAGTACTC CCGCTGCCGC CGCGAAATGC GCGGGCCACA GCACGGAACG    4400
GTCGCGGGTG CGCTGGAACT CGGCGAGCAT GTGCGTGAAC GGAGCGTCCA    4450
GCCCGAAGCG TCCGTCCCGA TGAGCCGCAC GCCGAGGTCG AGCAGAAGGT    4500
TCGTCGCCGC CCCGTCCAGG CCCGCGAACC GGGTGAAGTA CTCGGGAGTC    4550
CCGGCGAGTC GTTCGGCACC GGTGTGCAGC AGCACGATCT CCCCGGCGCT    4600
CGGCCGGTGG TCGATCTCGT CGAAGGCGCG CCGCAGCCGG TCCACGCCGA    4650
CCGTCCCGAC CCCGCAGTCG GTGAGGTCCA GCCGGACGCC CGGCCCGATG    4700
AACCATTCCA GCGGCAACTC GTCGATGTGG CGCGGCACTC CGTAGGCGGC    4750
CCTGCTGCCG TAGTGGGAGG GTGCGTCGAC GTGCGTGCCG GTGTGGGTGG    4800
TCAGGGTCAG GGTGTCCAGC GAGAGCAGTT CCCCGTCCGG CAGGTCCGCG    4850
ACGTCGAACT CGAGGCCGTG GTCACGGAGC ATGCCCTCGG CCATGTGGCG    4900
CGCGCCGTCG GCCGGCGTCA GCACCTCGTG GCGGATGCCG TCCACCTCCC    4950
AGGCGTTGGC GTCGATCGTC GAGGAGAGGT CAATGAGGCG CATGCGCGGC    5000
TCCTTCCGGC AGCAGGGCGC AGTCCCGCAG GACGTCGAGG CAGCGCTCCG    5050
GCCCCCGATC CCGCGCGGCG AGGTGGCCGT CCGGCCGGAT CAGCAGGAAC    5100
```

FIG. 4C

| | | | | | |
|---|---|---|---|---|---|
| TCCCCTGGTG | CCAGGCCGAG | TTCGCGGCGC | AGAATACCCC | CGGGGTCGGG | 5150 |
| CAGCTCGCCC | GGGGCTCCGG | GGTCGGCGAC | GGTACGGACG | GAGACGGCGG | 5200 |
| AGCCGAACAG | CCGCTCCACC | CGGGCGAGCG | CCTCCCGGTG | CCCGGTGCTC | 5250 |
| CCGCCCTCGG | CCGGGGTGGC | GAGCAGGGTC | CAGCGGGGGT | CGGCGAGTTC | 5300 |
| GGCGCAGAGC | GCGGACCAGC | CGGGGTGCCC | GGCGGCCGTC | CGGGCGTCGC | 5350 |
| AGCCCACCCG | GTCCCGGGG | GAGGGCCGCC | CGGCGCGCGA | GCCGGCCGGG | 5400 |
| CGGGTGAGCG | GGCTGTCCGG | GTAGCCGAGG | GCCAGTCCGC | AGAAGCCCCG | 5450 |
| GATCATCCGG | CCCTCGACCT | TGCGCCGCAG | CGGCGTGATC | CGGCGCAGCG | 5500 |
| CCGCGGTGCC | CACGGTCAGC | AGGGCCGGGG | CCAGCGCGGT | GCGCAGCGAC | 5550 |
| ACCAGGGCGG | TGGCCGTGCG | GGTGGAGCGC | AGCAGCACGG | CCCCGGTCGG | 5600 |
| GACGCGCTCG | GCGTCGTAGC | TGTCCAGCAG | GGCGGGCCCG | GCGTGGCCGC | 5650 |
| GGATCACGTC | GGCGAGCTTC | CAGGCGAGGT | TGTAGGCGTC | CTGGATACCG | 5700 |
| CTGTTCATGC | CCTGCCCGGA | GGCCGGGCTG | TGGACGTGGG | CGGCATCCCC | 5750 |
| GGCGAGGAAG | CAGCGGCCCT | CGCGCATCCG | GGTGATCTGG | CGTTGCTGGA | 5800 |
| CGGTGAAGAC | GGAGAGCCAG | GTCGGGGTGC | CGACCTGACG | GGGCGCCCGA | 5850 |
| GCGCCCGGCC | CGATCTTGTC | GGCCAGGCGG | CGGCGGACCA | GCTCGCGGTC | 5900 |
| CTCGGCGCCG | TCGGTGTCCA | CCGTGTCCAC | CACGCGCCAC | TTGCCGGGCT | 5950 |
| CGGGGAACGG | GACGAGCAGC | AGGGTGCCGG | GCTCGGTGTG | CAGCAGGTGG | 6000 |
| TTGCTGTCCG | GCGGGAGGTC | GGCGTCGAGG | GTGACGTCGG | CGTTGAGCCA | 6050 |
| GACCTCGGTG | GAGTCGCCGA | TCAGGCGCAT | CCCGAGCTGC | TTGCGCACGG | 6100 |
| TGCTGCGGCC | GCCGTCGGCG | CCGACCAGCC | AGGGCACCCG | GGTCTCCTCG | 6150 |
| GTGCGCCCGT | CGGCGTGGCG | GAGGGTGACG | AGCACGGAGT | CGGGCCCGGG | 6200 |
| CTGCAGCGCG | GCGAGTTCGA | CGCCCATTC | CACGGGGACG | CCGAGTTCGG | 6250 |
| CGGTGCGCTC | GCGCAGCACC | TGCTCGGTGA | CCACCTGGTC | GACCATCAGG | 6300 |
| CTGAACGGGT | AACGGGTCGG | CAGTGAGCGG | TAGTTGGTGT | CGAAGCGGAT | 6350 |
| GAGGGTGCGG | CCCCGGCGGT | GCATGGTGAA | GTGGGTGACC | CGCCGGCCGA | 6400 |
| GCGGCAGCAG | CCGGTCGAGG | GCGCCCATCT | GCTCGAGCAC | CTCCATGGTC | 6450 |
| CGGGCGTGCA | CCGCCAGGGC | CCGGCTGCTG | GTGGCCGGGG | CCGGGCGCGG | 6500 |
| CGTCGACCAG | CCGGACGGGA | ACGCCCCGCG | CCTGGCGAGT | TCGTGGGCCG | 6550 |
| CGGTGAGGCC | GACCGGGCCG | GCCCCGCGA | TCAGGACGGC | CGGAGCGGGG | 6600 |
| TCAGCCACGG | CGTTCCTCGG | CGAAGCGCTT | GGCCAGGCCG | AGCGTGGCGC | 6650 |
| GGCTGTTGCC | GCCGGCGGCC | TCGCGGATGA | AGCGGCGGGC | GGTGGCGGCG | 6700 |
| GTGGCGTCCG | GGCCGAGGAC | GGTGGGGACC | GCCTCGGGGT | TGAGGACGAC | 6750 |
| GGCGTGCCAG | GAGGTGACCC | GCACTCCGCG | GTCGGTCGAC | TCGACGGTCC | 6800 |
| AACGGCCGGT | GTGGGCGGCC | ATCATGGAGG | GGGTGCGCAG | CTGCTTGTAG | 6850 |
| GCGATGCCGG | ACTCCGGGAA | GCAGATCCGG | ATGGACTCGG | TGGTGTGTTC | 6900 |
| GGAGCCGTCG | GCGGTGCGGG | TGTCCATGGA | CATGTGCTGG | ATGCCGCCGG | 6950 |
| CCTCCTCGCG | CAGGTCGAGG | CGGGCGACGT | GGGGCAGCCG | GCGGGCCAG | 7000 |
| GCGGCGGCGT | CCCGCAGGAA | GTCGTAGACG | GCCTCCGGGG | CGGCGTCGAC | 7050 |
| CAGCACCGAG | TCCTCGAACT | CGAACTCGAA | CTCGGCGAGC | CGGTTCCAGC | 7100 |
| GTTCGGCGAG | GTCCTTGATG | CCGGCGAGCT | CGCTGCGGCT | GTTGCGGTCC | 7150 |
| GTCGCCTCGC | TGATCCAGCG | CAGGCCCTGC | GGGTCGTCGT | CGAGCGCGCT | 7200 |
| GAACTCGTGG | GTGAGGGTGA | GGGTGGTGCC | GCCGGGCGC | TCGGCGACCT | 7250 |
| GCCACTCCCC | CGCCATCGAG | GCGACCGGGG | CCGAGGAGGC | CTCCTGGCGG | 7300 |
| AAGCGGATCC | GGCGCAGGTC | GGCGTCCAGG | TCTCGGCGGG | ACGTCCAGTG | 7350 |
| CTTGACCTCG | CCGTTGGCCC | GGGCCCAGAT | CCGCAGGCGC | TCGGCGCCCG | 7400 |
| GCCCCAGCTC | CTCGCGCTCG | ACGTGGAGGG | TGGGGCGAA | GCGCCGCGGC | 7450 |
| CAGGCCAGGG | CGTCGGCGAT | GACGGTGTAG | ACGACCTCGG | CGGGGGCGTC | 7500 |
| GACGTCGATC | GAGTGGGTGG | TGTGCTGGAT | GGTGCTCATG | GGTGGGACCG | 7550 |
| GCCCTTTCCG | TCGGCGGGGT | GAAGTTCGGC | GGGGTGCGTG | GGGTGCGGCT | 7600 |
| CAGTAGATGC | CGAGGCCACC | GCAGACGTTG | ATCGCCTGCG | CGGTGACCGA | 7650 |

FIG. 4D

```
CGCGGCGTCG GGGGTGGTCA GGTAGTCGAC CATGCCGGCG ACCTCCTCCG    7700
CGGTGGAGTA GCGGCCGAGC GGGATCTTCT GCTCGAAGCG CGAGAGCACG    7750
TCCTCCTCGG TGGTCGCCCA GGTCGCGGCG TACGCCTGGC GGACCCGCAC    7800
GGCCATCGGC GTCTCGACGT AGCCGGGGCA GACGGCGTTG ACCGTGGTGC    7850
CGGTGTGGGC GAGTTCCTTG GCCAGCGCCT TGGTGAAGCC GATGACGCCG    7900
GCCTTGGAGG CCGAGTAGGG GGCGCCCAGC GGGACACCCT GCTTGCCGCC    7950
GGTGGAGGCG ACGCTGATGA TCCGCCCGTG CCCGGCCGCC TCCATGCCGC    8000
CGGTGGTGAG GACCTCGCGG GTGACGCGGA AGACGCTGGT GAGGTTGGTG    8050
TCGATCACGT CCTGCCACAG CTCGTCGGTG AGGGTGGAGG TGACGCCACC    8100
GCCGTTGCGT CCGGCGTTGT TGACCAGCAC GCCGATCGCG CCGAAGCGGT    8150
CCACCGCCGC CCGGACGAGC CTGCTCACGT CCGGCGCGGA GCGGACGTCG    8200
GCCGCGAGGC CGTCCACCTC CAGGCCCTCG CCGCGCAGGC GGGCGACCGT    8250
CTCGGCGACG CCCTGCGCGG TGCGGGCGCA GATGAAGACG CTCAGCCCGC    8300
GCCGGGCCAG CCGCTCGGCG CTGGCCAGTC CGATGCCGCT GGTCGCCCCG    8350
GTCACCAGGG CGACGTCGCC GGTCGTCACG GTGCTCATCG CATCGATCTC    8400
CTGTCTCGCT CACGGATCGC GGGCCCGGCG GGCCCGCCGG TCGGGCCCG    8450
CCCCCGCGCC CCGTCGGGAA CCCGGGGGGA CAGGCCCCGG GCCGACCCTG    8500
CCCGGACGGC TTCGACTGCG GTTCGAGCGC GCCGCACACG CCGACCGCTC    8550
CAACGGGATT CGAAGCGCGG GTGGGAGCGT CGGCGCTGCC CAACCACCGA    8600
CGCAACGAGG AGGCCCGGAG CATGACCGGT TCGCTCTACG AGGAGGTCCA    8650
GCACTTCTAC GGGCGGCAGA TGCGCCACCT GGACGAGGGT GAGGTCACCG    8700
AGTGGGCCGC GACCTTCACC GAGGACGGCG TGTTCGCCGC CAACGCCCGC    8750
CCGCACCCGC AGGAGGGGCG CGCGGCGATC GAGCAGGGCG CCCGGGAAGC    8800
CGCGCAGCGC CTGGCCGATG CCGGAATCCG GCACCGGCAC TGGCTGGGGA    8850
TGCTGGAGGT CGCCGCGCAG CCGGACGGCC TGGTGCTCGC CAAGACCTAC    8900
GCGCTGATCG TCGCGACGCC CAAGGGCGGG CCGGCCGCCG TGCACCTGAG    8950
CTGCAGCTGT GAGGACCAGC TGGTGCGCGT CGACGGCGAG TTGAAGGTCC    9000
GGCACCGCCG GGTGCACCGG GACGACCTGC CCGCCTGAGA GGAGGCCACC    9050
GTGGACCTCC CACGGGACAG TACGACCTTC GGTCCGCCGC TGGACGTGGT    9100
GGCGGAGCTG ATCGGCGGGC CCCGGATCGA CGACCTCGTC CGTCGCGCGG    9150
CTGAGCTGAC GCCTCGTCAT GTAGCTCTGG TGCACGGTGA CCTGGTGCTC    9200
GACCACGCCG CGCTGGAGGC CCGGGTGAGC GACTGCGCCG AGGCGCTGCG    9250
CGCCGCGTTC GGCGGTCCCG GCACGGTCAT CGCGATCGCC GCCGAACTGA    9300
CCGTCGACTT CGCCGTCACC TTCCTGGGCA TCTCCCGCTC CGGGAACACC    9350
AGCGCCATGT TCAACCCGCT CGTCCCGGAC GACACCCTGG TGCACGTCCT    9400
GAACTCCTGC GGCGCCCGGG CGGCCGTGCT GTCGCCCCGG ATGCACCGCC    9450
GTGTCCTGGC CCTGCGGGAC CGGCTGCCGC TGCTGCGGCA ACTGGTGGTG    9500
ACCGCCGACG CGCTCGACGG CACGCCCGTC CTGGACGCCC TGGAGCGCAC    9550
CGCCGTCCCG GCCGGCGAGG TGGTGGAGAC CGCCTGCCTG CAGTTCACCA    9600
GCGGCACCAC CGGCGCGCCG AAGACCGTCC GGCTCAGCCA CCGCAACCTG    9650
CTGGTGAACG CGGCGCAGTC GGCGCACGCC CACCGGCTGA CGGCCGACGC    9700
CGTCTCGCTC AACAACCTGC CCTCCTTCCA CCTGATGCAC CTGAACACCG    9750
CGCTCGCGGT CGGCGCGACG CACGTGCTCT GCCCGGAGGA GGACCGCGCG    9800
GCGCTGGTGG GACTGGCCCG TACCTGGCGG GCCTCGCACC TGTACAGCCT    9850
GCCGGTGCGG TTGTCCCGGC TCGCCGGGGA CGAGCGGCTG CCCGGCTTCC    9900
GCATCCCCTC GCTACGGGCG GTGCTGTCCG GTGGATCGGC GCTGCCGCCC    9950
CGGACGACGA CCGCCCTGCA GGAGCACTTC GGGGTGCCGG TCGTCCAGGG    10000
CTACGGCCTC GCCGAGACGT CCCCGTCGAC GCACTTCGAC CTGCCCGAGG    10050
GGCCCACCCT CGGCTCCAGT GGGCCCCGG TCGCCGGGAC GGCCTGCCGG    10100
ATCGTGGACG TGCGCACCGG CGCGGTGCTG CCGGTGGGCG AGCGCGGTGA    10150
GATCCAGGTC CGGGGCCCGC AGTTGATGCT GGGCTACCTG GGCGACGGGC    10200
```

FIG. 4E

| | | | | | |
|---|---|---|---|---|---|
|CCACCGACGC|CGTCGACGCG|GACGGCTGGT|TCCGCACCGG|TGACGTCGGC|10250|
|CGGATCGACG|AGGCCGGCCG|CCTGTTCGTC|GTCGACCGGA|TCAAGGACGT|10300|
|CTTCAAGTGC|GACAACTGGC|TGGTGTCGCC|GACCGAGATC|GAGCGGGTGC|10350|
|TGATGCGGCA|CCCGGCCGTC|GCCGACTGTG|TGGTCTTCGA|CCAGCCCGAC|10400|
|GAGCTGAGCG|GCGCCGTCGC|CGTCGGCCTC|GTCGTGCCGC|GCGGCGAGGG|10450|
|CGTCGACCCG|GCCGCCCTGG|CCGCGTTCGC|GAACGCCCGG|CTCCCCTACT|10500|
|ACGAGCACCT|GAAGCAGCTG|CGCCTGGTGG|AGGGCATCCC|GCGCTCCGCC|10550|
|ACGGGCAAGG|TCCAGCGGCG|CGAGCTCCGT|GACCGGCTGT|TCGGCTCCCT|10600|
|CTGACCCGCA|CCACCCCACC|CGTCCGACCC|ACCACAGGAG|GAACACCGTG|10650|
|TACACCTTCA|TCAACCGTTT|CACCGTCACC|GGGGACGTCG|CCGAGTTCGA|10700|
|GACGCTCGTC|GGCGAGATCA|GCGAGTTCAT|GAGCGGCCGG|CCCGGCTTCC|10750|
|GCTCGCACCG|GCTGTACCGC|TGCGCCACGG|ACGCCTCGGT|GTACGTGGAG|10800|
|ACCGCCGAGT|GGGACGACGC|GGCCTCGCAC|CGGGCGGCGA|CCGGCTCGCC|10850|
|GGAGTTCCGC|GCCCGGGTCG|GCAAGGTGAT|GAGCCTGGCC|AAGGCCGAGC|10900|
|CGGCCCCGTT|CGACCTGCTC|GCGCAGCACG|GCGCCTGAGA|GGGGGAGCAC|10950|
|CATGACGGAC|AACGGCAGAG|TCATTGCGCA|GCCGGTGATC|CAGCTGCGCG|11000|
|AGCTGGGGCT|GGCGGCGGCC|GGCGCCGCCG|CCGTGCGGGC|CGCGGCCCGG|11050|
|CTGGGCCTGG|CTGACGCCCT|GGGCGAGGAG|CCCGCCGGCG|CGGCCGAGCT|11100|
|GGCCCGGGCC|GTGAACGCGG|ACCCGGACAC|CCTGCAGCGG|CTGCTGCGCG|11150|
|CCCTGGCCTG|CTACGGCGTG|TTCGCCGAGC|AGCCGGACGG|TCGGTACGTG|11200|
|CACACCGGCG|CCTCCCGGCT|GCTGCGCGAG|GACACCCCGC|GCAGCCTGAA|11250|
|GGACATGGTG|CTCTGGGGCA|CCGAGCCGTG|GACCTGGGAG|CTGTGGGGCC|11300|
|ACCTCGACGA|GGCGGTGCGC|ACCGGCAAGG|CCGTCTTCCC|CGAGCTGCAC|11350|
|GGCATGGACT|TCTTCGACCA|CCTGCACGCC|CACTCCCCCG|AGTCGGCGGC|11400|
|CGTGTTCGAC|CGGGCGATGA|CCCAGTCCAG|CCGGCTCTCC|GCGCTCGCGT|11450|
|TGGCCGACCG|GCTGGACCTC|GGCGGGGTCG|GCACGGTGGT|GGACATCGCC|11500|
|GGTGGCCAGG|GGCACGTGCT|GGCCACCCTG|CTGGAGCGCA|ACCCCGGTCT|11550|
|GCGCGGCACC|CTGCTGGACC|TGCCCGAGGT|CGTCTCCGGG|GCCGACGCCC|11600|
|GGCTGCGGCC|GGGCGGTGCG|CTGGCCGGGC|GCGCCACGCT|GCTCGGCGGC|11650|
|GACTGCCGGC|GGGAGATCCC|GGTGCAGGCC|GACGTCTACC|TGCTGAAGAA|11700|
|CATCCTGGAG|TGGGACGACG|AGAGCACCGT|CCTGACGCTG|CGCAACGTCG|11750|
|TCCGGGCGGC|TGCTCCGGGC|AGCCGGGTGA|TCGTGGTCGA|GAACCTGGTG|11800|
|GACGGCAGCC|CCGAGCTGCG|GTTCACCACG|GCGATGGACC|TCCTGCTGCT|11850|
|GCTCAACGTC|GGCGGCCGCA|AGCACACCAG|GGCCGGCCTG|GTCTCGCTGA|11900|
|TCGAGGAGGC|GGGCCTGACC|CGGGCCGAGG|TCCGTCCGGT|CAACTCCTAC|11950|
|CTGCACCTGG|TGGAGAGCGT|GGTGCCCGAA|CGGGGCTGAC|CCGCCCGCCC|12000|
|ACGGCCGCCG|CCCCCGGACC|CGTCCGGGGG|CGGCGGCCGT|GCTGGTCCGG|12050|
|GGGCGGCGGC|CCTCGCACTG|TCCGGGGGCG|GCGGTGAGCC|CTCGGCACGG|12100|
|CCGACGGGGC|TCGGGGGGGC|GGAACGGGAA|GGGGAGCGGG|GTCAGATGCC|12150|
|CTCGGCGAGC|CGCTTCACCG|CCTGCTCGAC|CCGCTCGTCG|GTCTCGGTGA|12200|
|CGGCCACCCG|CACGTGCCGG|GCGGCCGCAG|CGCCGTAGAA|CTCACCGGGC|12250|
|GCCACCAGGA|TGCCGCGGTC|GGCCAGCGCA|CCGACGGTCG|TCCAGCACGG|12300|
|CTCGTCCCTG|GTCGCCCAGA|GGAACAGCGC|ACCGGCCGAG|TGCTCGATCC|12350|
|GGAAGCCGGC|GTCCACCAGC|GCCCCGCGCA|GCAGCTCGCG|CCGCCGGGCG|12400|
|TAGCGCTGGC|GCTGGGCCGC|CAGGTGCGCG|TCGTCACCGA|GCGCGGCGAC|12450|
|CATGGCGGCC|TGCACCGGGG|CGGGGACCAT|GTGGCCGGCG|TGCTTGCGCA|12500|
|CCTCCAGCAG|CGTCGCGATG|ACGGCCGGGT|CGCCGGCGGC|GAAGCCCGCC|12550|
|CGGTAGCCGG|CCAGGTTGAA|GCGCTTGGAC|AGCGAGTGCA|CCGCCAGTAC|12600|
|GCCGTGGTGG|TCGCCGCCGG|TGACCTCGGC|GTGGAGCACC|GAGCGGGTCG|12650|
|AGCGCTCCCA|CACGTGGTCC|AGGTAGCACT|CGTCGTTGAC|CACCAGGGTG|12700|
|CCGCGCTCGC|GCGCCCACTC|GACGACCGCG|CGCAGTTCGG|CGGCGTCGAG|12750|

FIG. 4F

```
CACCCGGCCC TCCGGGTTGG ACGGGGAGTT CAGCCACAGC AGGCGCGGCG    12800
CGGGGCCGTC GTAGCTCAGC GGGTCGTCCG TCCGGACGAA GGTGGCACCG    12850
GCCAGTCGAG CGCTCACCTC GTAGGTGGGG AAGGACAGTT GGGGGGCAAG    12900
GACGACGTCC CCCGGGCCCA GGCCCAGCAT GGTGGGCAGC CAGGCGATCA    12950
GCTCCTTGGT GCCGACCGCC GGGATCACGG CCTCCGGCTC GACGCTCACG    13000
CCCTCGCGGC GCAGCAGCCA GGCCGCGGCG GCGGCCCGCA GCGCGGGCGT    13050
GCCCTCGGTG GACGGGTAGC CCGGGGCGTC GGCCGCGGCG GCCAGGGCCG    13100
CGCGCACGGC CTCCGGGGTC GGGTCGACCG GGTCACCGAG CGCCAGGTTG    13150
ACCAACCCGT CGGGGTGGGC GGCCGCGCGC CTGCGGTACG GAACAGAAC     13200
GTCCCAGGGG AACTTCGGCA GCCGCTCGAT CATGCCTGCG CCCCCGCCCC    13250
GACGTTGCGG GCCAGCGGCG GAGCCTGGCA GTCGGAGTCG ATGCCCCAGG    13300
AGACGATCCG CTCCGGCGTG ATCCGGATCA GCTCGTCGTC GACGTGCGGC    13350
AGGATCTCCT TGCCGCCGGT CGCCAGCGCG ACGGCGGTGC CCCGGATCTC    13400
GATCCCGCGG ACGACCCAGC GCTGCGCGTC CACGATGTCG TCCACCACCA    13450
GCGACACCCG CGGATGCCCC TGCACGTGGC GGTACTTGAG GCTGCGGGCC    13500
ATGCCGCGCC CGGTCACGTC GACGGTGCCG AGCTCGGCGT TGTAGTGGAA    13550
GCCCAGCGGG ACGACGTGCG GCTGTCCCCG GCCGTCCACG GTGGCCAGGC    13600
GGGCGAGCGG CTGCGAGGCC AGGTAGGCGG CCTCTTTCGC GGTGAATGGC    13650
ATGGCTGTCC TCGGTGTCTG CGGGTCAGGG TCGGCGCCCA CGCTAGGCAG    13700
CCTGCTTCGA GCGGCCTTGG TGCCGTTCGG CCTGCTCGCG TACCCGCGCT    13750
GGACTCCGGC TCGAAGTCCG GCTGACACGG TGAGGCCGTC GTACCGGACC    13800
GAGACGGGAG GTCGCGTTGG ACTGCGATGT GGTGGTGGCG GGAGCGGGGC    13850
CGACGGGCCT GATGCTCGCC TGCGAACTGG CCCTGGGCGG AGCCCGGGCG    13900
GTGGTGGTGG AACGGCGCCG CGAGCCGGAG AAGCACTCCA AGGCCATGGG    13950
CATGCAGGGC CGCACCGTGG AACTGCTCGA ACTGCGCGGG CTGCTCGACC    14000
GCTTCAAGGA GGGCGCGGGC GTGCTGCAGG GCGGCAACTT CGCCAGCCTG    14050
GGCGTGCCGA TGCGCTTCGA GGAGTTCGAC ACCCGCCACC CGTACGTGCT    14100
GCTGGTGCCC CAACTGCGCA CCGAGGAGCT GCTCGCCGAA CGGGCCCGCG    14150
AACTGGGCGT GCGGATCGTG CGCGGCTCGG GCGTCACCGG CTTCGCCCAG    14200
GACGCCGACG GGGTCACCGT CGAGACGGAC ACGGGCCTGC TTCGGGCACG    14250
GTACCTGGTC GGCTGCGACG GCGGCGGCAG CACCGTCCGC AAGGCCGCCG    14300
GCATCGGCTT CACCGGACAG GACCCGCACA TGTACGCCCT CATCGGCGAC    14350
ATGCGCTTCA GCGGCGACCT GCCGCGCGGC GAGGGCCTCG GCCCAATGCG    14400
GCCGGTGGGC CTGGTCAACC CCGCCAAGCG GTCCTGGTTC GGCGCCTTCC    14450
AGCACCAGCC GGGCGTCTAC CGGGCCACCG TCGCCTGGTT CGACCGGCCC    14500
TTCGCCGACC GCCGCGCCCC GGTCACCGAG GAGGAGATGC GCGCCGCACT    14550
GGTCGAGCAC ACCGGCAGTG ACCACGGGAT GCACGACGTC ACCTGGCTGT    14600
CCCGCCTCAC CGACGTCTCC CGGCTGGCCG ACTCCTACCG GCTGGGCCGG    14650
GTGCTGCTGG CCGGCGACGC CGCGCACATC CACCTGCCGG CCGGCGGCCA    14700
GGGGCTCAAC CTGGGCTTCC AGGACGCCGT CAACCTCGGC TGGAAGCTGG    14750
CCGCCGTGGT CCGCGGCCAC GGCACCGAGG AGCTGCTGGA CAGCTACGGC    14800
CGCGAGCTGT CGCCCGATCG CCGACGGGTG GTGCGCAACA CCCGCACCCA    14850
GGCCGTCCTG ATCGACCCGG ACCGCGGTA CGAGGCACTG CGCCAGACCT     14900
TCCGCGACCT GATGGCGCTG CCCGACACCA ACCGCCACAT CGCCGGCATG    14950
CTCTCCGGCT TCGACGTCGC CTACGGCGGC GGCGACCACC CTCTGGTCGG    15000
CCGCCGGATG CCGGACGCCG AGCTGATCAC CGCGGACGGG CCGCGGAGGA    15050
TCAGCGATTG CTTCGCCGGG GCCCGCGGTC TGCTGCTGCT CCCCGAACAG    15100
GGCCCGACCG CCTCGCCGCT GGCCGCCTGG GCGGACCGCG TGGACACCCT    15150
GACCGTCAAG TCGGGCGGCC CGGACCCGGA CACCGCCCAC CTCGTCCGCC    15200
CGGACGGCTA CGTGGCCTGG GCCGGCGAAC CGGCCCGCAC CGAGGAACTG    15250
CACCACGCCG CGACCACCTG GTTCGGCGCG GCGGCCTGAT CCCCCTCCCC    15300
```

FIG. 4G

| | | | | | |
|---|---|---|---|---|---|
| CTGAGAAAGG | ACGCACGATG | ACCTCGTCCA | CCGACAGCGC | CGCCGCCCGC | 15350 |
| GCGCGCCGGA | TCGTCGCCCT | CAACACCGCC | TACTTCCAGG | CGAAGGCGCT | 15400 |
| GCAGAGCGCG | GTCGAGCTCG | GCCTCTTCGA | GCTGCTCGCC | GAGCGCTCCG | 15450 |
| CCGGGCTCGA | CCAGATCCGC | GCCGAACTGG | GCGTCCGGCA | CCGGCTGTTC | 15500 |
| AAGGACTTCC | TGAACGCCCT | GGTCGGCCTC | GGCCTGCTGG | ACGAGCAGGA | 15550 |
| CGGCGGCTAC | CGGGCCTCCG | AGCTCGCCCG | GGAGTTCCTG | CTCCCCGGCC | 15600 |
| CCACGTACCT | CGGCGGCACC | GCCCGCCAGC | ACGCTCGGCT | GCACTACCAC | 15650 |
| GCCTGGGCGC | AGCTGACCGA | CGCGCTGCGC | GACGGCAAGG | CCAAGTCGGC | 15700 |
| CGTGGCCGCG | CAGGGCCAGC | TGGCCTACCC | CAAGCAGTAC | GAGGACCTGG | 15750 |
| ACCGCGCCCG | GCAGATCATG | CTGCACATGG | ACGCCCACAA | CGGTTTCACG | 15800 |
| GCCGACGAGT | TGGCGCGCGC | GATCGACTGG | AGCCGGTACA | CCTCCTTCGT | 15850 |
| GGACGTCGGC | GGCGGGCGCG | GCAACGTCGC | CTCCCGGATC | GTCACCGCCC | 15900 |
| ACCCGCACCT | GCGCGGCGGG | GTCTTCGACC | TGCCGGCGCT | GCGCCCGCTC | 15950 |
| TTCGAGGAGC | TGGTGGCCTC | GGCCGGAACC | GCCGACCGGG | TGGACTTCCA | 16000 |
| CGGCGGTGAC | TTCTTCGCCA | CCGACCTGCC | GGAGGCGGAC | GTGGTGATCT | 16050 |
| TCGGTCACGC | CTGCCGGACT | GGGCCGGTCG | GGGACCGCAG | GGAGCTGCTG | 16100 |
| CGCCGCGCCC | ACAAGGCGGT | GCGCCCGGGC | GGCCTGGTGG | TGCTGTACGA | 16150 |
| CGCCATGATC | GACCCGGAGG | AGCGCGACCC | CGAGGTCCTG | CTGCAGCGGA | 16200 |
| TCAACCACAC | CATGATCCGG | GACGAGGCCG | GGCCTACTC | GCTGCAGGAG | 16250 |
| GCCCGCGCCT | ACCTGGAGGA | GGCCGGCTTC | ACCGTCGACC | GGATCGCCGC | 16300 |
| CTCCGACACC | ATCACCCGCG | ACCACTTCGC | CATCGGCGTC | AAGTCGGTCT | 16350 |
| GAAGGAAAAG | GAGTTCGACA | TGACCGACAC | AACCGCGGAT | CAGACGCGGC | 16400 |
| ACGGCGACCG | GCCGTACGAC | GTCGTCATCA | TCGGCAGCGG | GCTGTCGGGC | 16450 |
| ACCATGCTCG | GCTCGATCCT | CGCCAAGCAC | GGCTTCCGGA | TCATGCTGCT | 16500 |
| GGACGGTGCC | CACCACCCCC | GCTTCGCCGT | CGGCGAGTCC | ACCATCGGGC | 16550 |
| AGACGCTGGT | GGTGCTGCGG | CTGATCTCGG | ACCGGTACGG | GGTGCCGGAG | 16600 |
| ATCGCCAACC | TGGCGAGCTT | CCAGGACGTC | CTCGCCAACG | TCAGCAGTTC | 16650 |
| GCACGGGCAG | AAGAGCAACT | TCGGCTTCAT | GTTCCACCGG | ACGGCGAGG | 16700 |
| AGCCGGACCC | GAACGAGACC | AGCCAGTTCC | GCATCCCCTC | GATCGTCGGC | 16750 |
| AACGCGGCCC | ACTTCTTCCG | CCAGGACACC | GACTCCTACA | TGTTCCACGC | 16800 |
| CGCGGTGCGC | TACGGCTGCG | ACGCCCGGCA | GTACTACCGG | GTGGAGAACA | 16850 |
| TCGAGTTCGA | CGACGGCGGG | GTGACCGTCT | CCGGCGCGGA | CGGCAGCACC | 16900 |
| GTCCGGGCCC | GCTACCTGGT | CGACGCCAGC | GGCTTCCGCT | CGCCGCTGGC | 16950 |
| ACGGCAGTTG | GGGCTGCGGG | AGGAGCCGAG | CCGGCTCAAG | CACCACGCCC | 17000 |
| GCTCGATCTT | CACCCACATG | GTCGGAGTGG | ACGCGATCGA | CGACCACGTG | 17050 |
| GACACGCCGG | CCGAGCTTCG | CCCGCCGGTG | CCGTGGAACG | ACGGGACGAT | 17100 |
| GCACCACATC | TTCGAGCGCG | GCTGGATGTG | GATCATCCCG | TTCAACAACC | 17150 |
| ACCCCGGGGC | CACCAACCCG | CTGTGCAGCG | TCGGCATCCA | GCTCGACGAG | 17200 |
| CGCCGCTACC | CCGCCCGGCC | GGACCTGACG | CCCGAGGAGG | AGTTCTGGTC | 17250 |
| CCACGTGGAC | CGCTTCCCGG | CGGTGCAGCG | GCAGTTGAAG | GGCGCCCGCA | 17300 |
| GCGTGCGCGA | GTGGGTGCGA | ACGGACCGCA | TGCAGTACTC | CTCGAGCCGG | 17350 |
| ACGGTCGGCG | AGCGCTGGTG | CCTGATGTCG | CACGCGGCCG | GCTTCATCGA | 17400 |
| CCCGCTCTTC | TCCCGCGGCC | TGTCCAACAC | CTGCGAGATC | ATCAACGCGC | 17450 |
| TGTCCTGGCG | GCTGATGGCC | GCGCTGCGCG | AGGACGACTT | CGCGGTCGAG | 17500 |
| CGCTTCGCCT | ACGTGGAGGA | ACTGGAGCAG | GGCCTGCTGG | ACTGGAACGA | 17550 |
| CAAGCTGGTC | AACAACTCCT | TCATCTCCTT | CTCGCACTAC | CCGCTGTGGA | 17600 |
| ACTCGGTCTT | CCGGATCTGG | GCCTCGGCCA | GCGTGATCGG | CGGCAAGCGC | 17650 |
| ATCCTCAACG | CACTGACCAG | GACCAAGGAG | ACCGGCGACG | ACAGCCACTG | 17700 |
| CCAGGCGCTG | GACGACAACC | CGTACCCGGG | CCTGTGGTGT | CCGCTGGACT | 17750 |
| TCTACAAGGA | GGCCTTCGAC | GAGCTCACCG | AGCTGTGCGA | GGCCGTGGAC | 17800 |
| GCCGGGGACA | CCACGGCCGA | GGAGGCCGCG | CGGGTGCTGG | AGCAGCGGGT | 17850 |

FIG. 4H

```
CCGCGAGTCG GACTGGATGC TGCCGGCCCT GGGCTTCAAC GACCCCGACA    17900
CCCACCACAT CAACCCGACG GCGGACAAGA TGATCCGGAT CGCGGAGTGG    17950
GCCACCGGTC ACCACCGCCC GGAGATCCGT GAGCTGCTGG CCGCCAGCGC    18000
CGAGGAGGTC AGGGCGGCGA TGCGGGTCAA GCCGTAACAC GAGGGGCAAC    18050
GGGCAGCAGC GTCCGCGGGA CGGCTGCTCC CGGACGCGGG CCTCGCCGTT    18100
CGCCGCACGC GGGCGGGCTC AGCCCTCGGC CGCCAGGGTC AGGGCGGCCG    18150
TCCGCGGATC CTCCTCCACC GGCCAGCGGG CGTAGGAGCG GCGCCAGTAC    18200
ATCAGCGGGC TGGGCACCCT CGGGCCGGGG CCCGCCGGCC CACCACCGCG    18250
CCGATCACGA TGGTGTGGTC GCCCGCTGTC GAGGGCCGCG GCCGACCCGG    18300
CACTCGGCGT GCGCGACGAC GTCGGCCGAC AGTGACCGGC ACGCCACCGG    18350
CGCTGCCCGG CTCCCACCGG GACGTCCCGG AAGCGGTCGT CCACGGGCGC    18400
GGCGAAGCGC GGGGACGTGG ACTCCCCCTC CGCCGCGCAG CACGTTGACG    18450
GCGAACTCGC CGCGCTCCAG GAGGGCCTTC AGCACCCGGC TGTCGCGGTT    18500
GATGCAGACC CAGCAGCAGG GGCGGGCCT TGGAGACGCT GCAGGCGGCC     18550
GAACAGGTCA ACCCGTACGG CTCCCCGTCC GGTCCCAGGG TCGTCACCAC    18600
GGTGACCCCG GTCGGCAGGG CGCCCATGAT CGACAGGAAG GTGTCGCCGT    18650
CCACCAGGCC GGGAGCCAGG TCCAGCGGCA GGGACAGGGG TTCGGGGGGC    18700
ATCGGTCCTC CACTCTCGGC GGGTCGGTGT CCCCATGCTC GCGGGGCGCC    18750
TTCGAGCCGG CGCCGGGCCG TCGTCGGGCC CTCCGCGCAC GCGAACGGGC    18800
GCGCAAACGG GCGCGCGAAC GGGCGCGCGC GAGGGCGCGC GGACGCGGCC    18850
GGAGCCGGAG CGGAAAAGCG CGTACCCCG GCACGGGGT GACCGGGGT       18900
ACGCGCGGTT CAGGGGTCG CGTGCGCGCG CTCACTCCTC GTCGCGCAGT     18950
TCCCGCAGCG GGAAGGTGAG CAGGAAGCCC ACCGCAAGGA TCAGGCCGCC    19000
GACCAGGAAC ATCGTGTCGA AGCCCGAGGT GAAGGCGTCG ACCGCCGAGG    19050
CGCTCAGGCC GCCGGTGGAG TCCGGGTCGG AGAGCGCACG GCGCACGGCC    19100
TCGTCCGGGT CGGCCCCGTC GAGCCTGCCG GCGGCGACGC CGAACAGCAC    19150
CGACATGAAG ACGGCGGCGC CGCTCGTGCC GCCGAGCTGG CGGAACAGCC    19200
CGGAGGCGGC GTTGGCCACG CCCAGCTCGG ACTTGGGCGC CGAGCTCTGG    19250
ATCGCCAGGG TGATGACGGT CTGGAGAGC CCGATGCCGA AGCCCAGCCA     19300
GGCCGCGATC ACCACGATCA CCGCGAGCGG GGTGTCCGCG CCCGCGGCGG    19350
AGAGCGACAG CAGTGCTCCG GCCATCGAGC CGAGGCCCAC GATCGCGGGC    19400
TTCTTGTAGC GGTTCCACTT CTTGATGATC TTGGCGCAGA TCGTCTGGGA    19450
GACGATCGCC CCGGTCATCA CCGGGATGAT CACCAGTCCG GCGACGGTGG    19500
CACTGCGCCC CTGCACCAGC TGCAGGAACA GCGGCAGGGT GGAGACCGTA    19550
CCGAAGATGC CGACGCCGAT GGTGAAGTTG ACGGCCGTGG TCATCGTGAT    19600
GCCACCGCGC CGGAACAGCC GTAGCGGGAC CATCGCCTCC AGCCCGCGGG    19650
CCCGTTCGGC GAGCACGAAC AGCACCAGGC CGATCAGCGA GACGGCGAAC    19700
AGCGTCAGCG AACGCGCCGA TCCCCAGCCC CAGTCGAGGC CCTCCTCCGC    19750
CACGATCAGC AGCGGCACCA GCAGAGCGC CAGGGTGAGC GCCCCCCGGA     19800
AGTCGATCGG GTGGTCCACC CTGCGGTGCG GCAGGTTGAG CGCCTTGCGC    19850
ACGCTGAGCA GCGCCACGAG ACCGAGCGGC ACGTTGATCA GGAAGGCCCA    19900
GCGCCAGCCG GTCACCCCGA GGATCTCGCC GGCGCCCGCG AACAGGCCCC    19950
CGACGAGCGG GCCGAGCACA CTGGCCGCCA CCCAGGCCAT CATCAGGTAC    20000
GAGAAGTAGC GCCCGCGCTC GCGCACCGGG GCGAGGTCGG CGATGACGGC    20050
CGTCGGCAGC GACATCAGCC CGGCGCCGCC GAAGCCCTGG AGGACGCGGG    20100
CGATCGCCAG CGTCTCCATC GAGTTCGCCA TCGCGCAGGC CGCCGAGCCG    20150
ACGATGAAGA CCGCGATCGC CGCCAGATAG AGCGGCTTGC GGCCGTAGAT    20200
GTCGGACAGC TTGCCGTAGA ACGGCATCGC GATCGTGGAG CTGACCAGGT    20250
AGCCGGTGAT CACCCAGGCC TGGACGGTCT GGCCGTGCAG TTGGTCGCCG    20300
ATCGTACGCA GCGCGGTGGA GACGATCGTC TGGTCGAGTG CGGCAGCAG     20350
CACGGCCAAC AGGAGCCCGG ACAGCGCGGT GATGATCTGG CGGTGAGTGA    20400
```

FIG. 4I

```
AGCCGGCGGG GCCGCCGGCC TCGTCCGCGA CGGCCTCGCC GGTCTGCGAG      20450
GTGGCGTTCG CCATTCCCAT TTCTCCCACC GAATTCGACA AGGTCTTGTC      20500
GAACTGAGCG TAGTGGGCTA CCGTGGCGGA ATGACAAGTT CTTGCCGAAA      20550
TCCCGGCCCG GACGAGGCTA GGCTGGCCGT GGAGAGCCTG CGATTAGGCT      20600
GCCCCCATGA CCGATCTCTC CCCCGCGGCC GAGACCTTGA GTGACATCAC      20650
CACCGAACTG TTCGCCGTCA ACGGAGCCCT GCTGCGCGCG GGCGACGCGC      20700
TGTCCGCCCG CTTCGGGCTC ACCTCCGCGC GCTGGCAGGT CCTCGGGCTG      20750
CTGGCCGAGG GGCCGCAGAG CGCCGCCCAC CTGGCGCGCG AGCGGGCTGC      20800
GCCGCCAGCC GTCCAGCAGA CCGTGGTGAA GCTGGTCGAG GAGGGCCTGG      20850
TCAGCACCTC CCCCAACCCG GCCGACCGGC GGGCCCCGTT GGTCTCGCTG      20900
ACCGCCAAGG GCACCGACGC CCTCGCCCGG ATCGAACCCG CCGAACGCCT      20950
GTGGATGGAG CACCTCGCGG GCGGCCTGGA TCCGGACGAC CTGACAGGCC      21000
ACGCTGCGGC TGCTGCGTGG CTTCGGGCGG TCCTGGCCGA GGGGCTGCCC      21050
CCGACGGCGG TCGGCGGCGC GGACGCCGCC GACGTCACAG GTCCAGCGTG      21100
ACCTCGTACT CGGCGAGCCA GGAGTTGAGC CACAGCACCA GCTCCAGACT      21150
GCCCCGGTCG TAGGGCCGGC TCACCGCCCC GGTCGGACGG GCAGCCGCGG      21200
CCAGGGCCCG CTCGCGGTCC AGCAGCGGCA GCACCGGAGC GTCCGGATCG      21250
GCGAGCACCC CGGCCAGTTC GGCCCGCAGG GCGCCCTCGT AGCCCGGATC      21300
CTGGGTCGCC GGGTACGGGG TCTTCACCCG CTCGACCACC GAGCGCGGCA      21350
GCAGGTCGGC CACCGCCGCC CGCAGCAGGC TCTTCTCCCG GCCGTCGAAA      21400
CTCTTCATCT CCCAGGGCAC GTTGAAGACG TACTCCACGA GCCGGTGGTC      21450
GCAGAACGGC ACCCGCACCT CGAGGCCGAC CGCCATGCTC ATCCGGTCCT      21500
TGCGGTCGAG CAGGGTCTGC ACGAAGCGGG TCAGGTTCAG GTGACCGATC      21550
TCGCGCATCC GCCTCTCGGG CGCCGACTCA CCCGGCAGCA CCGGCACTTC      21600
GGCGAGCGCC TCGGCGTACC GGGCCGCCCG GTAGCCGTCC AGGTCGAGCT      21650
TGTCCAGCAG ACCCGCCTGG AACAGCGAGC TGCCGCCGAA GTAGCGCGCC      21700
GAACCCGGGG TGAGCCACGG GAAGGTGGCC GCCCGCAGGG CCAACGGGTT      21750
GCGGAACCAC CGGTAGCCGC CGAAGAGTTC GTCCGCGGCC TCGCCGGACA      21800
GCGCCACCGT GACGTTCTCC CGCACCGCGC GGAAGAACAG GTAGAGCGAG      21850
GGCCACATGT CGCCCCAGTA CGCGGGCGGC AGGTCGGTGG CGCGCAGCAC      21900
CGCGGAACGC ACCGCCGGGT CCGACAGGCC GGGGCTGTCC AGCAGCACCT      21950
CCAGGTGGTC CGCTCCGACG TGCCCCGCCA GCTCGCGCAC GTACGGCGCG      22000
TCCGCCTCCC GCCGGACGGC GTCGGAGGCG AAGGCGTCGG CGGCGCCCCG      22050
GAAGTCCACC GAGAAGGAGC GCACCGGCCC GCTGCGGGCG GCCAGCGCCG      22100
TCACGGCCGA CGAGTCCAGG CCGCCGGAGA GCAGCGTGCC CAGCGGGACG      22150
TCCGAGACCA GCTGACGGGT GACGGTGTCG GCGAGCAGGT CACGGACGGT      22200
GCCGATGGTC GTCGGCAGGT CGTCGGTGTG CTCGCGGGCC TCCAGCCGCC      22250
AGTACGTCTG CCGGCGCACC CCGCCGCGCC CCACCCGGAC GAGCTGACCC      22300
GGACGGACCT CGACGAGCCC GGAGAAGACG GCCGCCTCGG GCGTCTTCAC      22350
CATGTCCAGC ACCTCGCACA GCCCGTCCGG GCCGACCCGG CGGGACAGGG      22400
TCCGGTCCGC CAGGACGGCC TTGGGCTCCG AGCCGAAGCG CACGCCGGCG      22450
GCGGTCGGCC AGTAGTAGAG CGGCTTGACG CCCATCCGGT CGCGGACCAG      22500
CAGGAGTTCC TCGCTGTGCT CGTCCCAGAC GGCGAAGGCG AACATCCCGT      22550
TGAGCCTCTC GACCAGCGCG GCGCCCACT  GGAGGTAGCC GCGCAGGACG      22600
ACCTCGGTAT CGCAGGACGT CCTGAACCGG TGGCCGTGCG AGGTGAGTTC      22650
GGCGCGCAGC TCACGGAAGT TGTAGATCTC GCCGCTGAAG GTGATCGCCG      22700
CGCCGCGGCC CTCGTGTTCC GCGGTCATCG GCTGCCGGCC GTGCTCGGGG      22750
TCGATCACCG ACAGGCGCCG GTGACCGAGC CCGGCCGCGC GGCCGAACCA      22800
GAGGCCCTCG GCGTCCGGCC CCCGGCAGGC CATGGTGTCG GTCATCGCCT      22850
GGAGCAGGTC CCGGCGGTGT TCGGCCGGGG CGTCGTAGTC GACCACCCCC      22900
ACGATTCCGC ACATGCTCAG CCGGCCGTGG CGAGACCGAG GTTGACCGCG      22950
```

FIG. 4J

```
TCCAGGAGCA TCCGCGGCGT GGTGGCCTCC ACCACGGTCT CGTCGGGCAG    23000
GGTGATGCCG CGCTCGCGCT CGATGGTGTT GAGGGTGTTG AACAGGGCGA    23050
GCGAGTCGTA GCCGAGGTCG GCGAAGGGGA CGTCCAGGAT GTCGTCGAGG    23100
GCGACGCCCT CGTCGGCTCC GGCAGCCTCC TTCAGCGCGG CGATCAGGTC    23150
GTCAAGGGTG AACTCTGCCA TGGCTGTTCC TCACATCGGT GGGTCGGTCT    23200
GTCGAATCCG GAAGGTCAGG CGGGCGGTCG GCCGGCCCGG TCAACTGGTC    23250
AGTACGAGAG CGCTGTTGAA GCCGCCGTGG CCGCGGGCGA GGACCAGCGC    23300
GCTGCCCAGC CGGGCCGGCC TCGGCGGTCC CAGCACCAGG TCGAGGTCCG    23350
GGTGGGCCGG CCGGCCGATG TGCACGGACG GCGGGATCAC CCCGTCCCGC    23400
AGGGAGAGCA GCGCGGCCGC GACGTCCAGC GGGGCGCCAC CGGCCAGCAG    23450
CCGGCCGGTC ATCGTCTTGG GCGCCGTCAC CGGCACCCCG CGCGGGCCGA    23500
ACACCGCGCC CAGCACCTCG GCCTCGGCGC GGTCCTGCTC GGCCACACCG    23550
CTGGCGTCGG CGAAGACCAC GTCGACGTCG GAGGGGCCGA TCCCGGCGTC    23600
GGCGAGCGCC GTGTCGATCG CCCGGCGCAG CCCGGGCGGG CGCCCGGAGC    23650
CGGGTCGGGG GTCGAAGGTG GCCGCGTAGC CGGCGATCCG CCCGTAGTGG    23700
CGGTGCTGCC CGCGCTCGGC GGCGCCGTCC GGGGTCTCCA GCACGAGCAG    23750
TGCGCCGCCC TCGCCCGGCA CCCCGCCGGA GGCGTCGGCG TCGAAGGGCA    23800
GGAAGGCCCG CTGCGGGTCC CGCCGGGGGC TGACCGTGCC GCTGCGGCTG    23850
AGGCAGAGCC ACGACCAGGG GCAGAGCGAG CCGTCCACCG CGCCGGCCAG    23900
CATCAGCGCG GTGCCCTCGC GCACGTGCCG GCGGGCCTTG GCCAGCGCGT    23950
CCAGGCCGCC CGCCTGCTCG GCCACCAGGG CCGAACCGGG GCCGCGCATG    24000
CCGTGCCGGA TCGAGATCTG CCCGGTGTTG ACCGGGTAGA ACCACGCGAA    24050
GGACTGGTAG GCGCTGACGT AGGCCGGGCC CTTGCTCCAC AGCGCCTGGA    24100
GTTCCTTCTG GCCGAACTCG AAGCCGCCGG CCGAGGCGGC CGTCACGACG    24150
CCGGCGGAGA AGTCCGGCAT CGTCGTCGGG TCCGCCCCCG CGTCGGCGAG    24200
CGCCTCCTCG GCCGCGACCA GGGCCAGCCG CGTCATGTGG TCGGTCTGCG    24250
GCAGCAGTCG GCCCGGCAGG TGTTCCTCCG GCGTGAAGTT CACCTCGCCG    24300
GCCACGTGCG CCCGGTACCC GGTGGAGTCG AAGCGGGTCA GCGGCCCGAG    24350
ACCGGACCGG CCCGCCAGTG TGGCGTCCCA GTACTCCGCA ACGCCCCAGC    24400
CGTTCGGTGC CACCACGCCG ATCCCGGTCA CCACGACGTC GGTCATCCCC    24450
GGCTCCACTC CGGCTCGGCG AGCACGATCG CGCTCTGGAA GCCGCCGAAG    24500
CCGCTCGCCA CGCTGAGCAC CGTGCGCACC CGCTGTTCCC GCGCCACCAG    24550
CGGCACGTAG TCGAGGTCGC ACTCGGGATC GGGCACGTGC AGGTTGGCCG    24600
TGGGCGGCAC CACCGAGTGC TCGATCGCCA GCGCGCTGGC GGCGAACTCC    24650
AGGGCGCAGA CCGCGCCCAG CGAGTGTCCG ATCATCGACT TGATCGAGCT    24700
GACCGGCACC CGGTAGGCGT GGTCGCCCAG GCTCTTCTTG AACGCGGCGG    24750
TCTCGTGCCG GTCGTTCTGC TTGGTCGCCG AGCCGTGCGC GTTGACGTAG    24800
CCGACGTCCT CGGGGTTCAT CCGGCTGCGG TCGAGCGCGA CCCGGATAGC    24850
CTCGGCCATC TCGTTCCCGT CGACCCGCAG CCCGGTCATG CTGTAGGAGT    24900
TGCAGCGCCC GGCGTAGCCG GTGACCTCGG CGTAGATGTG CGCGCCGCGC    24950
CGGATCGCGT GCTCCGCTC CTCCAGCACG AACATCGCCG CGCCCTCGCC    25000
GAGGGCGAAG CCGTTGCGGG TCAGGTCGAA GGGGCGCGAG GCGCTCTCGG    25050
GTTCGTCGTT GCGCGGGGTG GTCGCCTTGA TCGCGTCGAA GCAGGCCACC    25100
GTGATCGGGG AGATCGCCGC GTCCGAGGCG CCGGCCAGCA TCACGTCGGC    25150
CGCGTCGTCG CGGATCAGGT CGCAGGCGTG CGCGATCACG TCGATCCCCG    25200
AGGTGCATCC GGTCGACACC ACGCCCACCG GACCCTCCGC CTCGACCAGC    25250
CAGGCCAGTT CGGTGGCCAT CGAGGACGGG ACGAAGTAGT CGTAGAGGTA    25300
CGGGACGCCG TGCGCGTCGT CGACCAGCCG CTTGCGGCCC TCGTCGCTCA    25350
CCACGGCGAA CTCGCGGTCC AGACTGATCG TCATCCCACA GGCGGTGCCG    25400
GCCATCACCC CGGTGCGGAT CGGGTCGTTG ACGCCCGACA CCCCGAGTC    25450
GTCCAGCGCC TCGCGCGCGG CGACCACCGC GAACTGCGCG GTGCGGTCCC    25500
```

FIG. 4K

| | | | | | |
|---|---|---|---|---|---|
| ATTGACGGAT | CTGACGCTGC | GTCAACCCCG | CGGCCTGCGG | GTCGAAGTCG | 25550 |
| CACTCGGCGG | CGACCCTGGA | CCGGAACGGC | GAGGGGTCGA | AGGTCGAGAT | 25600 |
| CGTCCGGGTC | GCGGTCCGGC | CGGCCGTCAG | CAGCTCCCAG | AACGCCTTGG | 25650 |
| TGCCCACCTC | GCCCGGTGCC | ACCACGCCGA | TCCCGGTGAC | CACCACGCGC | 25700 |
| CGGCGGCCGT | CGTCAACTCC | CACCACTGCT | CCCCCTGTCG | ATCTCCCCGT | 25750 |
| GCGTGTCCGG | CGTCATGCCC | TGACCTCCTG | TCCGTGCGGC | CCGTCCGCGG | 25800 |
| GCTCGGGCGG | GCGGGGACTT | GAGCCGGATC | AGATCGTCCT | GGCAGGCGTT | 25850 |
| CGCGGCGGCT | TCGAGCCGCC | GTCCACGCGC | CTCCGGCCCC | CGCCTTCCCG | 25900 |
| CCGCGGCGGG | AAGAGCCGCA | CGCACGACGG | CGGCGGCGCC | GCACCCACGG | 25950 |
| CGGCGGGAAG | ACGACGCGAA | CCGGCGTCGA | AGGGCGCCCC | CTAGCGTCTG | 26000 |
| GCCGCATGGA | CATCGACACC | GACATCTGCG | TGGTCGGCGG | CGGCCCGGCC | 26050 |
| GGGCTGACCC | TCGCCCTGCT | GCTGGTCCGC | TCGGGCCTGC | GCGTCACCGT | 26100 |
| GCTGGAACGC | AGCCGCTCCC | TGGACCGGGC | CTACCGCGGC | GAGATCCTCC | 26150 |
| AACCCGGCGG | CCAGGCCTTG | CTGGACGAGC | TGGGCGTGCT | CGGCCCGGCC | 26200 |
| CGGGCGCACG | GCGCCGTCGA | GCACGACCGC | TTCCTGCTCG | AGGAGCACGG | 26250 |
| ACGCGTCCTC | ATCGACGGCG | ACTACCGGCG | CCTGCCCGGG | CCGTACAACT | 26300 |
| GCCTGCTGAG | CCTGCCCCAG | CGGCACCTGC | TGACCGAACT | GCTCGCGGCC | 26350 |
| TGCGAACGCC | ACGAAGGATT | CCGCCAGTTC | GCGGGCGCCA | AGGCCACCGC | 26400 |
| CCTGATCGAG | GAGGGCGGCT | TCGTCCGCGG | TGTGGTCGCG | GGCGGCGCGG | 26450 |
| GCGGCTCCCC | CGACCGGGTG | GTGCGGGCCC | GCTGCGTCGT | CGCCGCGGAC | 26500 |
| GGCCGCTTCT | CCAAGGTCCG | CTCGCTCGCC | GGGATCGGCT | ACCGGCGCCA | 26550 |
| GGAGCTGTTC | AGCCAGGACG | TCCTGTGGTT | CCGGCTGAGC | GCACCGCCGC | 26600 |
| GCACGGACAC | CCGACGCCCG | TGCGACGTCC | GGGTCTTCCG | GGCCGGCGGC | 26650 |
| AATCCGGTAC | TCAGCTACCG | CTCGGTGCCC | GAGGCGCTCC | AGCTCGGCTG | 26700 |
| GACCCTCCCG | CACGGCGGCT | TCCGCAAGCT | GGCCGACCGC | GGCATCGGCC | 26750 |
| ACATCGTCGA | CCAACTCGTC | GACGCCGCAC | CGGAGTACGC | CGACCTGATC | 26800 |
| CGCCAGGAGA | TCACCGGCTT | CGGCGACGTC | TCCCTGCTGG | ACGTCTTCTC | 26850 |
| CGGCAGCGCC | GAGCACTGGG | TGCGCGACGG | CCTGCTCCTG | ATCGGCGATG | 26900 |
| CCGCCCACAC | CCACAGCCCG | ATCGGCGCCC | AGGGGATCAA | CCTGGCCGTC | 26950 |
| CCGCCGCCGC | GTCGGGCCCA | CCCGGTGCTG | GTCGAGGCCG | TCCGCGGCGG | 27000 |
| CGACGCGGCG | CGGCCCGGCT | CGCCCCGTAC | GAACGGCAAC | GCCGCCCCCG | 27050 |
| AAGTGGAACG | GATCACCCGG | ATCCAGCAGG | TCCAGAGCCG | CATGATGCTC | 27100 |
| TCCACCGGGC | GCATCTCCTC | CACGGTGCGC | CCCCGGGCCG | CGGCGCTGGT | 27150 |
| GTCCAGGACC | CCGCTGTACG | GGGCCGTGCT | GCGCCGGATC | GCCTTCGGCA | 27200 |
| CCGCGCCCGT | CCGGCTGCGC | GCCGATCTGC | TCGCCGGGGC | GGGGCGGTGA | 27250 |
| GCGGCGGGGC | AGCGATCGCC | GCCGGCGACT | CGGCGACGGC | GAGCGGGGTG | 27300 |
| CTCCTCGCCC | TCGCCGTCGT | CCTCGCCAGC | GCGTTCGTCT | GCGGCCGGCT | 27350 |
| CGCCGCCCGG | GTGCGCCAGC | CCGTCGTCAT | GGGGGAGATC | GTCGGCGGGG | 27400 |
| TGGCCCTCGG | CCCCAGCCTG | CTCGGGCTGC | TGCCGGGGCA | CCTGGACGCC | 27450 |
| TCACTGTTCC | CGGCGGAGGT | CCAGTCCTAC | CTGCGGGTGC | TGTCCCAACT | 27500 |
| GGGCCTGGTG | CTCTTCATGT | TCACCGTCGG | CCTGCGCTTC | GACGTCGGCC | 27550 |
| ACCTGCGCGG | CGCCGGGCGC | CGGGTGACAG | CGGTGTCGCT | CAGCTCGGTG | 27600 |
| GCCCTGCCGT | TCGCGCTCGG | CGTGGGCTC | GCGGTGCTGC | TCTACCCCTG | 27650 |
| GTTCGACAAG | GCCCAGTTGA | GCACCGACGG | GAGGCTCGGC | CCGGCCCTGT | 27700 |
| TCCTGGGCGC | GGCGATGTCC | ATCACGGCCT | TTCCCGTCCT | CGCCCGGATC | 27750 |
| ATCGCCGAGC | GACGGATGCA | GCACGACCCG | CTCGGCAGCC | TGTCATTGGC | 27800 |
| CTGCGCGGCC | TTCCAGGACT | TCCTCGCCTG | GTGCGCGCTG | GCGGTGGTGG | 27850 |
| TGGCGGTGGT | GGAGGCCAAG | GGCCTCTGGT | CGCTGGGACG | GCTGGCGCTC | 27900 |
| GACACGGCGG | TGGTGGTCCT | GGTGCTGGTC | GGCGTCGTCC | GCCCGCTCCT | 27950 |
| CTCCCGGCTG | CTCGCCCCCG | GCCGGCGCCG | TCCCCTCCCC | CGGCCGTGGA | 28000 |
| TCCACGCGGT | GCTCGTCACC | GGCACCCTGG | TCACCGCCTG | GGTCACGGCC | 28050 |

FIG. 4L

```
GAGATCGGCC TGGACGCGGT GTTCGGGGCG TTCATGTTCG GTGCGGCGGT    28100
GCCCCGGGAC CGGATCGAGG CGATCGCGCC CGACGTCCCG GAGCAGATCG    28150
AGCGGGCGGG TCTCCTGCTG CTGCCGGCCT TCTTCGCGGT GACCGGCCTC    28200
GCCGTCGACC TCACCGGCCT CGGGCTGCGC GGCCTGGCCG TCGTGGCGGC    28250
GGTGCTGGTG GCGGCCTGCG CCGGCAAGTT CGTCGGTGCG GTCGCCGCCG    28300
CCCGGGCCAC CGGCTCGAGC CGGCGCGAGG CGCGGGTGCT CGGCATCCTG    28350
CTCAACGCCC GGGGCCTGAC CGAGCTGGTC ATCCTCAACG TGGGCCACCG    28400
GCTCGGGGTG ATCGACACCC GGATGTTCAC CGCCATGGTG GTGATGGCCC    28450
TGGTCACGAC GCTGATGACG GGGCCGCTCC TGGAGCGCCA CACGGCGGGC    28500
TCCGCCGGAT CCGCCACGCT CCCGGACCCG GCGCCCGAGG CCGCACAGGC    28550
CTCGCGGACA ACCTCCTGAT GGCGGGCCGG CCACGACCTC CGGGGGGCGT    28600
GCCCCTCACG GCGGCTCCGT CCACCCGGAG ACCCGGCGCA GCCGCGACTC    28650
AGCCGCCGCT CGACCGGGCT GAGCGGAACG TCGGGCGCA GCCGCTCCGG    28700
GTGCCCCGAC GGTGGCCCGC CCCCGGCAGG GCCGCCCGGC TCGCCGGGCG    28750
CCGGACCGGC CCGGGCTGCG GCGGCGGGC CACGTAGCCG GCCATCTGCC    28800
CCAGCGCCGC CAGTCCGCGC AGGAGCACGG CCAGCAGATC GAGGAGCCGT    28850
TCGTTCGGTT CGCACATCCG CCGAGCATGG CGACCGGTCC TGAAGCGCGG    28900
TTCGAGCGGT ACGGGAGGGG CGCCGGGCAC GGCGGAGAGG ACAGCCCGGC    28950
ACCCTCGGAA CCGCTGGAGC ATGACCACGG CGCCGTCGGA GCTGCGGGTG    29000
CCCGTCACAC TGACGATCCG CCGCAGGAGG GTCGGGCGTG TCCGAGGGTT    29050
CCCGCCGGAC CGGCCCCGAG CCTCACTGGT ACCGGTAGGT GGCGGCCACC    29100
GCGAGGTGGT CGCTGCCGTC CCGGGGCAGG GTGCGGGAGT CCACCGGCTT    29150
CAGCCCGCCC TTGCTCATGA TCTGGTCGAT CCGCGCCATC GGGAACGCCG    29200
CGGGCCAGCT GAAGCCGAAG CCGTCCCCGG CCGCGCCCTG GCCGAGCGC    29250
ATCTGCGAGG TGACCGGTGC CAGGCTGCGG TCGTTCATGG TGCCGTTGAG    29300
GTCGCCGAGC AGCAGGACCT TCTTCACCGG CTCGGCCTGG ATCGCGTCGC    29350
CGAGCGCCTG GGCGCTGACG TCCCGCTGGT GGGCGGTGAA GCCGCTCTCG    29400
GCCTTGAGCC GGACGGACGG CAGGTGCGCG ACGTACACCG CGACCGGGCC    29450
CTGGGGGGTG GTGACCCGGG CCCGGAAGGC CCTGGTCCAA CCGATCTTCA    29500
GGTCCACCGA GGAGACCTCG CCGATCGGGT ACTTCGACCA GAGTCCGACC    29550
GTCCCCTCCA CCGTGTGGTG CGGGTACGCC CCGGCGAGCC CGGTCTCGTA    29600
CGACCGCAGC TGGTTGCCGG CCAGTTCCTG GAGCGCGACG ATCTGGGCGT    29650
CCGAGGCGAC CAGGCCGCGG ATGGTGCCCG GCACGTCGGT GTTCCCGGCC    29700
TCGACGTTGT GGGTGACCAC CGTCCAGTCG CCGGTGCCGC CGCTCTTGTC    29750
GGACACCAGC CCGCCGAACA GGTTGGCCCA CAGCACGGCG GGCACCAGCA    29800
GGGCGAGCAG CGCGGTGGCG GAGCGGCGCA GCAGCGCGGG CACCAGCAGC    29850
ACCGGGACGG CCAGGCCGAC CCAGGGCAGG AAGGTCTCCA GCAGGCTGCC    29900
GAGGTTGCCG ACGCTGTTCG GCATCTCGGC GTGGAAGGCC AGCAGCACCG    29950
CGGTGAGCAG GGCCAGCAGG GCGATCGGCC AAGTGGGCGG CCGTCGGGAT    30000
C                                                        30001
```

CLONING OF THE BIOSYNTHETIC PATHWAY FOR CHLORTETRACYCLINE AND TETRACYCLINE FORMATION AND COSMIDS USEFUL THEREIN

RELATED U.S. APPLICATION DATA

This application is a continuation-in-part of two U.S. applications, (1) Ser. No. 07/821,109, filed on Jan. 15, 1992, now abandoned, which is a continuation of application Ser. No. 07/558,040, filed on Jul. 26, 1990, now abandoned, and (2) Ser. No. 07/821,419, filed on Jan. 15, 1992, now abandoned, which is a continuation of application Ser. No. 07/558,039, filed on Jul. 26, 1990, now abandoned.

BACKGROUND OF THE INVENTION

Description of the Related Art

The antibiotic chlortetracycline and its derivative compounds (e.g., tetracycline, demethylchlortetracycline, demethyltetracycline) are produced commercially in submerged fermentation by *Streptomyces aureofaciens* (Dugar, 1948). More than thirty years of industrial manipulation of this microorganism has resulted in the development of sophisticated fermentation techniques and media formulations that have allowed significant improvements in fermentation yield (Goodman, 1985). These advances in yield improvement have also been aided by the isolation of mutants of *S. aureofaciens* with increased ability to produce antibiotic (Veselova, 1969). These high-producing strains have largely been isolated by the process of mutagenesis, followed by random screening for improved yield. The same techniques allowed the isolation of mutants blocked in antibiotic biosynthesis which were critical tools for the elucidation of the biosynthetic sequence for chlortetracycline formation (McCormick, 1968). Despite these accomplishments, an understanding of the genetic regulation of chlortetracycline biosynthesis was not completely realized. Recent developments in the field of Streptomyces genetics have created the opportunity to study molecular genetics of organisms producing industrially important metabolites.

The demonstration of recombination of chromosomal markers by the fusion and subsequent regeneration of Streptomyces protoplasts (Hopwood et al., 1978 and Baltz et al., 1981) was a pivotal event in the genetics of the actinomycetes. Prior to the development of techniques for protoplast fusion, genetic crosses could only be reliably performed in a few species with demonstrated conjugal systems (Hopwood, 1967). Now, genetic analysis can be performed in any species which can be protoplasted and regenerated. More importantly, protoplasts later proved to be an ideal substrate for transformation by plasmid DNA, thus creating the opportunity to do recombinant DNA experiments in these organisms (Bibb et al., 1978). The isolation of genes for several antibiotic resistances, such as thiostrepton, viomycin and neomycin, allowed the construction of readily selectable cloning vectors from indigenous Streptomyces plasmids (Thompson et al., 1982).

One of the first antibiotic biosynthetic genes to be cloned was the O-methyltransferase involved in the formation of the antibiotic pigment undecylprodigiosin (UDP) (Feitelson et al., 1980). The gene was identified by its ability to complement a known mutation in the UDP biosynthetic pathway. Other techniques employed in these early efforts to isolate biosynthetic genes included mutational cloning using phage ØC31 for methylenomycin (Chater et al., 1983), a sib selection of recombinant clones using in vitro enzyme assays for the actinomycin phenoxa-zinone synthetase (Jones et al., 1984) and sulphonamide resistance conferred by the p-aminobenzoic acid synthetase involved in candicidin production (Gil et al., 1983). Bialaphos biosynthetic genes were identified via complementation of blocked mutants (Murakami et al., 1986).

Genes involved in actinorhodin biosynthesis were cloned by complementation of biosynthetically blocked mutants of *Streptomyces coelicolor* (Malpartida et al., 1984). In this last case, two overlapping clones complementing distinct classes of mutants were combined on a single plasmid which was shown to confer the ability to synthesize actinorhodin when introduced into a heterologous *Streptomyces parvulus* host.

Another important series of observations was that genes for antibiotic biosynthesis were physically linked to the resistance determinant(s) for that same antibiotic in the producing organism. Thus, a DNA fragment from *Streptomyces griseus* conferring streptomycin resistance was shown to be contiguous with DNA that complemented biosynthetic blocks (Distler et al., 1985). The same situation was seen in *Streptomyces fradiae* where biosynthetic genes had been identified by probing a cosmid library for homology to a mixed-base oligonucleotide constructed to represent the DNA sequence for the aminoterminus of the final enzyme in the tylosin biosynthetic pathway (Fishman et al., 1989). A previously cloned tylosin resistance gene (tlrB) was shown to be contained within this region of DNA, which complemented nine classes of blocked mutants (Baltz et al., 1988). In the cases of puromycin (Vara et al., 1988) and tetracenomycin (Motamedi et al., 1987), a primary selection for expression of antibiotic resistance gene in the heterologous host *Streptomyces lividans* allowed subsequent identification of antibiotic biosynthetic genes located on the same cloned DNA fragment.

The use of nucleic acid probes has aided the isolation of biosynthetic genes. This approach relies on the existence of a pre-existing body of information concerning the pathway or prior cloning having been performed. Thus, in the case of tylosin above, a probe was constructed using information from a partial amino acid sequence of a biosynthetic enzyme (Fishman et al., 1987). Similarly, the gene for isopenicillin N synthetase was cloned from *Streptomyces clavuligerus* by identifying a clone hybridizing to an oligonucleotide probe constructed with a knowledge of the N-terminal amino acid sequence of the enzyme (Leskiw, 1988). Genes involved in the biosynthesis of erythromycin were identified by probing a cosmid library with a previously cloned erythromycin resistance gene (Stanzak, 1986). Similarly, genes involved in the biosynthesis of oxytetracycline have been identified by hybridization to both a previously cloned resistance determinant (Butler et al., 1989) and an oligonucleotide synthesized to represent the DNA sequence corresponding to the partially elucidated amino acid sequence of the biosynthetic enzyme anhydrotetracycline oxygenase (Binnie et al., 1989). The use of heterologous actI and actIII probes allowed the identification of genes involved in anthracycline biosynthesis in *Streptomyces peucetius* (Stutzman-Engwall et al., 1989).

The use of these techniques individually or in combination has allowed the isolation or assembly of entire biosynthetic pathways from fragments of genes, and in some instances, their expression in a heterologous host. The entire biosynthetic cluster for bialaphos was cloned by a combination of selections for complementing activities and heterologous expression of bialaphos resistance (Murakami et al., 1986). While a successful isolation of the entire pathway in a single step in *Streptomyces lividans* by selecting for bialaphos resistance was noted, no mention is made concerning expression of the biosynthetic genes.

A bifunctional cosmid clone which hybridized to a homologously derived erythromycin resistance determinant was isolated from a *Saccharopolyspora erythrea* library and shown to direct the synthesis of erythromycin when transferred to *Streptomyces lividans* (Stanzak et al., 1986). An *E. coli* cosmid clone that showed hybridization to both an oxytetracycline resistance gene probe and biosynthetic gene probe (for anhydrotetracycline oxygenase) allowed the isolation of the oxytetracycline biosynthetic cluster from *Streptomyces rimosus* (Binnie et al., 1989). Subsequent subcloning into a Streptomyces plasmid vector allowed production of oxytetracycline in *Streptomyces lividans*.

Two overlapping clones from the tetracenomycin producer were identified by complementation of blocked mutants of *Streptomyces glaucescens* and ability to confer tetracenomycin resistance in *S. lividans* (Motamedi et al., 1987). When both were separately resident in *S. lividans* and co-fermented, or when they were co-resident in the same *S. lividans* host, tetracenomycin was produced. Bifunctional clones isolated from an *E. coli* library of *Streptomyces peucetius* DNA by hybridization to actI and actIII probes of *S. coelicolor* were shown to direct the synthesis of pigmented antibiotic when introduced into *S. lividans* (Stutzman-Engwall, 1989).

Additionally, the isolation of the biosynthetic pathway for cepthamycin C production has occurred (Chen et al., 1988). In this case, random clones in *S. lividans* were individually screened for cephamycin C production using an agar plug fermentation method. Out of 30,000 screened, one transformant of *S. lividans* was shown to be producing cephamycin C.

Although reports have been published concerning the cloning of a tetracycline-resistance determinant (Reynes et al., 1988) and a bromoperoxidase (Van Pee, 1988) from *Streptomyces aureofaciens*, these studies are in no way extended toward the isolation of chlortetracycline biosynthetic genes or the entire gene cluster.

The present invention is the first instance wherein the single DNA gene cluster related to the entire biosynthetic pathway for producing tetracycline and chlortetracycline is isolated and utilized.

BRIEF DESCRIPTION OF THE DRAWINGS

The background of the invention and its departure from the art will be further described hereinbelow with reference to the accompanying drawings, wherein:

FIG. 1 shows the structure of the components of the bifunctional cosmid vector and method for generating cosmid arms. Cosmid vector arms L and R are generated from plasmids A and B, respectively, as shown in the figure and as detailed in Example 3. Single lines represent *Escherichia coli* replicon portions of the constructs. In plasmid A, the *E. coli* portion is derived from the 3.7 kb EcoRI-SalI fragment of pBR322 (Sutcliffe, 1979). Plasmid B contains a 5.9 kb EcoRI-SalI fragment from SCP2* (striped) that provides for replication function in the actinomycetes (Larson et al., 1986). Three tandem cohesive end sites derived from a 700 bp BglII-BstEII cos-containing fragment of pHC79 (Hohn et al., 1980) are provided on both plasmids (open). The thiostrepton-resistance gene (darkened) present in plasmid A is derived from a 1.1 kb BclI fragment recovered from pIJ702 (Katz et al., 1983). A 1.1 kb spacer region in plasmid A (stippled) is derived from a SacI fragment of bacteriophage λ (Sanger et al., 1982).

FIGS. 4A–4L show the total DNA sequence from the cosmid clones designated LP$^2$127 and LP$^2$128 (this sequence is also set forth in Sequence I.D. No. 1). The sequence is obtained using the dideoxy chain termination method (Sanger et al., Proc. Natl. Acad. Sci. USA, 74:5463–5467, 1977). The *S. aureofaciens* DNA carried in the cosmid clones is fragmented either by digestion with appropriate restriction endonuclease or by sonication. The smaller pieces are eventually cloned into the M13 vectors M13mp18 and M13mp19 (Yanisch-Perron et al., Gene 3:103–119, 1985) using conventional methods and vectors (see, e.g., Sambrook et al., Molecular Cloning: A Laboratory Manual, 2d ed., Cold Spring Harbor Laboratory Press, Cold Spring Harbor, N.Y., 1989). The DNA sequencing is carried out at elevated temperatures using Taq DNA polymerase employing fluorescently-labeled primers using materials and methods supplied by the manufacturer (Applied Biosystems, Foster City, Calif.). The data are collected using a Model 370A/373A DNA sequencing system (Applied Biosystems, Foster City, Calif.). Compilation of the data, generation of overlapping sequences and the overall analysis of this DNA sequence information are carried out using the collection of standard computer programs contained within the Genetics Computer Group package (Devereaux et al., Nucleic Acids Research, 12:387–395, 1984).

SUMMARY OF THE INVENTION

Figure 2:
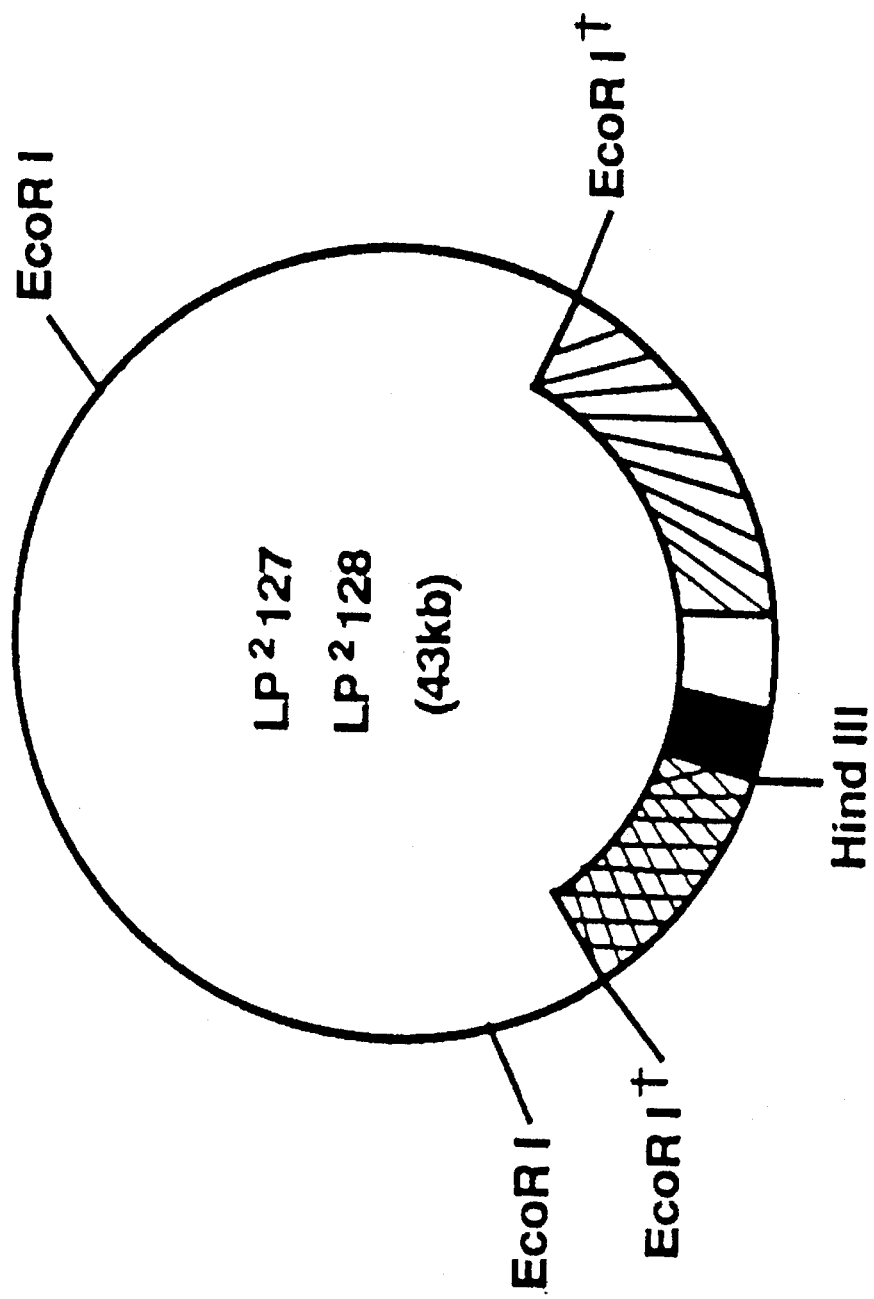
FIG. 2 shows a physical map for LP$^2$127 and LP$^2$128. Both plasmids show equivalent structures by restriction mapping. Therefore, a single structure, representative of both, is shown here and in FIG. 3. The vector portion is represented by double line. The TC/CTC biosynthetic region is shown as a single line. The DNA cloned from *S. aureofaciens* is 31.9 kb; the vector is 11.1 kb. The vector regions denoted are pIBI-24 (hatched), thiostrepton-resistance (striped). The two EcoRI sites marked with a (+) are vector-derived and flank the Sau3A-BglII junction which demarcates vector and *S. aureofaciens* DNA.

The present invention relates to the cloning of the entire biosynthetic pathway for the formation of tetracycline and chlortetracycline from *Streptomyces aureofaciens* and its expression in a heterologous host such as *Streptomyces lividans*. In particular, the present invention concerns the purified and isolated nucleic acid molecule, e.g., a DNA gene cluster, coding for the biosynthetic pathway for producing the antibiotics or an analogue thereof.

The more detailed description of the present invention is provided hereinbelow through nonlimiting examples which are illustrative of the invention.

DETAILED DESCRIPTION OF THE INVENTION

In accordance with the present invention, there is provided a single, purified and isolated nucleic acid molecule which encodes the entire pathway for the biosynthesis of chlortetracycline and, indirectly, for the biosynthesis of tetracycline and analogues thereof. The nucleotide sequence of the nucleic acid molecule is shown in FIG. 4. Desirably, the nucleic acid molecule is a DNA gene cluster isolated from *Streptomyces aureofaciens*, or an antibiotic-producing mutant thereof, and expressed in a suitable heterologous host, such as an Actinomycetales, preferably *Streptomyces lividans*, which will make the antibiotics.

The present invention further includes the DNA sequences which hybridize under standard or stringent conditions to the sequence of the nucleic acid molecule isolated from the microbial source and encode for the biosynthetic pathway of tetracycline, chlortetracycline or the analogues thereof. It should be understood to those skilled in the art that the invention encompasses the purified and isolated polypeptides which may be encoded by the sequences of the nucleic acid molecules of this invention.

Additionally, the invention embraces a two-plasmid system and the use thereof for cloning the biosynthetic pathway of tetracycline, chlortetracycline or the analogues thereof. The preparation of the system is explained in Example 3 and the structures designated A and B are shown in FIG. 1. Together, the plasmids comprise an efficient cosmid vector which allows for the cloning and packaging of large, contiguous pieces of DNA. It is contemplated that these plasmids described herein may be employed for cloning large DNA from any source.

For the isolation of the biosynthetic genes, a screen of a recombinant *S. lividans* library for a clone expressing tetracycline-resistance is utilized. The *S. aureofaciens* DNA inserts in the recombinant cosmids which comprise the library are large since the constraints of the in vitro lambda packaging system demands cosmid molecules with DNA inserts of 25–40 Kb to yield a viable transducing phage particle. When tetracycline resistant clones are selected from among this population of *S. aureofaciens* genomic clones, a limited subset of cosmid clones is chosen. Many or all of these are expected to contain antibiotic biosynthetic genes linked to the selected tetracycline resistance gene. Among those that are sufficiently large and correctly positioned is a subset encompassing the entire biosynthetic pathway. Thus, the cloning of all of the genes for tetracycline and chlortetracycline formation is unexpectedly possible without any pre-existing knowledge of the structure or sequence of the region.

The method for isolating the DNA involves lysozyme digestion of cells in an osmotic buffer, followed by gentle lysis, protein extraction and enrichment for, and concentration of, high molecular weight DNA. Although the method described is efficient, those skilled in the art will recognize that a variety of alternative procedures may be employed such as those described by Hopwood et al., 1985.

The source of total DNA used in the examples is *Streptomyces aureofaciens* ATCC 13899 but the invention is not limited to this particular source. A variety of other *Streptomyces aureofaciens* strains producing antibiotics of the tetracycline class can be used in the present invention with equal success. These strains include mutant strains and alternative wild-type isolates producing chlortetracycline, tetracycline, 6-demethylchlortetracycline, 6-demethyltetracycline, 7-chloro-5a,11a-dehydrotetracycline, 2-decarboxamido-2-acetyltetracycline and other members of the tetracycline family of compounds. The present invention relates also to the cloning of chlortetracycline, tetracycline and tetracycline-related compounds from other organisms producing such compounds, which include, but are not limited to, *Streptomyces rimosus*, *S. avellaneus*, *S. lusitanus*, *S. viridifaciens*, *S. psammoticus*, *Actinomadura brunnea* and *Dactylosporagium vesca*.

A partial digestion of *S. aureofaciens* DNA with restriction endonuclease Sau3A to generate large DNA fragments in the desired 35-kilobase size range with ends homologous to those of the arms of the bifunctional cosmid vector is employed. In this case, an empirical determination of the optimal digestion conditions is obtained by conducting a series of digestions and analyzing a sample of the end products by agarose gel electrophoresis. Those skilled in the art will recognize alternative library construction and recovery methods for cloned DNA of interest. The present invention is not limited to the use of *Escherichia coli* and the size selection imposed by lambda packaging as described herein, since other vectors may be useful as well. Those skilled in the art will recognize that monofunctional Streptomyces vectors, such as pIJ922 (Lydiate et al., 1985), can be employed in the present invention with the proviso that library construction and recombinant plasmid recovery are conducted within the actinomycete.

The steps that follow in the examples involve in vitro packaging of the ligation products of cosmid arms and size fractionated DNA, transduction to *E. coli* X2819T, collection of the population of transductants and isolation of DNA from them to give a cosmid library. The methods used are described, but the invention is not limited by those described in the example. Alternative methods could be employed to the same end with no untoward consequences. Thus, alternative protocols for ligation and in vitro packaging may be employed, as well as alternative recombination-deficient (recA) *E. coli* hosts, library amplification procedures (e.g. selective broth growth) and plasmid preparation procedures, all of which have been published in the scientific literature (Maniatis et al, 1982).

Subsequent steps in the examples describe introduction of the pooled cosmid DNA preparation into *Streptomyces lividans*, creation of a cell library and subsequent screening of such a library for transformants of *S. lividans* exhibiting resistance to 100 µg of tetracycline/mL. Though more laborious, transformants could be directly screened for tetracycline-resistance by replica plating. Alternative levels of tetracycline could be used for screening as dictated by the innate resistance exhibited by the host or source organisms. Other tetracycline-sensitive, non-restricting hosts, such as *Streptomyces griseofuscus*, could be substituted for *S. lividans*.

Next, recovery of recombinant plasmid by isolating plasmid DNA from the tetracycline-resistant *S. lividans* followed by in vitro packaging of said DNA and transduction into *E. coli* is obtained. Plasmid DNA isolated from such transductants is structurally characterized by restriction enzyme mapping analysis; and the two plasmids isolated in the example, Lp$^2$127 and LP$^2$128, are shown to possess equivalent structures. Those skilled in the art will recognize that similar DNA regions cloned from alternative organisms could show polymorphism in the arrangement of restriction sites, but that a sufficiently large DNA fragment conferring tetracycline-resistance would be expected to confer the properties described hereinbelow.

The plasmid-borne nature of the tetracycline resistance is confirmed by demonstrating that thiostrepton-resistant transformants of *S. lividans* obtained with LP$^2$127 and LP$^2$128 are also tetracycline resistant. The elaboration of tetracycline-like antibiotic is demonstrated by the production on agar by the aforementioned thiostrepton and tetracycline resistant *S. lividans* of antibiotic activity effective against *E. coli* but less so against a tetracycline-resistant *E. coli*.

Finally, it is demonstrated that the synthesis of tetracyclines is directed by LP$^2$127 in the heterologous host *Streptomyces lividans*. This is accomplished in both agar and broth fermentation. Both the originally isolated tetracycline resistant *S. lividans* and a LP$^2$127 transformant of *S. lividans* produce tetracycline and chlortetracycline under conditions where the same products are isolated from the DNA source organism *Streptomyces aureofaciene* ATCC 13899. On the other hand, a *S. lividans* transformant containing only plasmid vector with no inserted DNA shows no antibiotic production.

The demonstration of production of tetracyclines by the heterologous host is not limited to the fermentation conditions or HPLC analytical systems described in the example, although these clearly allow efficient analysis. A large number of procedures for fermentation and analysis of tetracyclines have been described and can be substituted herein. Also, although *Streptomyces lividans* is used as the heterologous host in the examples, the heterologous expression of antibiotic biosynthetic genes is expected in a number of actinomycetes and other bacterial groups including, but not limited by Bacillus, Corynebacteria, Thermoactinomyces, so long as they are transformed with the relatively large plasmid constructions described here. Those that are transformed include such as *Streptomyces griseofuscus* and *Streptomyces ambofaciens* which are known to be relatively non-restricting.

EXAMPLE 1

PREPARATION OF STREPTOMYCES AUREOFACIENS TOTAL DNA

A lyophilized preparation of *Streptomyces aureofaciens* ATCC 13899 is suspended in 0.8 mL of 1X synthetic salts solution (6 g of Na$_2$HPO$_4$/L, 3 g of KH$_2$PO$_4$/L, 0.57 g of sodium citrate/L) and plated onto Bennett's agar (1 g of yeast extract/L, 2 g of NZ-Amine A/L, 1 g of beef extract/L, 20 g of D-glucose/L, 20 g of Bacto-agar/L). After incubation at 28° C. for two days, cells from a single plate are scraped into 5 mL of Trytic Soy Broth (Difco) and sonicated briefly (~10 seconds) with a Heat Systems Ultrasonics W200P sonicator equipped with a microtip. A seed culture is developed by inoculating 2 mL of the sonicated suspension into 50 mL Tryptic Soy Broth (TSB), followed by incubation at 28° C., 200 rpm for 2 days. Five mL of seed culture is then inoculated to 100 ml TSB supplemented with 2% glycine and incubated at 28° C., 200 rpm for 48 hrs.

Cells are harvested by centrifugation at 9800 Xg for 30 minutes. The cell pellet is washed with 200 mL P medium (100 g of sucrose/L, 0.2 g of K$_2$SO$_4$/L, 2 mL of trace element solution/L which consists of 40 mg of ZnCl$_2$/L and 10 mg/L each FeCl$_3$.6H$_2$O, CuCl$_2$.2H$_2$O, MnCl$_2$.4H$_2$O, Na$_4$B$_2$O$_7$.10H$_2$O and (NH$_4$)$_6$ MO$_{724}$.4H$_2$O). The cell pellet is frozen at −20° C. then defrosted and suspended in 12 mL P$^+$ (P medium supplemented to contain 25 mM TES, 25 mM CaCl$_2$, 10 mM MgCl$_2$, 03.7 mM KH$_2$PO$_4$) containing 10 mg/mL lysozyme (Sigman, 3X recrystallized). The cells are incubated at room temperature for 2 hours by which time protoplast formation is evident. An addition of 2.5 mg of Proteinass K (Boehringer-Mannheim) is made and the mixture incubated at 37° C. for 15 minutes. Lysis is achieved by adding 10 mL 0.2M EDTA pHS, 0.1M Tris pH 8 followed immediately by the addition of 2.4 mL 10% sodium lauryl sulfate (SDS). The viscous mixture is incubated at 50° C. for 60 minutes with occasional gentle mixing.

Once lysis is complete, 20 mL of equilibrated phenol (50 g phenol +6.5 mL of 100 mM NaCl, 10 mM Tris pH8, 1 mM EDTA pH8+0.05 g 8-hydroxyquinoline) is added, the preparation gently shaken and then spun in a table top centrifuge at 1500×g for 30 minutes. The aqueous top layer is collected and re-extracted as above; the spent phenol from the first extraction is back-extracted with 20 mL 10 mM Tris pH7.4, 1 mM EDTA pH 8 (TE). The collected aqueous phases are then extracted with an equal volume of chloroform, spun as above and 10-mL portions distributed to separate test tubes. One mL of 3M ammonium acetate pH 5 is added to each and 10 mL of cold ethanol layered on top of the viscous solution. The DNA is gently spooled onto a glass rod, rinsed twice in cold ethanol and dissolved in 8 mL TE overnight at 4° C. An A$_{260}$ spectrophotometric reading is taken as an estimate of total nucleic acids present (predominantly DNA).

EXAMPLE 2

PARTIAL DIGESTION AND SIZE ENRICHMENT OF *S. AUREOFACIENS* DNA

A partial digestion condition that yields Sau3A digestion products of *S. aureofaciens* DNA in the range of 35 kilobases (Kb) is determined empirically. A series of reaction tubes containing ~25 μg DNA contained in 300 μL of reaction buffer consisting of 100 mM NaCl, 10 mM Tris pH7.4 10mM MgCl$_2$ are prepared, and restriction endonuclease Sau3A (New England Biolabs) added to give final concentrations of 0.5, 0.1, 0.05, 0.01, 0.005 enzyme units/μg DNA. The reactions are incubated at 37° C. for 60 minutes, then placed at 65° C. for 20 minutes and finally removed to ice. Twenty μL is removed and loaded to 0.5% agarose gel for size comparison to fragments of known length (lambda DNA digested with HindIII, XhoI and undigested). The DNA in the remaining volume is precipitated by the sequential additions of 50 μL 3M ammonium acetate and 1 mL ethanol, followed by chilling at ~20° C. The precipitated DNA is then pelleted by centrifugation at 8800 Xg, redissolved in 300 μL 0.3M ammonium acetate, similarly precipitated, pelleted, rinsed with ethanol, vacuum dried and the dried pellet finally dissolved in 100 μL TE. An inspection of the ethidum bromide stained agarose gel which is electrophoresed overnight at 1 volt/cm, reveals that digestion with 0.05 units Sau3A/μg DNA gives digestion products largely in the desired 35 Kb size range.

EXAMPLE 3

PREPARATION OF COSMID ARMS

The components of the bifunctional cosmid vector are retrieved from plasmids A and B shown in FIG. 1. Plasmid A contains pIBI24 which provides an origin of replication and an ampicillin resistance gene for replication and selection in *E. coli*. This plasmid also provides a thiostrepton-resistance gene for plasmid selection in the actinomycetes, as well as multiple cohesive end sites (cos) from bacteriophage lambda which serve as substrates for in vitro packaging. Plasmid B is designed to provide an SCP2 * origin of replication for plasmid maintenance in the actinomycetes, and multiple cos sites.

Plasmid A is digested With Asp718 and then desphosphorylated with calf intestine alkaline phosphatase (CIAP). The DNA then is extracted with chlorpane and chloroform, precipitated with ethanol and vacuum dried. The DNA is then resuspended and digested with BglII. Plasmid B is digested with SalI and subsequently treated with CIAP. After chlorpane extraction, ethanol precipitation and vacuum drying, the DNA is resuspended and digested with BglII.

The digestion reactions noted above are loaded to an agarose gel and electrophoresed overnight. A 6 Kb fragment from plasmid A and an 8.0 Kb fragment from plasmid B, which contain the functional regions described above, are isolated from the agarose gel by electroelution.

EXAMPLE 4

LIGATION OF COSMID ARMS TO SAU3A DIGESTED GENOMIC DNA AND IN VITRO PACKAGING

The Sau3A digested and size "inspected" genomic fragments of *S. aureofaciens* DNA are Joined to cosmid arms via in vitro ligation. Four μL Sau3A digested *S. aureofaciens* DNA, corresponding to ~8 μg, are combined with 1 μg each of cosmid arms 1 and 2 in a 10 μL ligation mixture that contains 66 mM Tris pH7.4, 10 mM $MgCl_2$, 1 mM ATP, 10 mM dithiothreitol and 40 units (cohesive end unit) T4 DNA ligase (New England Biolabs). The ligation mixture is incubated at 11° C. for 18 hours then subjected to an in vitro packaging reaction by adding the entire 10 μL reaction to a Packagene$^R$ lambda DNA packaging system extract (Promega Biotec). After a 2 hour incubation at room temperature, 500 μL phage dilution buffer (PDB) (100 mM NaCl, 10 mM TRIS-HCl pH 7.4, 10 mM $MgSO_4$) is added followed by the addition of 25 μL chloroform. The mixture is vortexed and stored at 4° C.

EXAMPLE 5

TRANSDUCTION INTO *ESCHERICHIA COLI* AND PREPARATION OF A BIFUNCTIONAL COSMID LIBRARY

The phage preparation derived from the in vitro packaging reaction is transduced into *Escherichia coli* X2819T (R. Curriss), with the objective of obtaining thousands of transductants from which a pooled plasmid DNA preparation, or bifunctional cosmid library, can be obtained. To this end, 0.3 mL of an overnight culture of X2819T is inoculated into 10 mL 20-10-5 (20 g of Tryprone/L, 10 g of yeast extract/L, 5 g of NaCl/L, 50 mg of thymidine/L) and incubated at 28° C., 2.5 hours. Four portions of 0.4 mL X2819T cells are then combined with 0.8 mL PDB and spun in a microfuge at full speed for 5 minutes. The pelleted cells are suspended in 100 μL PDB. Then 50 μL of phage preparation from in vitro packaging is added to each. Phage are absorbed to cells at 37° C., 25 minutes. Two mL of 20-10-5 are added to each mixture and the suspension incubated with shaking at 28° C. for 2 hours. One-tenth mL aliquots are plated onto a total of 50 Petri plates containing 20-10-5 agar (20-10-5 broth and 20 g of Bacto agar/L) supplemented with 100 mg of ampicillin/L (sodium salt-Sigma). The plates are incubated at 28° C. overnight and then left at room temperature for three days. A plate count of five representative plates reveals that a total of ~12,000 ampicillin-resistant colonies are obtained.

Each plate is flooded with 5 mL of solution consisting of 50 mM glucose, 25mM Tris-HCl pH 8, 10 mM EDTA pH 8 (GTE). The colonies are suspended with a sterile spreader and all eluates pooled to yield a cell suspension which is spun at 9800 Xg for 5 minutes. The pelleted cells are resuspended in 72 mL-GTE. Then 8 mL of GTE containing 40 mg of lysozyme/mL is added. The lysozyme digestion is incubated at room temperature for 20 minutes. Then 160 mL of alkaline-SDS (8 g of NaOH/L, 10 g of SDS/L) is added which yields a viscous lysate after gentle mixing. After incubation on ice for 20 minutes, 80 mL of 5M potassium acetate is added, mixed, and incubated an additional 20 minutes on ice. The preparation is then spun at 9800 Xg for 20 minutes, the supernatent collected and 200 mL of cold isopropanol added, mixed in and incubated on ice for 15 minutes, followed by centrifugation at 9800 Xg for 20 minutes. The nucleic acid pellet is dissolved in 20 mL TE supplemented with 1% sodium safcosine. Twenty-two grams of CsCl is added, and once dissolved, 2 mL of a solution of 10 mg ethidium bromide/mL is added. The CsCl-ethidium bromide mixture is loaded into appropriate tubes and centrifuged in a Beckman 70.1 Ti rotor at 55,000 rpm for 19 hours. The tubes are removed and plasmid band is recovered by syringe side puncture. Ethidium bromide is removed from the sample by extracting 4 times with equal volumes of butanol saturated with water. The aqueous solution is brought to 6 mL with TE; 1 mE 3M ammonium acetate is added and the plasmid DNA precipitated with 18 mL of ethanol. After chilling at −20° C. the DNA is pelleted by centrifugation at 3400 Xg for 30 minutes. A second precipitation is similarly performed, then the DNA is rinsed with ethanol, vacuum dired, dissolved in 1 mL TE and the DNA concentration is determined spectrophotometrically.

EXAMPLE 6

INTRODUCTION OF PLASMID LIBRARY INTO *STREPTOMYCES LIVIDANS* AND CONSTRUCTION OF A *S. LIVIDANS* RECOMBINANT CELL LIBRARY

The bifunctional plasmid library constructed in the previous step is transformed into *Streptomyces lividans* TK54 where phenotypic expression of Streptomyces genes is achieved. To this end protoplasts of *Streptomyces lividans* TK54 are prepared by essentially standard methods (Hopwood et al, 1985). Briefly, the cells from a 45-hour culture of *S. lividans* TK54, developed by inoculating 0.2 mL of a spore suspension into each of ten-50 mL aliquots of complete YEME medium (3 g of yeast extract/L, 5 g of peptone/L, 3 g of malt extract/L, 10 g of glucose/L, 340 g of sucrose/L, 5 g of glycine/L, 5 mM $MgCl_2$, 40 mg/L each L-histidine and L-leucine) are pelleted by centrifugation at 9800 Xg for 15 minutes. The cell pellet is washed twice with P medium and then suspended in 60 mL P+. Twenty mL of P$^+$ containing 14 mg of lysozyme/mL is added and the suspension incubated at 30° C. in a shaking water bath at 150 rpm for 90 minutes. Subsequently, 100 mL P$^+$ is added and the protoplast suspension is passed through sterile non-absorbent cotton. The filtrate is spun at 3800 Xg for 10 minutes, the protoplast pellet resuspended and washed with 100 mL P+, and after a second centrifugation resuspended in 120 mL P$^+$. The protoplast preparation is distributed to 1.8 mL cryotubes and frozen at −70° C. Transformation is conducted by distributing 0.3 mL of the TK54 protoplast preparation (containing ~1×10$^9$ protoplasts) to each of 4 centrifuge tubes containing 5 mL P$^+$. The protoplasts are pelleted by spinning at 3400 Xg for 10 minutes and then resuspended in the residual volume. Approximately 10 μg of cosmid library DNA is added to each, followed by the addition of 0.5 mL of 25% PEG1000 (1 g PEG1000 [Sigma] dissolved in 3 mL of a solution consisting of 25 g of sucrose/L, 2 mL 500X trace elements solution/L, 0.25 g of K$_2$SO$_4$/L, 100 mM CaCl$_2$, 50 mM TRIS-maleate pH 8). After mixing and incubating for 30 seconds, 5 mL P$^+$ is added. The protoplasts are then pelleted and resuspended in 1 mL P$^+$. One tenth ml volumes are then spread onto dried R$_2$YE agar (100 g of sucrose/L 0.25 g of K$_2$SO$_4$/L, 2 ml of 500X trace elements solution/L, 2g of L-proline IL, 20 g of D glucose/L, 5 g of yeast extract/L, 0.05 g of KH$_2$PO$_4$/L, 25 mM TES, 25 mM CaCl$_2$, 5 mM MgCl$_2$, 20 g of Bacto-agar/L) and incubated at 28° C. At 24 hours each plate is overlayed with 3 mL of soft R agar (formulated as above but without yeast extract, glucose, or KH$_2$PO$_4$ and containing 8g of Bacto-agon IL) containing 500 µg of thiostrepton/mL and then incubated an additional 12 days.

Approximately 9100 thiostrepton-resistant colonies are obtained. These are collected by scraping colonies from the agar plates into 3 tubes containing 25 mL each 20% glycerol. The colony suspensions are fragmented by sonicating for 90 seconds, pooled, then distributed to 1.8 mL cryotubes and frozen at −70° C. This frozen preparation constitutes the *S. lividans* recombinant cell library.

EXAMPLE 7

ISOLATION OF *S. LIVIDANS* LL535, A TETRACYCLINE-RESISTANT TRANSFORMANT FROM WHICH PLASMID LP$^2$127 IS DERIVED

The recombinant cell library of *S. lividans* is next subjected to a screen for tetracycline resistance. One-tenth mL portions of the fragmented *S. lividans* cell library are plated onto Bennetts agar supplemented with 100 µg of tetracycline/mL. After incubation at 28° C. for 5 days, two tetracycline-resistant colonies are detected. One of these, LL535 (initially designated LL529-2) is chosen for further analysis. The LL535 colony is streaked to fresh Bennetts agar containing 100 µg of tetracycline/mL. Growth is observed after 3 days incubation at 28° C. The growth obtained is scraped into 50 mL TSB supplemented with 10 g of glucose/L (TSBG) and 100 µg of tetracycline/mL and the suspension incubated at 30° C., 200 rpm. for 3 days The LL535 culture is briefly sonicated and a portion distributed to 1.8 mL cryotubes and stored at −70° C. The remaining volume is used to inoculate four 2 liter flasks containing 500 mL each modified YEME medium (as previously described but containing 16 g of glycine/L, 25 mMMOPS and without MgCl$_2$, L-histidine or L-leucine) containing 100 µg of tetracycline/ mL. The growth obtained after two days is then processed for isolation of plasmid DNA as previously described except that all volumes employed are four times that of the previous example. The final DNA precipitate is dissolved in 1 mL TE.

A 10 µL portion of the plasmid DNA isolated from *S. lividans* transformant LL535 is subjected to an in vitro packaging reaction and subsequently transduced to L coli X2819T using methods described hereinabove. An ampicillin-resistant transductant (designated LL537 is streaked to 20-10-5 agar containing 100 µg of ampicillin/mL and the growth obtained after a 1-day incubation at 30° C. is used to inoculate two 500 mL portions of 20-10-5 broth containing 100 µg of amplicillin/mL. After incubation at 30° C., 200 rpm overnight plasmid DNA is isolated again as previously described. The isolated plasmid is designated LP$^2$127; the estimated size of the plasmid is 43 kilobase pairs.

A restriction map is generated for LP$^2$127 by performing single and double digests with restriction endonucleases. The location of cleavage sites for BamKI, BclI, BglII, BsmI, BstBI, ClaI, EcoRI, MluI, NcoI, SacI, ScaI, SphI and StuI (New England Biolabs) are determined by digesting with each enzyme alone and in combination with enzymes that cut at known locations within the vector portion, such as EcoRI, ESaRV or HindIII. Restriction endonuclease digestions are performed by combining 1–2 µg of plasmid DNA 4 µl of a 10X solution of salts that are optimal for the restriction endonuclease being employed and approximately 5–40 units of enzyme in a total volume of 40 µl. The 10X salt solutions employed are as follows: for BamHI, EcoRV and SalI, 1.5M NaCl, 0.06M Tris PH8, 0.06M MgCl$_2$; for BglII and ScaI, 1.0M NaCL, 0.1M Tris pH7.4, 0.1M MgCl$_2$; for BclI, 0.75M KCl, 0.06M Trish pH7.4, O.1M MgCl$_2$; for BstBI, 0.6M NaCl, 0.06M Tris pH 7.4, 0.06M MgCl$_2$; for ClaI, 0.SM NaCl, 0.06M Tris pH8, 0.06M Tris pH7.4, 0.06M MgCl$_2$; for ClaI, 0.5M NaCl, 0.06M Tris pH8, 0.06M MgCl; for EcoRi, 0.5M Tris pH8, 0.1M MgCl$_2$; for MluI, 0.5M$^2$NaCl, 0.1M Tris pH7.4, 0.1M MgCl$_2$; for SacI, 0.1M Tris pH7.4, 0.1M MgCl$_2$; and for StuI, 1.0M NaCl, 0.1M Tris pHS, 0.1M Tris pH7.4, 0.1M MgCl$_2$; and for StuI, 1.0M NaCl, 0.IM Tris pH8, 0.1M MgCl$_2$. Double digests are performed with salt conditions compatible for both enzymes, as recommended by the manufacturer. All digestion reactions are conducted at 37° C. except for BclI which is performed at 50° C. and BsmI and BstBI which are performed at 65° C. The incubation time is 60–120 minutes. A 5 µl volume of tracking dye (50% glycerol, 0.1M EDTA pH8, 0.25% bromphenol blue) is added to stop the reaction and to facilitate the subsequent loading of agarose gels.

Figure 3:
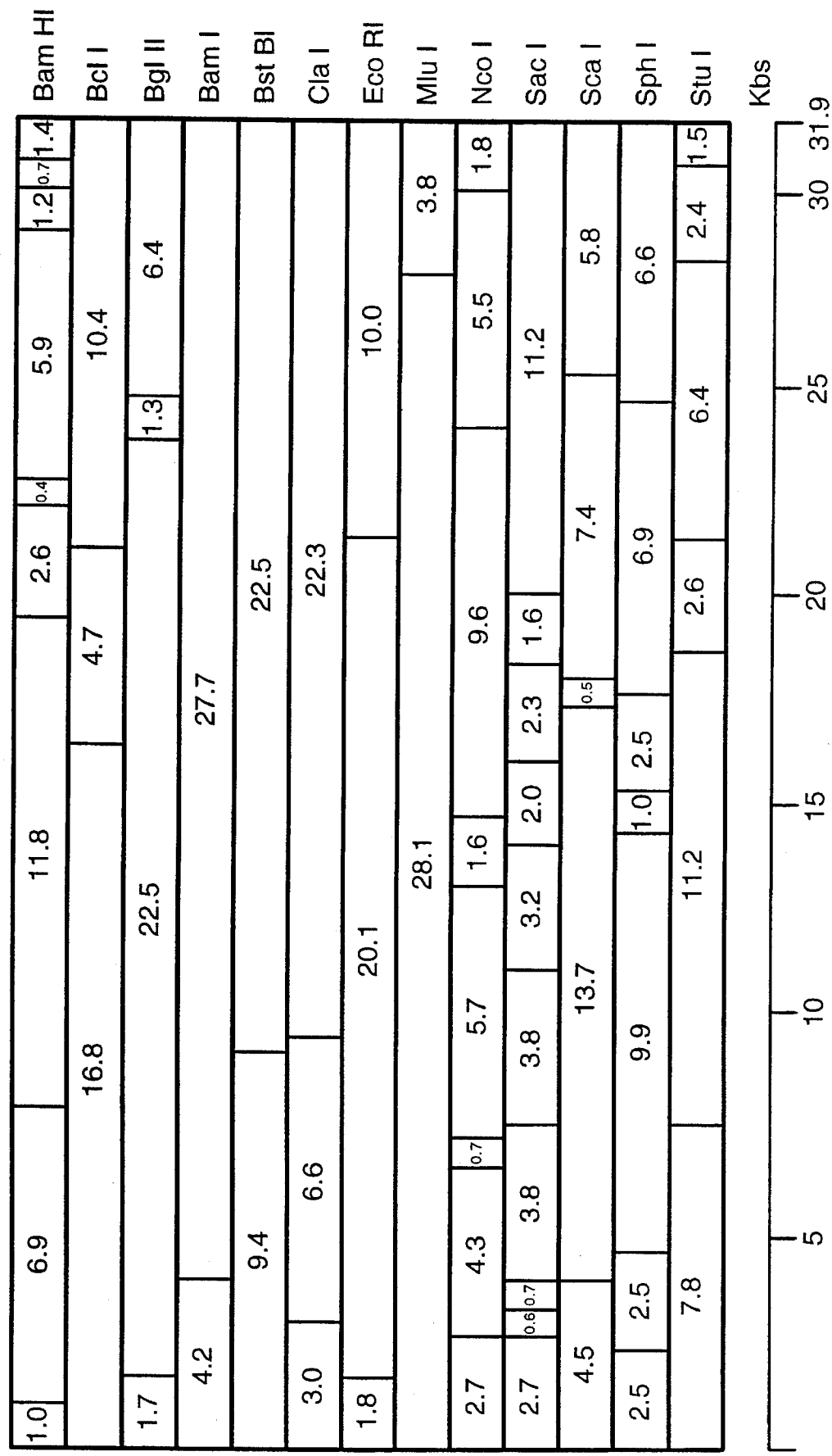
FIG. 3 shows the restriction endonuclease map for *S. aureofaciens* DNA which is cloned in LP$^2$127 and LP$^2$128. The 31.9 kb of DNA cloned in LP$^2$127 and LP$^2$128 is shown in linear form. The map is drawn so as to include the EcoRI sites derived from the vector as the start and finish positions at the left and right. The sizes of restriction fragments are presented in kilobase pairs and are accurate to within the normal resolution limits of agarose gel electrophoretic analyses (~500 bp).

Digestion results are visualized by electrophoresis through 0.8% agarose gels. The map is assembled by direct digestion of LP$^2$127 as well as by digestion of subcloned fragments. Mapping for BclI and ClaI sites is inhibited by host methylation and, therefore, aided by the use of LP$^2$258, which is obtained by in vitro packaging of LP$^2$127, transduction to *E. coli* GM119 (dam-dcm-) and plasmid isolation by previously described procedures. The physical structure of LP$^2$127 is shown in FIG. 2. A more detailed restriction endonuclease map for the 31.9 kb at *S. aureofaciene* DNA cloned in LP$^2$127 is shown in FIG. 3.

EXAMPLE 8

ISOLATION OF *S. LIVIDANS* LL529-TT2, THIOSTREPTON-RESISTANT, TETRACYCLINE-RESISTANT TRANSFORMANT FROM WHICH PLASMID LP$^2$128 IS DERIVED

The isolation of *Streptomyces lividans* LL529-TT2 is performed in a similar fashion to that described for LL535 except that the recombinant *S. lividans* cell library is plated onto Bennetts agar containing 50 µg of thiostrepton/mL and 100 µg of tetracycline/mL. After incubation at 28° C., for 11 days, two resistant colonies are observed. One of these, LL529-TT2 is streaked to Bennetts agar containing both antibiotics. After three days incubation at 28° C., the resulting growth is used to inoculate 50 mL TSB containing 10 µg of thiostrepton/mL and 100 µg of tetracycline/mL. After five days incubation at 28° C., 200 rpm, plasmid DNA is prepared by a minipreparation procedure, which is similar to previously described plasmid isolation procedures up to the isopropanol precipitation step. However, in this case the volumes employed are ~¼ of those previously noted. After isopropanol precipitation, the nucleic acid pellet is dissolved in 1 mL TE and extracted with an equal volume of chlorpane (500 g phenol and 0.5 g 8-hydroxyquinoline equilibrated in a buffer containing 100 mM NaCl, 1 mM EDTA pH5, 10 mM sodium acetate pH 6, plus 500 mL chloroform) by agitating and then spinning in a microlugs at full speed for 3 minutes. The aqueous phase is next re-extracted with chlorpane and then extracted with chloroform in a similar fashion. The final aqueous layer is collected and 100 µL 3M ammonium acetate and 1.8 mL ethanol are added to precipitate nucleic acids. After chilling to −20° C., the precipitation reaction is centrifuged at 8800 Xg for 30 minutes. The resulting pellet is dissolved in 300 µL 0.3M ammonium acetate, similarly precipitated with 1 mL ethanol and centrifuged. The resulting pellet is rinsed with ethanol, vacuum dried and dissolved in 1 mL TE.

The LL529-TT2 plasmid minipreparation is used to perform in vitro packaging as previously described. An ampicillin-resistant transductant (designated LL538) is chosen for plasmid preparation which is performed as outlined in the example for LL535. The resulting purified plasmid is designated $LP^2128$. The restriction band patterns obtained when $LP^2128$ is digested with 20 different restriction endonucleases is compared to that obtained for $LP^2127$ by analyzing the digestion products on the same electrophoresed agarose gel. The gel banding patterns obtained for $LP^2128$ are identical to those seen for $LP^2127$, indicating that the two plasmids are equivalent. Thus, FIGS. 2 and 3 describe the structure of $LP^2128$ as well as $LP^2127$.

EXAMPLE 9

PLASMID $LP^2127$ AND $LP^2128$ CONFER A PLASMID LINKED TETRACYCLINE RESISTANCE

To verify that the tetracycline resistances encountered are plasmid-borne, plasmids $LP^2127$ and $LP^2128$ are transformed into protoplasts of *Streptomyces lividans* and the resulting thiostrepton-resistant transformants are tested for tetracycline-resistance. The procedures for preparation and transformation of *S. lividans* protoplasts and the subsequent selection for thiostrepton-resistant transformants are performed as previously described. Ten µg of both $LP^2127$ and $LP^2128$ are transformed, as well as 5 µg of a tetracycline-sensitive control, $LP^2111$ (a vector consisting of pIB124, the SCP2* replication and stability regions and thiostrepton-resistance gene). One hundred and fifty transformants for each plasmid tested are sequentially picked to pairs of Bennetts' agar plates containing 100 µg of tetracycline/mL or 25 µg of thiostrepton/mL.

Growth of the stabs are scored after incubation at 28° C. for 5 days. All the thiostrepton-resistant transformants derived from $LP^2111$ prove to be tetracycline-sensitive, whereas 80% of thiostrepton-resistant transformants tested from either $LP^2127$ or $LP^2128$ are shown to be tetracycline-resistant.

EXAMPLE 10

PRODUCTION OF CHLORTETRACYCLINE AND TETRACYCLINE BY *STREPTOMYCES LIVIDANS* CONTAINING $LP^2127$ AND $LP^2128$

A series of experiments is performed to demonstrate that $LP^2127$ and $LP^2128$ direct the biosynthesis of chlortetracycline (CTC) and tetracycline (TC) in the heterologous host *Streptomyces lividans*. The original isolate LL535, as well as *S. lividans* transformed with $LP^2127$, produce CTC and TC on agar and in broth fermentation, whereas *S. lividans* containing a plasmid cloning vector without inserted DNA does not yield a tetracycline antibiotic. $LP^2128$ transformed into *S. lividans* directs the synthesis of an antibiotic with acitivity against *Escherichia coli* that can be biologically characterized as tetracycline. No such activity is produced by the *S. lividans* host.

Initially, *S. lividans* strain LL535, the thiostrepton-resistant isolate from which $LP^2127$ is isolated, is plated onto Bennetts agar (which contains 25 µg of thiostrepton/mL) at a cell dilution designed to give approximately 200 colonies per plate. *S. lividans* strain LL531 (which contains the previously described plasmid vector $LP^2111$) is similarly plated at a target density of ~400 colonies per plate.

After eight days incubation at 30° C., colonies of LL535 exhibit a yellow UV flourescence when illuminated with a 366 nm UV lamp. This is characteristic of tetracycline producing cultures and is not observed for LL531.

Plates of each then are tested for biological activity by overlaying the colonies with 5 mL soft 20-10-5 agar (8 g of Bacto agar/L) which has been seeded with 0.1 mL of an overnight growth of assay organism. The assay strains employed are *Bacillus subtilis* strain $T^1325$ obtained from the University of Leicester (Dr. Eric Clundliffe) T1325 (which contains a plasmid conferring thiostrepton-resistance), *Escherichia coli* MM294 and MM294 (ATCC 33625) containing pBR322 (which confers tetracycline and ampicillin resistance). The overnights are developed at 37° C. in 10 mL 20-10-5, which is supplemented with 25 µg of thiostrepton/mL for T1325 and 100 µg of ampicillin/mL for MM294/pBR322. Once overlayed and incubated at 37° C. overnight, the plates are examined for zones of inhibition in the lawns of overlay organism. Strain EL531 gives no zones with *E. coli* strains and only a few colonies give small localized zones with the gram-positive T1325. All of these latter colonies show red-pigment which is characteristic of expression of actinorhodin; *S. lividans* is known to express this normally cryptic pathway at observable frequency (Horinouchi et al, 1989). By comparison, strain LL535 shows production of an antibiotic that totally inhibits growth of the T1325 and MM294 in the overlay (In later experiments with fewer colonies per plate, small, discrete and very large zones of inhibition are seen around suitably separated individual colonies with these assay organisms). Colonies of LL535 overlayed in the present experiment with MM294/pBR322 show discrete zones around colonies. This reduced activity effect seen with MM294/pBR322 is taken to indicate a reduced sensitivity owing to the expression of tetracycline resistance resident on plasmid pBR322.

The antibiotic being elaborated on agar is characterized by extracting antibiotic from agar blocks of confluent plate cultures. Strains LL535 and LL531 are grown on Bennetts agar containing 25 µg of thiostrepton/mL; *S. aureofaciens* ATCC 13899, the source of the cloned DNA in $LP^2127$ and $LP^2128$, is plated on Bennetts agar without drug. After five days of growth at 30° C., 1" square agar blocks are cut out and macerated in 3 mL acid methanol (11.5 mL concentrated $H_2SO_4$ in 4 liters methanol). After vortexing for five minutes, the supernatant is filtered through an Acro®LC-25 membrane filter and subjected to HPLC analysis.

The HPLC analyses are carried out isocratically on a C18 reverse phase column with a mobile phase consisting of oxalate buffer at pH 2.9 containing 22% DMF=N.N-dimethylformamide. Flowrate is 1 mL/min and the eluate is monitored at 365 nm. Authentic tetracycline and chlortetracycline are used as standards.

The HPLC chromatograms show that LL535 and ATCC 13899 are producing substances with retention times indentical to TC and CTC. Extracts of LL531 do not show these peaks.

Thiostrepton-resistant transformants of *S. lividans* obtained with LP²127, LP²128 and LP²63 (a plasmid vector consisting of pIBI24 cloned into the SacI site of pIJ702) are similarly analyzed for production of antibiotic by overlay with assay organisms T1325 and MM294. The LP²127 and LP²128 transformants show production of antibiotic(s) active against both assay organisms whereas LP²63 transformants do not, thereby indicating that the ability to produce antibiotic is associated with the *S. aureofaciens* DNA present in LP²127 and LP²128.

Broth fermentations are also conducted as an additional confirmation that the antibiotics being produced by *S. lividans* bearing LP²127 are tetracycline and chlortetracycline. Fifty mL seed cultures of ATCC 13899, LL531, and LL873 (a LP²127 transformant of *S. lividans*) are developed using S medium (4 g of yeast extract/L, 4 g of peptone/L, 10 g of glucose/L, 0.5 g of $MgSO_4.7H_2O$/L) containing 5 μg of thiostrepton/mL; ATCC 13899 was grown without thiostrepton. After incubation at 30° C. for three days, 0.5 mL seed is transferred to 25-mL fermentations containing 10 μg of thiostrepton/mL (except no drug with ATCC 13899). After incubation at 28° C. for ten days, 0.5 mL samples of the final mashes are diluted into 4.5 mL acid methanol, processed as previously described and subjected to HPLC analysis. Strain LL531 yields no tetracycline compounds, whereas ATCC 13899, LL535 and LL873 yield 37, 56 and 6 μg/mL CTC respectively. A small amount of TC also is detected in the fermentation mashes of these three strains.

*E. coli* strains LL537 and LL538 are the *E. coli* transductants from which plasmids LP²127 and LP²128 are isolated and have been deposited, under the Budapest Treaty, in the American Type Cell Culture, 12301 Parklawn Drive, Rockville, Md. and have ATCC accession numbers as follows. *E. coli* X2818T containing LP²127 (LL537) has accession number ATCC 68357, and *E. coli* X2819T containing LP²128 (LL538) has accession number ATCC 68358. Both were filed on Jul. 10, 1990 and are available to the public when legally applicable.

BIBLIOGRAPHY

1. Baltz, R. H. and P. Matsushima. 1981. Protoplast fusion in Streptomyces: conditions for efficient genetic recombination and cell regeneration. J. Gen. Microbiol. 127:137–146.

2. Baltz, R. H. and E. T. Seno. 1988. Genetics of *Streptomyces fradiae* and tylosin biosynthesis. Ann. Rive. Microbiol. 42:547–574.

3. Bibb, M. J., J. M. Ward, and D. A. Hopwood. 1978. Transformation of plasmid DNA into Streptomyces protoplasts at high frequency. Nature (London) 274:398–400.

4. Binnie, C., M. Warren, and M. J. Butler. 1989. Cloning and heterologous. expression in *Streptomyces lividans* of *Streptomyces rimosus* genes involved in oxytetracycline biosynthesis. J. Baterial. 171:887–895.

5. Butler, M. J., E. J. Friend, I. S. Hunter, F. S. Kaczmarek, D. A. Sugden and M. Warren. 1989. Molecular cloning of resistance genes and architecture of a linked gene cluster involved in biosynthesis of oxytetracycline by *Streptomyces rimosus*. Mol. Gen. Genet. 215:231–238.

6. Chater, K. F. and C. J. Bruton. 1983. Mutational cloning in Streptomyces and the isolation of antibiotic production genes. Gene 26:67–78.

7. Chen, C. W., H. -F. Lin, C. L. Kuo. H. -L. Tsai and J. F. -Y. Tsai. 1988. Cloning and expression of a DNA sequence conferring cephamycin C production. Bio/Technology 6:1222–1224.

8. Cox, K. L. and R. H. Baltz. 1984. Restriction of bacteriophage plaque formation in Streptomyces spp. J. Bacteriol. 159:499–504.

9. Distler, J., K. Mansouri and W. Piepersberg. 1985. Streptomycin biosynthesis in *Streptomyces griseus* II. Adjacent genomic location of biosynethetic genes and one of two stretomycin resistance genes. FEMS Microbiol. Lett 30:151–154.

10. Duggat, B. M. 1948. Aureomycin: a product of the continuing search for new antibotics. Ann. N.Y. Acad. Sci. 51:171–181.

11. Feitelson, J. S. and D. A. Hopwood. 1983. Cloning of a Streptomyces gene for an O-methyltransferase involved in antibiotic biosynthesis. Mol. Gen. Genet. 190:394–398.

12. Fishman, S. E., K. Cox, J. L. Larson, P. A. Reynolds, E. T. Seno, W. -K Yeh, R. Van Frank and C. L. Hershberger. 1987. Cloning genes for the biosynthesis of a macrolide antibiotic. Proc. Natl. Acad. Sci. USA 84:8248–8252.

13. Gil, J. A. and D. A. Hopwood. 1983. Cloning and expression of a p-aminobenzoic, acid synthetase gene of the candicidin-producing *Streptomyces griseus*. Gene 25:119–132.

14. Goodman, J. J. 1985. Fermentation and mutational development of the tetracyclines. p.5–57. In: J. J. Hlavka and J. H. Boothe (eds), Handbook of Experimental Pharmacology, vol. 78, The Tetracyclines. Springer-Verlag, Berlin.

15. Hohn, B. and J. Collins. A small cosmid for efficient cloning of large DNA fragments. Gene 11:291–298.

16. Hopwood, D. A. and H. M. Wright. 1978. Bacterial protoplast fusion: recombination in fused protoplasts of *Streptomyces coelicolor*. Mol. Gen. Genet. 162:307–317.

17. Hopwood, D. A., 1967. Genetic analysis and genome structure in *Streptomyces coelicolor*. Bacteriol. Rev. 31:373–403.

18. Hopwood, D. A., M. J. Bibb, K. F. Chafer, T. Kieser, C. J. Bruton, H. M. Kisser, D. J. Lydiate, C. P. Smith, J. M. Ward and H. Schrempf. 1985. Genetic manipulation of Streptomyces—a laboratory manual. The John Innes Foundation. Norwich, England.

19. Horinouchi, S., F. Malpartida, D. A. Hopwood and T. Beppu. 1989. afsB stimulates transcription of the actinorhodin biosynthetic pathway in *Streptomyces coelicolor* A3 (2) and *Streptomyces lividans*. Mol. Gen. Genet. 215:355–357.

20. Jones, G. H. and D. A. Hopwood. 1984. Molecular cloning and expression of the phenoxazinone synthase gene from *Streptomyces antibioticus*. J. Biol. Chem. 259:14151–14157.

21. Katz, E., C. J. Thompson and D. A. Hopwood. 1983. Cloning and expression of the tyrosinase gene from *Streptomyces antibioticus* in *Streptomyces lividans*. J. Gen. Microbiol. 129:2703–2714.

22. Larson, J. L. and C. L. Hershberger. 1986. The minimal replicon of a streptomycete plasmid produces ultrahigh level of plasmid DNA. Plasmid 15:199–209.

23. Leskiw, B. K., Y. Aharonowitz, M. Mevarech. S. Wolfe, L. C. Vining. D. W. S. Westlake and S. E. Jensen. 1988. Cloning and nucleotide sequence determination of the isopenicillin N synthetase gene from *Streptomyces clavuligerus*. Gene 62:187–196.

24. Lydiate, D. J., F. Malpartida and D. A. Hopwood. 1985. The Streptomyces plasmid SCP2*: its functional analysis and development into useful cloning vectors. Gene 35:223–235.

25. Malpartida, F. and D. A. Hopwood. 1984. Molecular cloning of the whole biosynthetic pathway of a Streptomyces antibiotic and its expression in a heterologous host. Nature (London) 309: 462–464.

26. Maniatas, T., E. F. Fritsch and J. Sambrook. 1982. Molecular cloning: a laboratory manual. Cold Spring Harbor Laboratory, Cold Spring Harbor, N.Y.

27. McCormick, J. R. D. 1968. Point blocked mutants and biogenesis of tetracyclines. p. 163–173. In: G. Sermonti and M. Alecevic (eds), Genetics and Breeding of Streptomycetes. Yugoslav. Aced. Sci. and Arts, Zagreb.

28. Motamedi, H. and C. R. Hutchinson. 1987. Cloning and heterologous expression of a gene cluster for the biosynthesis of tetracenomycin C, the anthracycline antitumor antibiotic of *Streptomyces glaucescens*. Proc. Natl. Aced. Sci. USA 84:4445–4449.

29. Murakami, T., H. Anzai, S. Imai, A. Satoh, K. Nagaoka and C. J. Thompson. 1986. The bialaphos biosynthetic genes of *Streptomyces hygroscopicus:* molecular cloning and characterization of the gene cluster. Mol. Gen. Genet. 205:42–50.

30. Reynes, J. P., T. Calmels, D. Drocourt and G. Tiraby. 1988. Cloning, expression in *Escherichia coli* and nucleotide sequence of a tetracycline-resistance gene from *Streptomyces rimosus*. J. Gen. Microbiol. 134:585–598.

31. Sanger, F., A. R. Coulson, G. F. Hong, D. F. Hill and G. B. Peterson. 1982. Nucleotide sequence of bacteriophage lambda DNA. J. Mol. Biol. 162:729–773.

32. Stanzak, R., P. Matsushima, R. H. Baltz and R. N. Rao. 1986. Cloning and expression in *Streptomyces lividans* of clustered erythromycin biosynthesis genes from *Streptomyces erythreus*. Bio/Technology 4:229–232.

33. Stutzman-Engwall, K. J. and C. R. Hutchinson. 1989. Multigene families for anthracycline antibiotic production in *Streptomyces peucetius*. Proc. Natl. Acad. Sci. USA 86:3135–3139.

34. Sutcliffe, J. G. 1979. Complete nucleotide sequence of the *Escherichia coli* plasmid pBR322. Cold Spring Harbor Symp. Quant. Biol. 43:77–90.

35. Thompson, C. J., T. Kieser, J. M. Ward, and D. A. Hopwood. 1982. Physical analysis of antibiotic-resistance genes from Streptomyces and their use in vector construction. Gene 20:51–62.

36. van Pee, K. -H. 1988. Molecular cloning and high-level expression of a bromoperoxidase gene from *Streptomyces aureofaciens* Tu24. J. Bacteriol. 170:5890–5894.

37. Vara, J. A., D. Pulido, R. A. Lacalle and A. Jimenez. 1988. Two genes in *Streptomyces alboniger* puromycin biosynthesis pathway are closely linked. Gene 69:135–140.

38. Veselova, S. I. 1969. Combined effect of nitrous acid, ultraviolet light, streptomycin and chlortetracycline on *Actinomyces aureofaciens*. Antiobiotiki 14:698–702.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 30001 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GATCGGCCGA  CGGCTCCAGG  ACAGCCCGGG  CCGTCCCGGC  CCCGCGGCA  CGGCCCACCC      60

CGCAGCGACC  CCGGCCCGGC  CGCTCCACGG  CCCGCTCCCG  GCCCGCACAC  CTTCCGGGCC    120

CCACTCCGAA  GAATCGGTTC  TCTTGGGCCC  GTCACCGGGC  CGGGGCGTC   CACCGCACCG   180

CCCGCCGCGG  CCAGCCCGGA  TCGCTCCACT  CATCGGTCAC  TCGCGCCTGT  CGCCATCGGG   240

GGTCAACCGT  GTCAGTCGGC  AACAACCATC  CGTCGGTTCT  CGTCGTCGAG  GACAACGTCC   300

TGCTGCGCAC  GGGCCTGCAG  GCCCTGCTGT  CGGCCGAGCC  CGACCTCGTC  CTCCGCGCCG   360

CCGTCGGCGG  CGTGGACGAA  GCACTCGCCG  TCATGGCCGG  GCACCCCGTG  GACGTCGTGG   420

TGTACGGAGC  GGGCGAGTCG  GTGGCCGACA  CCGAGCGGGG  CCTCGAGCGC  CTGCTCGACC   480

GGGGCACCCG  GGTGGTCGTA  CTGAGCCGGC  GGGACCACCC  CGGCGAGATG  GAGACGTACC   540
```

-continued

| | | | | | |
|---|---|---|---|---|---|
| TCAGCAGCGG | TGTGCACGCC | TACCTGGCAG | AGGACGCGGC | CGGGGAGTGC | CTCGGCTCGG | 600 |
| TGATCCGGGG | CCTGACCTCG | GACCGGGAGC | GGGTCTACAT | CATGGCCTCG | CGCTCCGGCC | 660 |
| TCGACTGGAT | GGCCGGCCAG | CGCGGCAACC | GCCTGTCCGG | ACGCGAGCGG | GAGGTCATGG | 720 |
| GCCTGGTCGC | GAACGGGCTG | AGCAACTCGG | CCATCGCGGG | CCGGCTCTGC | ATCTCGCCCG | 780 |
| GCACCGTCAA | GCGCCATCTC | CGGAACGTGT | TCGTCAAGCT | CAACGCCGTC | TCCCGGATCG | 840 |
| ACGCCGTGAA | CAAGGCCCGG | GCCGCTTCCA | TGCTGGTCCC | GGCCGGCCGG | GCCTGAGCCC | 900 |
| CGCGGACCGG | TCCGGCGCGG | ATCCGTCCGC | GGTGGACCGG | TCCGGCGCGG | ACCCCTGCGG | 960 |
| GGACGACGGC | CCGGCAGGGA | GCGGAGCAGG | GCTCGGCCGG | GACGGGCCTC | AGGCCGAACG | 1020 |
| GGCCCGCAGG | CCCTGCTCCA | TCGCCCGCGC | GGCAAGCGCC | TGGAACTCCT | GCCGAGTGGG | 1080 |
| CGACGTGCCG | CTGAGCAGGT | CGTTGTGCAG | CTCCTGCAGC | GGTCGGGAGG | GGGCGATGCC | 1140 |
| GAGGTCCTCG | TCGAGCCGGC | GGTAGAGCAC | GCGGTAGACG | TGCAGGGCCT | CGCTCCGCCG | 1200 |
| CCCGGCGCGT | CCCAGGGCGA | GCATGAGCTG | CTCGTGGTAC | CACTCGTTCA | TCGGCTGGTG | 1260 |
| CAGGGTCAAC | AGTCTGAGTT | CGGGGATGAG | TTCCCGGTGG | CGCCCGAGCT | GCCGGTCGGC | 1320 |
| CAGGATGCGG | TGCTCCAGGG | CGCGCAGGCG | CATCTCCTCC | AGGACGGCGA | CGTGACCGGC | 1380 |
| GAGCGGAGCA | CCCCACCGGG | ATGTCCGCCA | GGCGGTGCCC | CGCCACAGGT | CCAGCGCCTG | 1440 |
| CCGCAGCCGC | TGGGCGGCCG | CCTCGGGGTG | GCCGGCGGCC | AGCAGCCGGT | CCCCCTCGTG | 1500 |
| GTGCAGCCGC | TCGAACTCCT | GGGCGTCCAG | CTCCTCCTCC | CCAGCAGCA | GCACGTAGCC | 1560 |
| GGGGGCCTTG | GTGAGGATGA | CCTCGCGGCC | CAGCGGACGG | CAGAGCTTGC | GCAGTTGGTA | 1620 |
| GATGTACGTC | TGCGCGGTGG | TGACCACCGT | GCGTGGCGGG | CTGCTGCCCC | AGATCTCCTC | 1680 |
| GATGATGAGG | CCGAGGTCCA | CGATCCGGTT | CGCGTTCATG | AGCAGGACCG | CCAGCGTCCA | 1740 |
| GCGGACCTTC | AGCGCGCTCG | GGGTACACGG | AATTCCCTTG | TCGAGGACTT | CCAGCGGACC | 1800 |
| CAGAATGTTG | AACTTCACCA | TGCCTCCGAT | GTCGCTCGGA | TTCCCTCGGC | CCCAGGTATA | 1860 |
| TCCGGGTCCG | CGGACGGGTC | TCAAGAGGAA | TCCGCACAAG | GTGGCAGGCG | CGCAATTCCA | 1920 |
| AGGTGGCACC | GACGCATTTC | CAGAGCGGTC | CGGCTCCCTG | TCCCGAGGGA | ACACCCCCG | 1980 |
| CCGACCGACC | CCCGCCGATC | GGCTGGCGGA | TCGACAAGTC | CTGTTAGGGT | GGGGGCGGTT | 2040 |
| GGCCCCATGG | GCCGGGCACC | AGTCACCTGA | TACCGCGAG | ACAGAGCCAC | GAGGAGAAGG | 2100 |
| ACGTGCCCCC | GAAAGATCCG | TGTTGCTCCG | GTAATCCGTA | CGAAGACCGC | AGAACTAGGG | 2160 |
| GACACACGTC | TTGACAACCG | TGAACATCGG | AATCCTGGCC | CATGTCGACG | CCGGTAAGAC | 2220 |
| CAGCCTGACC | GAGCGACTGC | TGCACACCGC | CGGCGTCATC | GACCGGGTCG | GCAGCGTCGA | 2280 |
| CCGCGGCGAC | ACCCAGACCG | ACTCGCACGA | ACTCGAGCGC | CAGCGCGGCA | TCACCATCCG | 2340 |
| GTCCGCGGTG | GTGTCCTTCA | CCGTGGGCGA | CGTCAAGGTC | AACCTCATCG | ACACCCCCGG | 2400 |
| CCACCCGGAC | TTCATCTCCG | AGGTGGAACG | GGCCCTCGGC | GTGCTCGACG | GCGTGGTGCT | 2460 |
| GGTCATCTCC | GCCGTGGAGG | GCGTACAGGC | CCAGACCCGG | CTGCTGATGC | GCACGCTGGT | 2520 |
| GAAACTGCGC | ATGCCGGTCA | TCCTCTTCGT | CAACAAGATC | GACAGGATGG | GCGCGCGCTA | 2580 |
| CCACGAGCTC | CTGGACGAGA | TCCGCTCCGA | GCTCACCCCG | GCCGTCGTCG | CCCTGACCCG | 2640 |
| GGTCGAAGGG | CCGGGCACCC | CCGGAGCACG | GGCGTTCGCC | CGGACCGTCG | GACCGACGA | 2700 |
| CCCCGACTTC | GCCGCCGAAC | TGGCCGACGT | CCTGGCCGAG | CACGGCGACG | ACTTCCTGGC | 2760 |
| CCGCTACCTC | GAGGACGAGA | CCTCCCTGAC | CGCGCAGGAC | TACAGCGCGG | AACTCGCCCG | 2820 |
| CCAGGCGGCC | CGGGCCCAGC | TCTACCCGGT | GCTCTTCGGC | TCGGCCGTGG | CCGGCGCCGG | 2880 |
| CATCGATGCC | CTGGTCGACG | GGATCACCAG | GCTGTTTCCG | GTCAATCACG | GCGGCTCCGG | 2940 |

| | | | | | | |
|---|---|---|---|---|---|---|
| GGGCACCCTC | CGCGGTACCG | TGTTCAAGAT | CGAGCGCGGG | TGGGCGGGCG | AGAAGGTCGC | 3000 |
| CTACGTCCGG | TTGCACGGGG | GCGAGCTCGG | GTCGCGGGAG | AAGGTGTCCG | TGTTCCGGCG | 3060 |
| CGACCAGCAC | GGAGCCGTCA | CCGAGATTCC | CGGCCGCACC | ACGGTGGTCG | AGGTGTTCGA | 3120 |
| CCGGGGCTCG | GCCGTCGTCG | AGTCGCGGGC | CCGGGCCGGG | GACATCGCCA | AGGTCTGGGG | 3180 |
| GCTCAAGGGC | ATCCGGATCG | GCGACCGGCT | CGGTTCGGCC | GAGGGGCTGG | ACGGGGAGCA | 3240 |
| CCTGTTCGCG | CCGCCGAGCC | TGGAGACCGT | GATCCGACCC | TCCCGGCCCA | GCGCGATGCC | 3300 |
| CGAACTGTAC | GACGCGCTGC | TGCAGTTGGC | CGACCAGCAC | CCGTTCATCA | ACGTCCGCAA | 3360 |
| GGACGACGAG | GAGCAGGAGA | TCGCCGTCTC | GCTCTACGGT | GAGGTGCAGA | AGGAGGTCAT | 3420 |
| CGCGGCCACG | CTCGCCGACG | AGTTCAAGCT | GGACGTGGCC | TTCGAGGGCA | CCCGGATCAT | 3480 |
| CTGTGTCGAG | CGCCCGATCG | GGTCGGCGA | GTCGGTGGAG | GAGATCGACT | ACCGGAGCAA | 3540 |
| GACCTTCTTC | TGGGCCACGA | TCGGCCTGCG | GGTGGAACCC | GGGAGCCGG | GATCAGGGGT | 3600 |
| CGTGTTCCGC | CGCTCGGTGG | AGCTCGGCTC | GCTGCCGCAC | GCATTCCACA | AGGCCGTCGA | 3660 |
| GGAGGCCGTG | CGGGCCACCC | TGCAGCAGGG | GCTGAACGGC | TGGGAGGTGC | TGGACATCCT | 3720 |
| GGTGACCCTC | ACCCGTTCCG | GGTTCGCCAG | CCCGGTGAGC | GCGGCGGGCG | ACTTCCGCAA | 3780 |
| GCTCACGCCG | CTCGTGCTGA | TGAACGCGCT | CAAGCAGGCG | GGCACGCAGG | TGTACGAACC | 3840 |
| GGTCAACCGC | TTCGAGCTGG | AGGTGCCGGG | TGAGAACGCC | AGCGCCGCCC | TGCTGAGCCT | 3900 |
| GGTGGAGTGC | GGCGCCACCC | CGGAGAGCAC | CCGGGGCCTG | GGCAGCAGCT | GCTGGTGGA | 3960 |
| GGGGACGATC | CCGGCCCGCA | CGGTGCAGGA | GTTCGAGCAG | CGGCTGCCGG | GCCTGAGCCA | 4020 |
| GGGCCAGGGC | GTGCTGGTCA | CCCGGTTCCA | CAGCTTCCAG | CCGGTGGTCG | GGCGGCGCC | 4080 |
| GAGGCGGCGG | CGGACCGACC | TCAACCCGGT | GGACCGCTCG | GAGTACATGC | TGCGGGCCTT | 4140 |
| CGGCGGGATC | TGACGGGACG | TCGCGAAAGT | GAGGGCCCGA | CCACCGTGAC | GGTGGTCGGG | 4200 |
| CCCTCAGCCG | TGGCGCACTC | CGTCCTCAGT | CGAGCAGTGC | CACCGCTCGC | GTCCAACCCG | 4260 |
| CCCCCGCCCC | GGCGATCTTG | ACCGGGAACG | CCTGCACGGT | GAACCCGGTC | GGCGCGGGCA | 4320 |
| GTGCGCCCAG | ATTGCTCAGA | CGCTCGATCT | GGCAGTACTC | CGCTGCCGC | CGCGAAATGC | 4380 |
| GCGGGCCACA | GCACGGAACG | GTCGCGGGTG | CGCTGGAACT | CGGCGAGCAT | GTGCGTGAAC | 4440 |
| GGAGCGTCCA | GCCCGAAGCG | TCCGTCCCGA | TGAGCCGCAC | GCCGAGGTCG | AGCAGAAGGT | 4500 |
| TCGTCGCCGC | CCCGTCCAGG | CCCGCGAACC | GGGTGAAGTA | CTCGGGAGTC | CCGGCGAGTC | 4560 |
| GTTCGGCACC | GGTGTGCAGC | AGCACGATCT | CCCCGGCGCT | CGGCCGGTGG | TCGATCTCGT | 4620 |
| CGAAGGCGCG | CCGCAGCCGG | TCCACGCCGA | CCGTCCCGAC | CCCGCAGTCG | GTGAGGTCCA | 4680 |
| GCCGGACGCC | CGGCCCGATG | AACCATTCCA | GCGGCAACTC | GTCGATGTGG | CGCGGCACTC | 4740 |
| CGTAGGCGGC | CCTGCTGCCG | TAGTGGGAGG | GTGCGTCGAC | GTGCGTGCCG | GTGTGGGTGG | 4800 |
| TCAGGGTCAG | GGTGTCCAGC | GAGAGCAGTT | CCCCGTCCGG | CAGGTCCGCG | ACGTCGAACT | 4860 |
| CGAGGCCGTG | GTCACGGAGC | ATGCCCTCGG | CCATGTGGCG | CGCGCCGTCG | GCCGGCGTCA | 4920 |
| GCACCTCGTG | GCGGATGCCG | TCCACCTCCC | AGGCGTTGGC | GTCGATCGTC | GAGGAGAGGT | 4980 |
| CAATGAGGCG | CATGCGCGGC | TCCTTCCGGC | AGCAGGGCGC | AGTCCGCAG | GACGTCGAGG | 5040 |
| CAGCGCTCCG | GCCCCCGATC | CCGCGCGGCG | AGGTGGCCGT | CCGGCCGGAT | CAGCAGGAAC | 5100 |
| TCCCCTGGTG | CCAGGCCGAG | TTCGCGGCGC | AGAATACCCC | CGGGGTCGGG | CAGCTCGCCC | 5160 |
| GGGGCTCCGG | GGTCGGCGAC | GGTACGGACG | GAGACGGCGG | AGCCGAACAG | CCGCTCCACC | 5220 |
| CGGGCGAGCG | CCTCCCGGTG | CCCGGTGCTC | CCGCCCTCGG | CCGGGGTGGC | GAGCAGGGTC | 5280 |
| CAGCGGGGGT | CGGCGAGTTC | GGCGCAGAGC | GCGGACCAGC | CGGGGTGCCC | GGCGGCCGTC | 5340 |

| | | | | | |
|---|---|---|---|---|---|
| CGGGCGTCGC | AGCCCACCCG | GTCCCCGGGG | GAGGGCCGCC | CGGCGCGCGA | GCCGGCCGGG | 5400 |
| CGGGTGAGCG | GGCTGTCCGG | GTAGCCGAGG | GCCAGTCCGC | AGAAGCCCCG | GATCATCCGG | 5460 |
| CCCTCGACCT | TGCGCCGCAG | CGGCGTGATC | CGGCGCAGCG | CCGCGGTGCC | CACGGTCAGC | 5520 |
| AGGGCCGGGG | CCAGCGCGGT | GCGCAGCGAC | ACCAGGGCGG | TGGCCGTGCG | GGTGGAGCGC | 5580 |
| AGCAGCACGG | CCCCGGTCGG | GACGCGCTCG | GCGTCGTAGC | TGTCCAGCAG | GCGGGCCCG | 5640 |
| GCGTGGCCGC | GGATCACGTC | GGCGAGCTTC | CAGGCGAGGT | TGTAGGCGTC | CTGGATACCG | 5700 |
| CTGTTCATGC | CCTGCCCGGA | GGCCGGGCTG | TGGACGTGGG | CGGCATCCCC | GGCGAGGAAG | 5760 |
| CAGCGGCCCT | CGCGCATCCG | GGTGATCTGG | CGTTGCTGGA | CGGTGAAGAC | GGAGAGCCAG | 5820 |
| GTCGGGGTGC | CGACCTGACG | GGGCGCCCGA | GCGCCGGCC | CGATCTTGTC | GGCCAGGCGG | 5880 |
| CGGCGGACCA | GCTCGCGGTC | CTCGGCGCCG | TCGGTGTCCA | CCGTGTCCAC | CACGCGCCAC | 5940 |
| TTGCCGGGCT | CGGGGAACGG | GACGAGCAGC | AGGGTGCCGG | GCTCGGTGTG | CAGCAGGTGG | 6000 |
| TTGCTGTCCG | GCGGGAGGTC | GGCGTCGAGG | GTGACGTCGG | CGTTGAGCCA | GACCTCGGTG | 6060 |
| GAGTCGCCGA | TCAGGCGCAT | CCCGAGCTGC | TTGCGCACGG | TGCTGCGGCC | GCCGTCGGCG | 6120 |
| CCGACCAGCC | AGGGCACCCG | GGTCTCCTCG | GTGCGCCCGT | CGGCGTGGCG | GAGGGTGACG | 6180 |
| AGCACGGAGT | CGGGCCCGGG | CTGCAGCGCG | GCGAGTTCGA | CGCCCCATTC | ACGGGGACG | 6240 |
| CCGAGTTCGG | CGGTGCGCTC | GCGCAGCACC | TGCTCGGTGA | CCACCTGGTC | GACCATCAGG | 6300 |
| CTGAACGGGT | AACGGGTCGG | CAGTGAGCGG | TAGTTGGTGT | CGAAGCGGAT | GAGGGTGCGG | 6360 |
| CCCCGGCGGT | GCATGGTGAA | GTGGGTGACC | CGCCGGCCGA | GCGGCAGCAG | CCGGTCGAGG | 6420 |
| GCGCCCATCT | GCTCGAGCAC | CTCCATGGTC | CGGGCGTGCA | CCGCCAGGGC | CCGGCTGCTG | 6480 |
| GTGGCCGGGG | CCGGGCGCGG | CGTCGACCAG | CCGGACGGGA | ACGCCCCGCG | CCTGGCGAGT | 6540 |
| TCGTGGGCCG | CGGTGAGGCC | GACCGGGCCG | GCCCCGCGA | TCAGGACGGC | CGGAGCGGGG | 6600 |
| TCAGCCACGG | CGTTCCTCGG | CGAAGCGCTT | GGCCAGGCCG | AGCGTGGCGC | GGCTGTTGCC | 6660 |
| GCCGGCGGCC | TCGCGGATGA | AGCGGCGGGC | GGTGGCGGCG | GTGGCGTCCG | GCCGAGGAC | 6720 |
| GGTGGGGACC | GCCTCGGGGT | TGAGGACGAC | GGCGTGCCAG | GAGGTGACCC | GCACTCCGCG | 6780 |
| GTCGGTCGAC | TCGACGGTCC | AACGGCCGGT | GTGGCGGCC | ATCATGGAGG | GGTGCGCAG | 6840 |
| CTGCTTGTAG | GCGATGCCGG | ACTCCGGGAA | GCAGATCCGG | ATGGACTCGG | TGGTGTGTTC | 6900 |
| GGAGCCGTCG | GCGGTGCGGG | TGTCCATGGA | CATGTGCTGG | ATGCCGCCGG | CCTCCTCGCG | 6960 |
| CAGGTCGAGG | CGGGCGACGT | GGGGCAGCCG | GGCGGGCCAG | GCGGCGGCGT | CCCGCAGGAA | 7020 |
| GTCGTAGACG | GCCTCCGGGG | CGGCGTCGAC | CAGCACCGAG | TCCTCGAACT | CGAACTCGAA | 7080 |
| CTCGGCGAGC | CGGTTCCAGC | GTTCGGCGAG | GTCCTTGATG | CCGGCGAGCT | CGCTGCGGCT | 7140 |
| GTTGCGGTCC | GTCGCCTCGC | TGATCCAGCG | CAGGCCCTGC | GGGTCGTCGT | CGAGCGCGCT | 7200 |
| GAACTCGTGG | GTGAGGGTGA | GGGTGGTGCC | GCCGGGGCGC | TCGGCGACCT | GCCACTCCCC | 7260 |
| CGCCATCGAG | GCGACCGGGG | CCGAGGAGGC | CTCCTGGCGG | AAGCGGATCC | GGCGCAGGTC | 7320 |
| GGCGTCCAGG | TCTCGGCGGG | ACGTCCAGTG | CTTGACCTCG | CCGTTGGCCC | GGGCCCAGAT | 7380 |
| CCGCAGGCGC | TCGGCGCCCG | GCCCAGCTC | CTCGCGCTCG | ACGTGGAGGG | TGGGGCGAA | 7440 |
| GCGCCGCGGC | CAGGCCAGGG | CGTCGGCGAT | GACGGTGTAG | ACGACCTCGG | CGGGGCGTC | 7500 |
| GACGTCGATC | GAGTGGGTGG | TGTGCTGGAT | GGTGCTCATG | GTGGGACCG | GCCCTTTCCG | 7560 |
| TCGGCGGGGT | GAAGTTCGGC | GGGGTGCGTG | GGTGCGGCT | CAGTAGATGC | CGAGGCCACC | 7620 |
| GCAGACGTTG | ATCGCCTGCG | CGGTGACCGA | CGCGGCGTCG | GGGGTGGTCA | GGTAGTCGAC | 7680 |
| CATGCCGGCG | ACCTCCTCCG | CGGTGGAGTA | GCGGCCGAGC | GGGATCTTCT | GCTCGAAGCG | 7740 |

-continued

```
CGAGAGCACG TCCTCCTCGG TGGTCGCCCA GGTCGCGGCG TACGCCTGGC GGACCCGCAC    7800
GGCCATCGGC GTCTCGACGT AGCCGGGGCA GACGGCGTTG ACCGTGGTGC CGGTGTGGGC    7860
GAGTTCCTTG GCCAGCGCCT TGGTGAAGCC GATGACGCCG GCCTTGGAGG CCGAGTAGGG    7920
GGCGCCCAGC GGGACACCCT GCTTGCCGCC GGTGGAGGCG ACGCTGATGA TCCGCCCGTG    7980
CCCGGCCGCC TCCATGCCGC CGGTGGTGAG GACCTCGCGG GTGACGCGGA AGACGCTGGT    8040
GAGGTTGGTG TCGATCACGT CCTGCCACAG CTCGTCGGTG AGGGTGGAGG TGACGCCACC    8100
GCCGTTGCGT CCGGCGTTGT TGACCAGCAC GCCGATCGCG CCGAAGCGGT CCACCGCCGC    8160
CCGGACGAGC CTGCTCACGT CCGGCGCGGA GCGGACGTCG GCCGCGAGGC CGTCCACCTC    8220
CAGGCCCTCG CCGCGCAGGC GGGCGACCGT CTCGGCGACG CCCTGCGCGG TGCGGGCGCA    8280
GATGAAGACG CTCAGCCCGC GCCGGGCCAG CCGCTCGGCG CTGGCCAGTC CGATGCCGCT    8340
GGTCGCCCCG GTCACCAGGG CGACGTCGCC GGTCGTCACG GTGCTCATCG CATCGATCTC    8400
CTGTCTCGCT CACGGATCGC GGGCCCGGCG GGCCCGCCGG TCGGGCCCG CCCCGCGCC    8460
CCGTCGGGAA CCCGGGGGA CAGGCCCCGG GCCGACCCTG CCCGGACGGC TTCGACTGCG    8520
GTTCGAGCGC GCCGCACACG CCGACCGCTC CAACGGGATT CGAAGCGCGG GTGGGAGCGT    8580
CGGCGCTGCC CAACCACCGA CGCAACGAGG AGGCCCGGAG CATGACCGGT TCGCTCTACG    8640
AGGAGGTCCA GCACTTCTAC GGGCGGCAGA TGCGCCACCT GGACGAGGGT GAGGTCACCG    8700
AGTGGGCCGC GACCTTCACC GAGGACGGCG TGTTCGCCGC CAACGCCCGC CGCACCCGC    8760
AGGAGGGGCG CGCGGCGATC GAGCAGGGCG CCCGGGAAGC CGCGCAGCGC CTGGCCGATG    8820
CCGGAATCCG GCACCGGCAC TGGCTGGGGA TGCTGGAGGT CGCCGCGCAG CCGGACGGCC    8880
TGGTGCTCGC CAAGACCTAC GCGCTGATCG TCGCGACGCC CAAGGGCGGG CCGGCCGCCG    8940
TGCACCTGAG CTGCAGCTGT GAGGACCAGC TGGTGCGCGT CGACGGCGAG TTGAAGGTCC    9000
GGCACCGCCG GGTGCACCGG GACGACCTGC CGCCTGAGA GGAGGCCACC GTGGACCTCC    9060
CACGGGACAG TACGACCTTC GGTCCGCCGC TGGACGTGGT GGCGGAGCTG ATCGGCGGGC    9120
CCCGGATCGA CGACCTCGTC CGTCGCGCGG CTGAGCTGAC GCCTCGTCAT GTAGCTCTGG    9180
TGCACGGTGA CCTGGTGCTC GACCACGCCG CGCTGGAGGC CCGGGTGAGC GACTGCGCCG    9240
AGGCGCTGCG CGCCGCGTTC GGCGGTCCCG GCACGGTCAT CGCGATCGCC GCCGAACTGA    9300
CCGTCGACTT CGCCGTCACC TTCCTGGGCA TCTCCCGCTC CGGGAACACC AGCGCCATGT    9360
TCAACCCGCT CGTCCCGGAC GACACCCTGG TGCACGTCCT GAACTCCTGC GGCGCCCGGG    9420
CGGCCGTGCT GTCGCCCCGG ATGCACCGCC GTGTCCTGGC CCTGCGGGAC CGGCTGCCGC    9480
TGCTGCGGCA ACTGGTGGTG ACCGCCGACG CGCTCGACGG CACGCCCGTC CTGGACGCCC    9540
TGGAGCGCAC CGCCGTCCCG GCCGGCGAGG TGGTGGAGAC CGCCTGCCTG CAGTTCACCA    9600
GCGGCACCAC CGGCGCGCCG AAGACCGTCC GGCTCAGCCA CCGCAACCTG CTGGTGAACG    9660
CGGCGCAGTC GGCGCACGCC CACCGGCTGA CGGCCGACGC CGTCTCGCTC AACAACCTGC    9720
CCTCCTTCCA CCTGATGCAC CTGAACACCG CGCTCGCGGT CGGCGCGACG CACGTGCTCT    9780
GCCCGGAGGA GGACCGCGCG GCGCTGGTGG GACTGGCCCG TACCTGGCGG GCCTCGCACC    9840
TGTACAGCCT GCCGGTGCGG TTGTCCCGGC TCGCCGGGGA CGAGCGGCTG CCCGGCTTCC    9900
GCATCCCCTC GCTACGGGCG GTGCTGTCCG GTGGATCGGC GCTGCCGCCC CGGACGACGA    9960
CCGCCCTGCA GGAGCACTTC GGGGTGCCGG TCGTCCAGGG CTACGGCCTC GCCGAGACGT   10020
CCCCGTCGAC GCACTTCGAC CTGCCCGAGG GGCCCACCCT CGGCTCCAGT GGGCCCCCGG   10080
TCGCCGGGAC GGCCTGCCGG ATCGTGGACG TGCGCACCGG CGCGGTGCTG CCGGTGGGCG   10140
```

| | | | | | |
|---|---|---|---|---|---|
| AGCGCGGTGA | GATCCAGGTC | CGGGGCCCGC | AGTTGATGCT | GGGCTACCTG | GGCGACGGGC | 10200 |
| CCACCGACGC | CGTCGACGCG | GACGGCTGGT | TCCGCACCGG | TGACGTCGGC | CGGATCGACG | 10260 |
| AGGCCGGCCG | CCTGTTCGTC | GTCGACCGGA | TCAAGGACGT | CTTCAAGTGC | GACAACTGGC | 10320 |
| TGGTGTCGCC | GACCGAGATC | GAGCGGGTGC | TGATGCGGCA | CCCGGCCGTC | GCCGACTGTG | 10380 |
| TGGTCTTCGA | CCAGCCCGAC | GAGCTGAGCG | GCGCCGTCGC | CGTCGGCCTC | GTCGTGCCGC | 10440 |
| GCGGCGAGGG | CGTCGACCCG | GCCGCCCTGG | CCGCGTTCGC | GAACGCCCGG | CTCCCCTACT | 10500 |
| ACGAGCACCT | GAAGCAGCTG | CGCCTGGTGG | AGGGCATCCC | GCGCTCCGCC | ACGGGCAAGG | 10560 |
| TCCAGCGGCG | CGAGCTCCGT | GACCGGCTGT | TCGGCTCCCT | CTGACCCGCA | CCACCCCACC | 10620 |
| CGTCCGACCC | ACCACAGGAG | GAACACCGTG | TACACCTTCA | TCAACCGTTT | CACCGTCACC | 10680 |
| GGGGACGTCG | CCGAGTTCGA | GACGCTCGTC | GGCGAGATCA | GCGAGTTCAT | GAGCGGCCGG | 10740 |
| CCCGGCTTCC | GCTCGCACCG | GCTGTACCGC | TGCGCCACGG | ACGCCTCGGT | GTACGTGGAG | 10800 |
| ACCGCCGAGT | GGGACGACGC | GGCCTCGCAC | CGGGCGGCGA | CCGGCTCGCC | GGAGTTCCGC | 10860 |
| GCCCGGGTCG | GCAAGGTGAT | GAGCCTGGCC | AAGGCCGAGC | CGGCCCCGTT | CGACCTGCTC | 10920 |
| GCGCAGCACG | GCGCCTGAGA | GGGGGAGCAC | CATGACGGAC | AACGGCGAGA | TCATTGCGCA | 10980 |
| GCCGGTGATC | CAGCTGCGCG | AGCTGGGGCT | GGCGGCGGCC | GGCGCCGCCG | CCGTGCGGGC | 11040 |
| CGCGGCCCGG | CTGGGCCTGG | CTGACGCCCT | GGGCGAGGAG | CCCGCCGGCG | CGGCCGAGCT | 11100 |
| GGCCCGGGCC | GTGAACGCGG | ACCCGGACAC | CCTGCAGCGG | CTGCTGCGCG | CCCTGGCCTG | 11160 |
| CTACGGCGTG | TTCGCCGAGC | AGCCGGACGG | TCGGTACGTG | CACACCGGCG | CCTCCCGGCT | 11220 |
| GCTGCGCGAG | GACACCCCGC | GCAGCCTGAA | GGACATGGTG | CTCTGGGGCA | CCGAGCCGTG | 11280 |
| GACCTGGGAG | CTGTGGGGCC | ACCTCGACGA | GGCGGTGCGC | ACCGGCAAGG | CCGTCTTCCC | 11340 |
| CGAGCTGCAC | GGCATGGACT | TCTTCGACCA | CCTGCACGCC | CACTCCCCCG | AGTCGGCGGC | 11400 |
| CGTGTTCGAC | CGGGCGATGA | CCCAGTCCAG | CCGGCTCTCC | GCGCTCGCGT | TGGCCGACCG | 11460 |
| GCTGGACCTC | GGCGGGGTCG | GCACGGTGGT | GGACATCGCC | GGTGGCCAGG | GCACGTGCT | 11520 |
| GGCCACCCTG | CTGGAGCGCA | ACCCCGGTCT | GCGCGGCACC | CTGCTGGACC | TGCCCGAGGT | 11580 |
| CGTCTCCGGG | GCCGACGCCC | GGCTGCGGCC | GGGCGGTGCG | CTGGCCGGGC | GCGCCACGCT | 11640 |
| GCTCGGCGGC | GACTGCCGGC | GGGAGATCCC | GGTGCAGGCC | GACGTCTACC | TGCTGAAGAA | 11700 |
| CATCCTGGAG | TGGACGACG | AGAGCACCGT | CCTGACGCTG | CGCAACGTCG | TCCGGGCGGC | 11760 |
| TGCTCCGGGC | AGCCGGGTGA | TCGTGGTCGA | GAACCTGGTG | GACGGCAGCC | CGAGCTGCG | 11820 |
| GTTCACCACG | GCGATGGACC | TCCTGCTGCT | GCTCAACGTC | GGCGGCCGCA | AGCACACCAG | 11880 |
| GGCCGGCCTG | GTCTCGCTGA | TCGAGGAGGC | GGGCCTGACC | CGGGCCGAGG | TCCGTCCGGT | 11940 |
| CAACTCCTAC | CTGCACCTGG | TGGAGAGCGT | GGTGCCCGAA | CGGGGCTGAC | CGCCCGCCC | 12000 |
| ACGGCCGCCG | CCCCCGGACC | CGTCCGGGGG | CGGCGGCCGT | GCTGGTCCGG | GGCGGCGGC | 12060 |
| CCTCGCACTG | TCCGGGGGCG | GCGGTGAGCC | CTCGGCACGG | CCGACGGGGC | TCGGGGGGC | 12120 |
| GGAACGGGAA | GGGGAGCGGG | GTCAGATGCC | CTCGGCGAGC | CGCTTCACCG | CCTGCTCGAC | 12180 |
| CCGCTCGTCG | GTCTCGGTGA | CGGCCACCCG | CACGTGCCGG | GCGGCCGCAG | CGCCGTAGAA | 12240 |
| CTCACCGGGC | GCCACCAGGA | TGCCGCGGTC | GGCCAGCGCA | CCGACGGTCG | TCCAGCACGG | 12300 |
| CTCGTCCCTG | GTCGCCCAGA | GGAACAGCGC | ACCGGCCGAG | TGCTCGATCC | GGAAGCCGGC | 12360 |
| GTCCACCAGC | GCCCCGCGCA | GCAGCTCGCG | CCGCCGGGCG | TAGCGCTGGC | GCTGGGCCGC | 12420 |
| CAGGTGCGCG | TCGTCACCGA | GCGCGGCGAC | CATGGCGGCC | TGCACCGGGG | CGGGGACCAT | 12480 |
| GTGGCCGGCG | TGCTTGCGCA | CCTCCAGCAG | CGTCGCGATG | ACGGCCGGGT | CGCCGGCGGC | 12540 |

```
GAAGCCCGCC CGGTAGCCGG CCAGGTTGAA GCGCTTGGAC AGCGAGTGCA CCGCCAGTAC    12600
GCCGTGGTGG TCGCCGCCGG TGACCTCGGC GTGGAGCACC GAGCGGGTCG AGCGCTCCCA    12660
CACGTGGTCC AGGTAGCACT CGTCGTTGAC CACCAGGGTG CCGCGCTCGC GCGCCCACTC    12720
GACGACCGCG CGCAGTTCGG CGGCGTCGAG CACCCGGCCC TCCGGGTTGG ACGGGGAGTT    12780
CAGCCACAGC AGGCGCGGCG CGGGGCCGTC GTAGCTCAGC GGGTCGTCCG TCCGGACGAA    12840
GGTGGCACCG GCCAGTCGAG CGCTCACCTC GTAGGTGGGG AAGGACAGTT GGGGGGCAAG    12900
GACGACGTCC CCCGGGCCCA GGCCCAGCAT GGTGGGCAGC CAGGCGATCA GCTCCTTGGT    12960
GCCGACCGCC GGGATCACGG CCTCCGGCTC GACGCTCACG CCCTCGCGGC GCAGCAGCCA    13020
GGCCGCGGCG GCGGCCCGCA GCGCGGGCGT GCCCTCGGTG GACGGGTAGC CCGGGGCGTC    13080
GGCCGCGGCG GCCAGGGCCG CGCGCACGGC CTCCGGGGTC GGGTCGACCG GGTCACCGAG    13140
CGCCAGGTTG ACCAACCCGT CGGGGTGGGC GGCCGCGCGC TGCGGTACG  GGAACAGAAC    13200
GTCCCAGGGG AACTTCGGCA GCCGCTCGAT CATGCCTGCG CCCCCGCCCC GACGTTGCGG    13260
GCCAGCGGCG GAGCCTGGCA GTCGGAGTCG ATGCCCAGG  AGACGATCCG CTCCGGCGTG    13320
ATCCGGATCA GCTCGTCGTC GACGTGCGGC AGGATCTCCT TGCCGCCGGT CGCCAGCGCG    13380
ACGGCGGTGC CCCGGATCTC GATCCCGCGG ACGACCCAGC GCTGCGCGTC CACGATGTCG    13440
TCCACCACCA GCGACACCCG CGGATGCCCC TGCACGTGGC GGTACTTGAG GCTGCGGGCC    13500
ATGCCGCGCC CGGTCACGTC GACGGTGCCG AGCTCGGCGT TGTAGTGGAA GCCCAGCGGG    13560
ACGACGTGCG GCTGTCCCCG GCCGTCCACG GTGGCCAGGC GGGCGAGCGG CTGCGAGGCC    13620
AGGTAGGCGG CCTCTTTCGC GGTGAATGGC ATGGCTGTCC TCGGTGTCTG CGGGTCAGGG    13680
TCGGCGCCCA CGCTAGGCAG CCTGCTTCGA GCGGCCTTGG TGCCGTTCGG CCTGCTCGCG    13740
TACCCGCGCT GGACTCCGGC TCGAAGTCCG GCTGACACGG TGAGGCCGTC GTACCGGACC    13800
GAGACGGGAG GTCGCGTTGG ACTGCGATGT GGTGGTGGCG GGAGCGGGGC CGACGGGCCT    13860
GATGCTCGCC TGCGAACTGG CCCTGGGCGG AGCCCGGGCG GTGGTGGTGG AACGGCGCCG    13920
CGAGCCGGAG AAGCACTCCA AGGCCATGGG CATGCAGGGC CGCACCGTGG AACTGCTCGA    13980
ACTGCGCGGG CTGCTCGACC GCTTCAAGGA GGGCGCGGGC GTGCTGCAGG GCGGCAACTT    14040
CGCCAGCCTG GGCGTGCCGA TGCGCTTCGA GGAGTTCGAC ACCCGCCACC CGTACGTGCT    14100
GCTGGTGCCC CAACTGCGCA CCGAGGAGCT GCTCGCCGAA CGGGCCCGCG AACTGGGCGT    14160
GCGGATCGTG CGCGGCTCGG GCGTCACCGG CTTCGCCCAG GACGCCGACG GGTCACCGT    14220
CGAGACGGAC ACGGGCCTGC TTCGGGCACG GTACCTGGTC GGCTGCGACG GCGGCGGCAG    14280
CACCGTCCGC AAGGCCGCCG GCATCGGCTT CACCGGACAG GACCCGCACA TGTACGCCCT    14340
CATCGGCGAC ATGCGCTTCA GCGGCGACCT GCCGCGCGGC GAGGGCCTCG GCCCAATGCG    14400
GCCGGTGGGC CTGGTCAACC CCGCCAAGCG GTCCTGGTTC GGCGCCTTCC AGCACCAGCC    14460
GGGCGTCTAC CGGGCCACCG TCGCCTGGTT CGACCGGCCC TTCGCCGACC GCCGCGCCCC    14520
GGTCACCGAG GAGGAGATGC GCGCCGCACT GGTCGAGCAC ACCGGCAGTG ACCACGGGAT    14580
GCACGACGTC ACCTGGCTGT CCCGCCTCAC CGACGTCTCC CGGCTGGCCG ACTCCTACCG    14640
GCTGGGCCGG GTGCTGCTGG CCGGCGACGC CGCGCACATC CACCTGCCGG CCGGCGGCCA    14700
GGGGCTCAAC CTGGGCTTCC AGGACGCCGT CAACCTCGGC TGGAAGCTGG CCGCCGTGGT    14760
CCGCGGCCAC GGCACCGAGG AGCTGCTGGA CAGCTACGGC CGCGAGCTGT CGCCCGATCG    14820
CCGACGGGTG GTGCGCAACA CCCGCACCCA GGCCGTCCTG ATCGACCCGG ACCGCGGTA    14880
CGAGGCACTG CGCCAGACCT TCCGCGACCT GATGGCGCTG CCCGACACCA ACCGCCACAT    14940
```

| | | | | | |
|---|---|---|---|---|---|
| CGCCGGCATG | CTCTCCGGCT | TCGACGTCGC | CTACGGCGGC | GGCGACCACC | CTCTGGTCGG | 15000 |
| CCGCCGGATG | CCGGACGCCG | AGCTGATCAC | CGCGGACGGG | CCGCGGAGGA | TCAGCGATTG | 15060 |
| CTTCGCCGGG | GCCCGCGGTC | TGCTGCTGCT | CCCCGAACAG | GGCCCGACCG | CCTCGCCGCT | 15120 |
| GGCCGCCTGG | GCGGACCGCG | TGGACACCCT | GACCGTCAAG | TCGGGCGGCC | CGGACCCGGA | 15180 |
| CACCGCCCAC | CTCGTCCGCC | CGGACGGCTA | CGTGGCCTGG | GCCGGCGAAC | CGGCCCGCAC | 15240 |
| CGAGGAACTG | CACCACGCCG | CGACCACCTG | GTTCGGCGCG | GCGGCCTGAT | CCCCCTCCCC | 15300 |
| CTGAGAAAGG | ACGCACGATG | ACCTCGTCCA | CCGACAGCGC | CGCCGCCCGC | GCGCGCCGGA | 15360 |
| TCGTCGCCCT | CAACACCGCC | TACTTCCAGG | CGAAGGCGCT | GCAGAGCGCG | GTCGAGCTCG | 15420 |
| GCCTCTTCGA | GCTGCTCGCC | GAGCGCTCCG | CCGGGCTCGA | CCAGATCCGC | GCCGAACTGG | 15480 |
| GCGTCCGGCA | CCGGCTGTTC | AAGGACTTCC | TGAACGCCCT | GGTCGGCCTC | GGCCTGCTGG | 15540 |
| ACGAGCAGGA | CGGCGGCTAC | CGGGCCTCCG | AGCTCGCCCG | GGAGTTCCTG | CTCCCCGGCC | 15600 |
| CCACGTACCT | CGGCGGCACC | GCCCGCCAGC | ACGCTCGGCT | GCACTACCAC | GCCTGGGCGC | 15660 |
| AGCTGACCGA | CGCGCTGCGC | GACGGCAAGG | CCAAGTCGGC | CGTGGCCGCG | CAGGGCCAGC | 15720 |
| TGGCCTACCC | CAAGCAGTAC | GAGGACCTGG | ACCGCGCCCG | GCAGATCATG | CTGCACATGG | 15780 |
| ACGCCCACAA | CGGTTTCACG | GCCGACGAGT | GGCGCGCGC | GATCGACTGG | AGCCGGTACA | 15840 |
| CCTCCTTCGT | GGACGTCGGC | GGCGGGCGCG | GCAACGTCGC | CTCCCGGATC | GTCACCGCCC | 15900 |
| ACCCGCACCT | GCGCGGCGGG | GTCTTCGACC | TGCCGGCGCT | GCGCCCGCTC | TTCGAGGAGC | 15960 |
| TGGTGGCCTC | GGCCGGAACC | GCCGACCGGG | TGGACTTCCA | CGGCGGTGAC | TTCTTCGCCA | 16020 |
| CCGACCTGCC | GGAGGCGGAC | GTGGTGATCT | TCGGTCACGC | CTGCCGGACT | GGGCCGGTCG | 16080 |
| GGGACCGCAG | GGAGCTGCTG | CGCCGCGCCC | ACAAGGCGGT | GCGCCCGGGC | GGCCTGGTGG | 16140 |
| TGCTGTACGA | CGCCATGATC | GACCCGGAGG | AGCGCGACCC | CGAGGTCCTG | CTGCAGCGGA | 16200 |
| TCAACCACAC | CATGATCCGG | GACGAGGCCG | GGGCCTACTC | GCTGCAGGAG | GCCCGCGCCT | 16260 |
| ACCTGGAGGA | GGCCGGCTTC | ACCGTCGACC | GGATCGCCGC | CTCCGACACC | ATCACCCGCG | 16320 |
| ACCACTTCGC | CATCGGCGTC | AAGTCGGTCT | GAAGGAAAAG | GAGTTCGACA | TGACCGACAC | 16380 |
| AACCGCGGAT | CAGACGCGGC | ACGGCGACCG | GCCGTACGAC | GTCGTCATCA | TCGGCAGCGG | 16440 |
| GCTGTCGGGC | ACCATGCTCG | GCTCGATCCT | CGCCAAGCAC | GGCTTCCGGA | TCATGCTGCT | 16500 |
| GGACGGTGCC | CACCACCCCC | GCTTCGCCGT | CGGCGAGTCC | ACCATCGGGC | AGACGCTGGT | 16560 |
| GGTGCTGCGG | CTGATCTCGG | ACCGGTACGG | GGTGCCGGAG | ATCGCCAACC | TGGCGAGCTT | 16620 |
| CCAGGACGTC | CTCGCCAACG | TCAGCAGTTC | GCACGGGCAG | AAGAGCAACT | TCGGCTTCAT | 16680 |
| GTTCCACCGG | GACGGCGAGG | AGCCGGACCC | GAACGAGACC | AGCCAGTTCC | GCATCCCCTC | 16740 |
| GATCGTCGGC | AACGCGGCCC | ACTTCTTCCG | CCAGGACACC | GACTCCTACA | TGTTCCACGC | 16800 |
| CGCGGTGCGC | TACGGCTGCG | ACGCCCGGCA | GTACTACCGG | GTGGAGAACA | TCGAGTTCGA | 16860 |
| CGACGGCGGG | GTGACCGTCT | CCGGCGCGGA | CGGCAGCACC | GTCCGGGCCC | GCTACCTGGT | 16920 |
| CGACGCCAGC | GGCTTCCGCT | CGCCGCTGGC | ACGGCAGTTG | GGGCTGCGGG | AGGAGCCGAG | 16980 |
| CCGGCTCAAG | CACCACGCCC | GCTCGATCTT | CACCCACATG | GTCGGAGTGG | ACGCGATCGA | 17040 |
| CGACCACGTG | GACACGCCGG | CCGAGCTTCG | CCCGCCGGTG | CCGTGGAACG | ACGGGACGAT | 17100 |
| GCACCACATC | TTCGAGCGCG | GCTGGATGTG | GATCATCCCG | TTCAACAACC | ACCCCGGGGC | 17160 |
| CACCAACCCG | CTGTGCAGCG | TCGGCATCCA | GCTCGACGAG | CGCCGCTACC | CGCCCGGCC | 17220 |
| GGACCTGACG | CCCGAGGAGG | AGTTCTGGT | CCACGTGGAC | CGCTTCCCGG | CGGTGCAGCG | 17280 |
| GCAGTTGAAG | GGCGCCCGCA | GCGTGCGCGA | GTGGGTGCGA | ACGGACCGCA | TGCAGTACTC | 17340 |

```
CTCGAGCCGG ACGGTCGGCG AGCGCTGGTG CCTGATGTCG CACGCGGCCG GCTTCATCGA    17400
CCCGCTCTTC TCCCGCGGCC TGTCCAACAC CTGCGAGATC ATCAACGCGC TGTCCTGGCG    17460
GCTGATGGCC GCGCTGCGCG AGGACGACTT CGCGGTCGAG CGCTTCGCCT ACGTGGAGGA    17520
ACTGGAGCAG GGCCTGCTGG ACTGGAACGA CAAGCTGGTC AACAACTCCT TCATCTCCTT    17580
CTCGCACTAC CCGCTGTGGA ACTCGGTCTT CCGGATCTGG GCCTCGGCCA GCGTGATCGG    17640
CGGCAAGCGC ATCCTCAACG CACTGACCAG GACCAAGGAG ACCGGCGACG ACAGCCACTG    17700
CCAGGCGCTG GACGACAACC CGTACCCGGG CCTGTGGTGT CCGCTGGACT TCTACAAGGA    17760
GGCCTTCGAC GAGCTCACCG AGCTGTGCGA GGCCGTGGAC GCCGGGGACA CCACGGCCGA    17820
GGAGGCCGCG CGGGTGCTGG AGCAGCGGGT CCGCGAGTCG GACTGGATGC TGCCGGCCCT    17880
GGGCTTCAAC GACCCCGACA CCCACCACAT CAACCCGACG GCGGACAAGA TGATCCGGAT    17940
CGCGGAGTGG GCCACCGGTC ACCACCGCCC GGAGATCCGT GAGCTGCTGG CCGCCAGCGC    18000
CGAGGAGGTC AGGGCGGCGA TGCGGGTCAA GCCGTAACAC GAGGGGCAAC GGGCAGCAGC    18060
GTCCGCGGGA CGGCTGCTCC CGGACGCGGG CCTCGCCGTT CGCCGCACGC GGGCGGGCTC    18120
AGCCCTCGGC CGCCAGGGTC AGGGCGGCCG TCCGCGGATC CTCCTCCACC GGCCAGCGGG    18180
CGTAGGAGCG GCGCCAGTAC ATCAGCGGGC TGGGCACCCT CGGGCCGGGG CCCGCCGGCC    18240
CACCACCGCG CCGATCACGA TGGTGTGGTC GCCCGCTGTC GAGGGCCGCG GCCGACCCGG    18300
CACTCGGCGT GCGCGACGAC GTCGGCCGAC AGTGACCGGC ACGCCACCGG CGCTGCCCGG    18360
CTCCCACCGG GACGTCCGG  AAGCGGTCGT CCACGGGCGC GGCGAAGCGC GGGGACGTGG    18420
ACTCCCCCTC CGCCGCGCAG CACGTTGACG GCGAACTCGC CGCGCTCCAG GAGGGCCTTC    18480
AGCACCCGGC TGTCGCGGTT GATGCAGACC CAGCAGCAGG GGCGGGGCCT TGGAGACGCT    18540
GCAGGCGGCC GAACAGGTCA ACCCGTACGG CTCCCCGTCC GGTCCCAGGG TCGTCACCAC    18600
GGTGACCCCG GTCGGCAGGG CGCCCATGAT CGACAGGAAG GTGTCGCCGT CCACCAGGCC    18660
GGGAGCCAGG TCCAGCGGCA GGGACAGGGG TTCGGGGGGC ATCGGTCCTC CACTCTCGGC    18720
GGGTCGGTGT CCCCATGCTC GCGGGCGCC  TTCGAGCCGG CGCCGGGCCG TCGTCGGGCC    18780
CTCCGCGCAC GCGAACGGGC GCGCAAACGG GCGCGCGAAC GGGCGCGCGC GAGGGCGCGC    18840
GGACGCGGCC GGAGCCGGAG CGGAAAAGCG CGTACCCCCG GCACGGGGGT GACCGGGGGT    18900
ACGCGCGGTT CAGGGGGTCG CGTGCGCGCG CTCACTCCTC GTCGCGCAGT TCCCGCAGCG    18960
GGAAGGTGAG CAGGAAGCCC ACCGCAAGGA TCAGGCCGCC GACCAGGAAC ATCGTGTCGA    19020
AGCCGAGGT  GAAGGCGTCG ACCGCCGAGG CGCTCAGGCC GCCGGTGGAG TCCGGGTCGG    19080
AGAGCGCACG GCGCACGGCC TCGTCCGGGT CGGCCCCGTC GAGCCTGCCG GCGGCGACGC    19140
CGAACAGCAC CGACATGAAG ACGGCGGCGC CGCTCGTGCC GCCGAGCTGG CGGAACAGCC    19200
CGGAGGCGGC GTTGGCCACG CCCAGCTCGG ACTTGGGCGC CGAGCTCTGG ATCGCCAGGG    19260
TGATGACGGT CTGGGAGAGC CCGATGCCGA AGCCCAGCCA GGCCGCGATC ACCACGATCA    19320
CCGCGAGCGG GGTGTCCGCG CCCGCGGCGG AGAGCGACAG CAGTGCTCCG CCATCGAGC    19380
CGAGGCCCAC GATCGCGGGC TTCTTGTAGC GGTTCCACTT CTTGATGATC TTGGCGCAGA    19440
TCGTCTGGGA GACGATCGCC CCGGTCATCA CCGGGATGAT CACCAGTCCG GCGACGGTGG    19500
CACTGCGCCC CTGCACCAGC TGCAGGAACA GCGGCAGGGT GGAGACCGTA CCGAAGATGC    19560
CGACGCCGAT GGTGAAGTTG ACGGCCGTGG TCATCGTGAT GCCACCGCGC GGAACAGCC    19620
GTAGCGGGAC CATCGCCTCC AGCCCGCGGG CCCGTTCGGC GAGCACGAAC AGCACCAGGC    19680
CGATCAGCGA GACGGCGAAC AGCGTCAGCG AACGCGCCGA TCCCCAGCCC CAGTCGAGGC    19740
```

```
CCTCCTCCGC CACGATCAGC AGCGGCACCA GGCAGAGCGC CAGGGTGAGC GCCCCCGGA    19800
AGTCGATCGG GTGGTCCACC CTGCGGTGCG GCAGGTTGAG CGCCTTGCGC ACGCTGAGCA   19860
GCGCCACGAG ACCGAGCGGC ACGTTGATCA GGAAGGCCCA GCGCCAGCCG GTCACCCCGA   19920
GGATCTCGCC GGCGCCCGCG AACAGGCCCC CGACGAGCGG GCCGAGCACA CTGGCCGCCA   19980
CCCAGGCCAT CATCAGGTAC GAGAAGTAGC GCCCGCGCTC GCGCACCGGG GCGAGGTCGG   20040
CGATGACGGC CGTCGGCAGC GACATCAGCC CGGCGCCGCC GAAGCCCTGG AGGACGCGGG   20100
CGATCGCCAG CGTCTCCATC GAGTTCGCCA TCGCGCAGGC CGCCGAGCCG ACGATGAAGA   20160
CCGCGATCGC CGCCAGATAG AGCGGCTTGC GGCCGTAGAT GTCGGACAGC TTGCCGTAGA   20220
ACGGCATCGC GATCGTGGAG CTGACCAGGT AGCCGGTGAT CACCCAGGCC TGGACGGTCT   20280
GGCCGTGCAG TTGGTCGCCG ATCGTACGCA GCGCGGTGGA GACGATCGTC TGGTCGAGTG   20340
CGGCGAGCAG CACGGCCAAC AGGAGCCCGG ACAGCGCGGT GATGATCTGG CGGTGAGTGA   20400
AGCCGGCGGG GCCGCCGGCC TCGTCCGCGA CGGCCTCGCC GGTCTGCGAG GTGGCGTTCG   20460
CCATTCCCAT TTCTCCCACC GAATTCGACA AGGTCTTGTC GAACTGAGCG TAGTGGGCTA   20520
CCGTGGCGGA ATGACAAGTT CTTGCCGAAA TCCCGGCCCG GACGAGGCTA GGCTGGCCGT   20580
GGAGAGCCTG CGATTAGGCT GCCCCCATGA CCGATCTCTC CCCCGCGGCC GAGACCTTGA   20640
GTGACATCAC CACCGAACTG TTCGCCGTCA ACGGAGCCCT GCTGCGCGCG GGCGACGCGC   20700
TGTCCGCCCG CTTCGGGCTC ACCTCCGCGC GCTGGCAGGT CCTCGGGCTG CTGGCCGAGG   20760
GGCCGCAGAG CGCCGCCCAC CTGGCGCGCG AGCGGGCTGC GCCGCCAGCC GTCCAGCAGA   20820
CCGTGGTGAA GCTGGTCGAG GAGGGCCTGG TCAGCACCTC CCCCAACCCG GCCGACCGGC   20880
GGGCCCCGTT GGTCTCGCTG ACCGCCAAGG GCACCGACGC CCTCGCCCGG ATCGAACCCG   20940
CCGAACGCCT GTGGATGGAG CACCTCGCGG GCGGCCTGGA TCCGGACGAC CTGACAGGCC   21000
ACGCTGCGGC TGCTGCGTGG CTTCGGGCGG TCCTGGCCGA GGGGCTGCCC CGACGGCGG    21060
TCGGCGGCGC GGACGCCGCC GACGTCACAG GTCCAGCGTG ACCTCGTACT CGGCGAGCCA   21120
GGAGTTGAGC CACAGCACCA GCTCCAGACT GCCCCGGTCG TAGGGCCGGC TCACCGCCCC   21180
GGTCGGACGG GCAGCCGCGG CCAGGGCCCG CTCGCGGTCC AGCAGCGGCA GCACCGGAGC   21240
GTCCGGATCG GCGAGCACCC CGGCCAGTTC GGCCCGCAGG GCGCCCTCGT AGCCCGGATC   21300
CTGGGTCGCC GGGTACGGGG TCTTCACCCG CTCGACCACC GAGCGCGGCA GCAGGTCGGC   21360
CACCGCCGCC CGCAGCAGGC TCTTCTCCCG GCCGTCGAAA CTCTTCATCT CCCAGGGCAC   21420
GTTGAAGACG TACTCCACGA GCCGGTGGTC GCAGAACGGC ACCCGCACCT CGAGGCCGAC   21480
CGCCATGCTC ATCCGGTCCT TGCGGTCGAG CAGGGTCTGC ACGAAGCGGG TCAGGTTCAG   21540
GTGACCGATC TCGCGCATCC GCCTCTCGGG CGCCGACTCA CCCGGCAGCA CCGGCACTTC   21600
GGCGAGCGCC TCGGCGTACC GGGCCGCCCG GTAGCCGTCC AGGTCGAGCT TGTCCAGCAG   21660
ACCCGCCTGG AACAGCGAGC TGCCGCCGAA GTAGCGCGCC GAACCCGGGG TGAGCCACGG   21720
GAAGGTGGCC GCCCGCAGGG CCAACGGGTT GCGGAACCAC CGGTAGCCGC CGAAGAGTTC   21780
GTCCGCGGCC TCGCCGGACA GCGCCACCGT GACGTTCTCC CGCACCGCGC GGAAGAACAG   21840
GTAGAGCGAG GGCCACATGT CGCCCCAGTA CGCGGGCGGC AGGTCGGTGG CGCGCAGCAC   21900
CGCGGAACGC ACCGCCGGGT CCGACAGGCC GGGGCTGTCC AGCAGCACCT CCAGGTGGTC   21960
CGCTCCGACG TGCCCCGCCA GCTCGCGCAC GTACGGCGCG TCCGCCTCCC GCCGGACGGC   22020
GTCGGAGGCG AAGGCGTCGG CGGCGCCCCG GAAGTCCACC GAGAAGGAGC GCACCGGCCC   22080
GCTGCGGGCG GCCAGCGCCG TCACGGCCGA CGAGTCCAGG CCGCCGGAGA GCAGCGTGCC   22140
```

| | | | | | | |
|---|---|---|---|---|---|---|
| CAGCGGGACG | TCCGAGACCA | GCTGACGGGT | GACGGTGTCG | GCGAGCAGGT | CACGGACGGT | 22200 |
| GCCGATGGTC | GTCGGCAGGT | CGTCGGTGTG | CTCGCGGGCC | TCCAGCCGCC | AGTACGTCTG | 22260 |
| CCGGCGCACC | CCGCCGCGCC | CCACCCGGAC | GAGCTGACCC | GGACGGACCT | CGACGAGCCC | 22320 |
| GGAGAAGACG | GCCGCCTCGG | GCGTCTTCAC | CATGTCCAGC | ACCTCGCACA | GCCCGTCCGG | 22380 |
| GCCGACCCGG | CGGGACAGGG | TCCGGTCCGC | CAGGACGGCC | TTGGGCTCCG | AGCCGAAGCG | 22440 |
| CACGCCGGCG | GCGGTCGGCC | AGTAGTAGAG | CGGCTTGACG | CCCATCCGGT | CGCGGACCAG | 22500 |
| CAGGAGTTCC | TCGCTGTGCT | CGTCCCAGAC | GGCGAAGGCG | AACATCCCGT | TGAGCCTCTC | 22560 |
| GACCAGCGCG | GCGCCCCACT | GGAGGTAGCC | GCGCAGGACG | ACCTCGGTAT | CGCAGGACGT | 22620 |
| CCTGAACCGG | TGGCCGTGCG | AGGTGAGTTC | GGCGCGCAGC | TCACGGAAGT | TGTAGATCTC | 22680 |
| GCCGCTGAAG | GTGATCGCCG | CGCCGCGGCC | CTCGTGTTCC | GCGGTCATCG | GCTGCCGGCC | 22740 |
| GTGCTCGGGG | TCGATCACCG | ACAGGCGCCG | GTGACCGAGC | CCGGCCGCGC | GGCCGAACCA | 22800 |
| GAGGCCCTCG | GCGTCCGGCC | CCCGGCAGGC | CATGGTGTCG | GTCATCGCCT | GGAGCAGGTC | 22860 |
| CCGGCGGTGT | TCGGCCGGGG | CGTCGTAGTC | GACCACCCCC | ACGATTCCGC | ACATGCTCAG | 22920 |
| CCGGCCGTGG | CGAGACCGAG | GTTGACCGCG | TCCAGGAGCA | TCCGCGGCGT | GGTGGCCTCC | 22980 |
| ACCACGGTCT | CGTCGGGCAG | GGTGATGCCG | CGCTCGCGCT | CGATGGTGTT | GAGGGTGTTG | 23040 |
| AACAGGGCGA | GCGAGTCGTA | GCCGAGGTCG | GCGAAGGGA | CGTCCAGGAT | GTCGTCGAGG | 23100 |
| GCGACGCCCT | CGTCGGCTCC | GGCAGCCTCC | TTCAGCGCGG | CGATCAGGTC | GTCAAGGGTG | 23160 |
| AACTCTGCCA | TGGCTGTTCC | TCACATCGGT | GGGTCGGTCT | GTCGAATCCG | GAAGGTCAGG | 23220 |
| CGGGCGGTCG | GCCGGCCCGG | TCAACTGGTC | AGTACGAGAG | CGCTGTTGAA | GCCGCCGTGG | 23280 |
| CCGCGGGCGA | GGACCAGCGC | GCTGCCCAGC | CGGGCCGGCC | TCGGCGGTCC | CAGCACCAGG | 23340 |
| TCGAGGTCCG | GGTGGGCCGG | CCGGCCGATG | TGCACGGACG | GCGGGATCAC | CCCGTCCCGC | 23400 |
| AGGGAGAGCA | GCGCGGCCGC | GACGTCCAGC | GGGGCGCCAC | CGGCCAGCAG | CCGGCCGGTC | 23460 |
| ATCGTCTTGG | GCGCCGTCAC | CGGCACCCCG | CGCGGGCCGA | ACACCGCGCC | CAGCACCTCG | 23520 |
| GCCTCGGCGC | GGTCCTGCTC | GGCCACACCG | CTGGCGTCGG | CGAAGACCAC | GTCGACGTCG | 23580 |
| GAGGGGCCGA | TCCCGGCGTC | GGCGAGCGCC | GTGTCGATCG | CCCGGCGCAG | CCCGGGCGGG | 23640 |
| CGCCCGGAGC | CGGGTCGGGG | GTCGAAGGTG | GCCGCGTAGC | CGGCGATCCG | CCCGTAGTGG | 23700 |
| CGGTGCTGCC | CGCGCTCGGC | GGCGCCGTCC | GGGTCTCCA | GCACGAGCAG | TGCGCCGCCC | 23760 |
| TCGCCCGGCA | CCCCGCCGGA | GGCGTCGGCG | TCGAAGGGCA | GGAAGGCCCG | CTGCGGGTCC | 23820 |
| CGCCGGGGGC | TGACCGTGCC | GCTGCGGCTG | AGGCAGAGCC | ACGACCAGGG | GCAGAGCGAG | 23880 |
| CCGTCCACCG | CGCCGGCCAG | CATCAGCGCG | GTGCCCTCGC | GCACGTGCCG | GCGGGCCTTG | 23940 |
| GCCAGCGCGT | CCAGGCCGCC | CGCCTGCTCG | GCCACCAGGG | CCGAACCGGG | GCCGCGCATG | 24000 |
| CCGTGCCGGA | TCGAGATCTG | CCCGGTGTTG | ACCGGGTAGA | ACCACGCGAA | GGACTGGTAG | 24060 |
| GCGCTGACGT | AGGCCGGGCC | CTTGCTCCAC | AGCGCCTGGA | GTTCCTTCTG | GCCGAACTCG | 24120 |
| AAGCCGCCGG | CCGAGGCGGC | CGTCACGACG | CCGGCGGAGA | AGTCCGGCAT | CGTCGTCGGG | 24180 |
| TCCGCCCCCG | CGTCGGCGAG | CGCCTCCTCG | GCCGCGACCA | GGGCCAGCCG | CGTCATGTGG | 24240 |
| TCGGTCTGCG | GCAGCAGTCG | GCCGGCAGG | TGTTCCTCCG | GCGTGAAGTT | CACCTCGCCG | 24300 |
| GCCACGTGCG | CCCGGTACCC | GGTGGAGTCG | AAGCGGGTCA | GCGGCCCGAG | ACCGGACCGG | 24360 |
| CCCGCCAGTG | TGGCGTCCCA | GTACTCCGCA | ACGCCCAGC | CGTTCGGTGC | CACCACGCCG | 24420 |
| ATCCCGGTCA | CCACGACGTC | GGTCATCCCC | GGCTCCACTC | CGGCTCGGCG | AGCACGATCG | 24480 |
| CGCTCTGGAA | GCCGCCGAAG | CCGCTCGCCA | CGCTGAGCAC | CGTGCGCACC | CGCTGTTCCC | 24540 |

-continued

| | | | | | |
|---|---|---|---|---|---|
| GCGCCACCAG | CGGCACGTAG | TCGAGGTCGC | ACTCGGGATC | GGGCACGTGC | AGGTTGGCCG | 24600 |
| TGGGCGGCAC | CACCGAGTGC | TCGATCGCCA | GCGCGCTGGC | GGCGAACTCC | AGGGCGCAGA | 24660 |
| CCGCGCCCAG | CGAGTGTCCG | ATCATCGACT | TGATCGAGCT | GACCGGCACC | CGTAGGCGT | 24720 |
| GGTCGCCCAG | GCTCTTCTTG | AACGCGGCGG | TCTCGTGCCG | GTCGTTCTGC | TTGGTCGCCG | 24780 |
| AGCCGTGCGC | GTTGACGTAG | CCGACGTCCT | CGGGGTTCAT | CCGGCTGCGG | TCGAGCGCGA | 24840 |
| CCCGGATAGC | CTCGGCCATC | TCGTTCCCGT | CGACCCGCAG | CCCGGTCATG | CTGTAGGAGT | 24900 |
| TGCAGCGCCC | GGCGTAGCCG | GTGACCTCGG | CGTAGATGTG | CGCGCCGCGC | CGGATCGCGT | 24960 |
| GCTCCCGCTC | CTCCAGCACG | AACATCGCCG | CGCCCTCGCC | GAGGGCGAAG | CCGTTGCGGG | 25020 |
| TCAGGTCGAA | GGGGCGCGAG | GCGCTCTCGG | GTTCGTCGTT | GCGCGGGGTG | GTCGCCTTGA | 25080 |
| TCGCGTCGAA | GCAGGCCACC | GTGATCGGGG | AGATCGCCGC | GTCCGAGGCG | CCGGCCAGCA | 25140 |
| TCACGTCGGC | CGCGTCGTCG | CGGATCAGGT | CGCAGGCGTG | CGCGATCACG | TCGATCCCCG | 25200 |
| AGGTGCATCC | GGTCGACACC | ACGCCCACCG | GACCCTCCGC | CTCGACCAGC | CAGGCCAGTT | 25260 |
| CGGTGGCCAT | CGAGGACGGG | ACGAAGTAGT | CGTAGAGGTA | CGGGACGCCG | TGCGCGTCGT | 25320 |
| CGACCAGCCG | CTTGCGGCCC | TCGTCGCTCA | CCACGGCGAA | CTCGCGGTCC | AGACTGATCG | 25380 |
| TCATCCCACA | GGCGGTGCCG | GCCATCACCC | CGGTGCGGAT | CGGGTCGTTG | ACGCCCGACA | 25440 |
| CCCCCGAGTC | GTCCAGCGCC | TCGCGCGCGG | CGACCACCGC | GAACTGCGCG | GTGCGGTCCC | 25500 |
| ATTGACGGAT | CTGACGCTGC | GTCAACCCCG | CGGCCTGCGG | GTCGAAGTCG | CACTCGGCGG | 25560 |
| CGACCCTGGA | CCGGAACGGC | GAGGGGTCGA | AGGTCGAGAT | CGTCCGGGTC | GCGGTCCGGC | 25620 |
| CGGCCGTCAG | CAGCTCCCAG | AACGCCTTGG | TGCCCACCTC | GCCCGGTGCC | ACCACGCCGA | 25680 |
| TCCCGGTGAC | CACCACGCGC | CGGCGGCCGT | CGTCAACTCC | CACCACTGCT | CCCCCTGTCG | 25740 |
| ATCTCCCCGT | GCGTGTCCGG | CGTCATGCCC | TGACCTCCTG | TCCGTGCGGC | CCGTCCGCGG | 25800 |
| GCTCGGGCGG | GCGGGGACTT | GAGCCGGATC | AGATCGTCCT | GGCAGGCGTT | CGCGGCGGCT | 25860 |
| TCGAGCCGCC | GTCCACGCGC | CTCCGGCCCC | CGCCTTCCCG | CCGCGGCGGG | AAGAGCCGCA | 25920 |
| CGCACGACGG | CGGCGGCGCC | GCACCCACGG | CGGCGGGAAG | ACGACGCGAA | CCGGCGTCGA | 25980 |
| AGGGCGCCCC | CTAGCGTCTG | GCCGCATGGA | CATCGACACC | GACATCTGCG | TGGTCGGCGG | 26040 |
| CGGCCCGGCC | GGGCTGACCC | TCGCCCTGCT | GCTGGTCCGC | TCGGGCCTGC | GCGTCACCGT | 26100 |
| GCTGGAACGC | AGCCGCTCCC | TGGACCGGGC | CTACCGCGGC | GAGATCCTCC | AACCCGGCGG | 26160 |
| CCAGGCCTTG | CTGGACGAGC | TGGGCGTGCT | CGGCCCGGCC | CGGGCGCACG | GCGCCGTCGA | 26220 |
| GCACGACCGC | TTCCTGCTCG | AGGAGCACGG | ACGCGTCCTC | ATCGACGGCG | ACTACCGGCG | 26280 |
| CCTGCCCGGG | CCGTACAACT | GCCTGCTGAG | CCTGCCCCAG | CGGCACCTGC | TGACCGAACT | 26340 |
| GCTCGCGGCC | TGCGAACGCC | ACGAAGGATT | CCGCCAGTTC | GCGGGCGCCA | AGGCCACCGC | 26400 |
| CCTGATCGAG | GAGGGCGGCT | TCGTCCGCGG | TGTGGTCGCG | GCGGCGCGG | GCGGCTCCCC | 26460 |
| CGACCGGGTG | GTGCGGGCCC | GCTGCGTCGT | CGCCGCGGAC | GGCCGCTTCT | CCAAGGTCCG | 26520 |
| CTCGCTCGCC | GGGATCGGCT | ACCGGCGCCA | GGAGCTGTTC | AGCCAGGACG | TCCTGTGGTT | 26580 |
| CCGGCTGAGC | GCACCGCCGC | GCACGGACAC | CCGACGCCCG | TGCGACGTCC | GGGTCTTCCG | 26640 |
| GGCCGGCGGC | AATCCGGTAC | TCAGCTACCG | CTCGGTGCCC | GAGGCGCTCC | AGCTCGGCTG | 26700 |
| GACCCTCCCG | CACGGCGGCT | TCCGCAAGCT | GGCCGACCGC | GGCATCGGCC | ACATCGTCGA | 26760 |
| CCAACTCGTC | GACGCCGCAC | CGGAGTACGC | CGACCTGATC | CGCCAGGAGA | TCACCGGCTT | 26820 |
| CGGCGACGTC | TCCCTGCTGG | ACGTCTTCTC | CGGCAGCGCC | GAGCACTGGG | TGCGCGACGG | 26880 |
| CCTGCTCCTG | ATCGGCGATG | CCGCCCACAC | CCACAGCCCG | ATCGGCGCCC | AGGGGATCAA | 26940 |

| | | | | | | |
|---|---|---|---|---|---|---|
| CCTGGCCGTC | CCGCCGCCGC | GTCGGGCCCA | CCCGGTGCTG | GTCGAGGCCG | TCCGCGGCGG | 27000 |
| CGACGCGGCG | CGGCCCGGCT | CGCCCCGTAC | GAACGGCAAC | GCCGCCCCCG | AAGTGGAACG | 27060 |
| GATCACCCGG | ATCCAGCAGG | TCCAGAGCCG | CATGATGCTC | TCCACCGGGC | GCATCTCCTC | 27120 |
| CACGGTGCGC | CCCCGGGCCG | CGGCGCTGGT | GTCCAGGACC | CCGCTGTACG | GGGCCGTGCT | 27180 |
| GCGCCGGATC | GCCTTCGGCA | CCGCGCCCGT | CCGGCTGCGC | GCCGATCTGC | TCGCCGGGGC | 27240 |
| GGGGCGGTGA | GCGGCGGGGC | AGCGATCGCC | GCCGGCGACT | CGGCGACGGC | GAGCGGGGTG | 27300 |
| CTCCTCGCCC | TCGCCGTCGT | CCTCGCCAGC | GCGTTCGTCT | GCGGCCGGCT | CGCCGCCCGG | 27360 |
| GTGCGCCAGC | CCGTCGTCAT | GGGGGAGATC | GTCGGCGGGG | TGGCCCTCGG | CCCCAGCCTG | 27420 |
| CTCGGGCTGC | TGCCGGGGCA | CCTGGACGCC | TCACTGTTCC | CGGCGGAGGT | CCAGTCCTAC | 27480 |
| CTGCGGGTGC | TGTCCCAACT | GGGCCTGGTG | CTCTTCATGT | TCACCGTCGG | CCTGCGCTTC | 27540 |
| GACGTCGGCC | ACCTGCGCGG | CGCCGGGCGC | CGGGTGACAG | CGGTGTCGCT | CAGCTCGGTG | 27600 |
| GCCCTGCCGT | TCGCGCTCGG | CGTGGGGCTC | GCGGTGCTGC | TCTACCCCTG | GTTCGACAAG | 27660 |
| GCCCAGTTGA | GCACCGACGG | GAGGCTCGGC | CCGGCCCTGT | TCCTGGGCGC | GGCGATGTCC | 27720 |
| ATCACGGCCT | TTCCCGTCCT | CGCCCGGATC | ATCGCCGAGC | GACGGATGCA | GCACGACCCG | 27780 |
| CTCGGCAGCC | TGTCATTGGC | CTGCGCGGCC | TTCCAGGACT | TCCTCGCCTG | GTGCGCGCTG | 27840 |
| GCGGTGGTGG | TGGCGGTGGT | GGAGGCCAAG | GGCCTCTGGT | CGCTGGGACG | GCTGGCGCTC | 27900 |
| GACACGGCGG | TGGTGGTCCT | GGTGCTGGTC | GGCGTCGTCC | GCCCGCTCCT | CTCCCGGCTG | 27960 |
| CTCGCCCCCG | GCCGGCGCCG | TCCCCTCCCC | CGGCCGTGGA | TCCACGCGGT | GCTCGTCACC | 28020 |
| GGCACCCTGG | TCACCGCCTG | GGTCACGGCC | GAGATCGGCC | TGGACGCGGT | GTTCGGGGCG | 28080 |
| TTCATGTTCG | GTGCGGCGGT | GCCCCGGGAC | CGGATCGAGG | CGATCGCGCC | CGACGTCCCG | 28140 |
| GAGCAGATCG | AGCGGGCGGG | TCTCCTGCTG | CTGCCGGCCT | TCTTCGCGGT | GACCGGCCTC | 28200 |
| GCCGTCGACC | TCACCGGCCT | CGGGCTGCGC | GGCCTGGCCG | TCGTGGCGGC | GGTGCTGGTG | 28260 |
| GCGGCCTGCG | CCGGCAAGTT | CGTCGGTGCG | GTCGCCGCCG | CCCGGGCCAC | CGGCTCGAGC | 28320 |
| CGGCGCGAGG | CGCGGGTGCT | CGGCATCCTG | CTCAACGCCC | GGGGCCTGAC | CGAGCTGGTC | 28380 |
| ATCCTCAACG | TGGGCCACCG | GCTCGGGGTG | ATCGACACCC | GGATGTTCAC | CGCCATGGTG | 28440 |
| GTGATGGCCC | TGGTCACGAC | GCTGATGACG | GGGCCGCTCC | TGGAGCGCCA | CACGGCGGGC | 28500 |
| TCCGCCGGAT | CCGCCACGCT | CCCGGACCCG | GCGCCCGAGG | CCGCACAGGC | CTCGCGGACA | 28560 |
| ACCTCCTGAT | GGCGGGCCGG | CCACGACCTC | CGGGGGGCGT | GCCCCTCACG | GCGGCTCCGT | 28620 |
| CCACCCGGAG | ACCCGGCGCA | GCCGCGACTC | AGCCGCCGCT | CGACCGGGCT | GAGCGGAACG | 28680 |
| TCGGGGCGCA | GCCGCTCCGG | GTGCCCCGAC | GGTGGCCCGC | CCCCGGCAGG | GCCGCCCGGC | 28740 |
| TCGCCGGGCG | CCGGACCGGC | CCGGGCTGCG | GCGGCGGGGC | CACGTAGCCG | GCCATCTGCC | 28800 |
| CCAGCGCCGC | CAGTCCGCGC | AGGAGCACGG | CCAGCAGATC | GAGGAGCCGT | TCGTTCGGTT | 28860 |
| CGCACATCCG | CCGAGCATGG | CGACCGGTCC | TGAAGCGCGG | TTCGAGCGGT | ACGGGAGGGG | 28920 |
| CGCCGGGCAC | GGCGGAGAGG | ACAGCCCGGC | ACCCTCGGAA | CCGCTGGAGC | ATGACCACGG | 28980 |
| CGCCGTCGGA | GCTGCGGGTG | CCCGTCACAC | TGACGATCCG | CCGCAGGAGG | GTCGGGCGTG | 29040 |
| TCCGAGGGTT | CCCGCCGGAC | CGGCCCCGAG | CCTCACTGGT | ACCGGTAGGT | GGCGGCCACC | 29100 |
| GCGAGGTGGT | CGCTGCCGTC | CGGGGCAGG | GTGCGGGAGT | CCACCGGCTT | CAGCCCGCCC | 29160 |
| TTGCTCATGA | TCTGGTCGAT | CCGCGCCATC | GGGAACGCCG | CGGGCCAGCT | GAAGCCGAAG | 29220 |
| CCGTCCCCGG | CCGCGCCCTG | GGCCGAGCGC | ATCTGCGAGG | TGACCGGTGC | CAGGCTGCGG | 29280 |
| TCGTTCATGG | TGCCGTTGAG | GTCGCCGAGC | AGCAGGACCT | TCTTCACCGG | CTCGGCCTGG | 29340 |

| | | | | | | |
|---|---|---|---|---|---|---|
| ATCGCGTCGC | CGAGCGCCTG | GGCGCTGACG | TCCCGCTGGT | GGGCGGTGAA | GCCGCTCTCG | 29400 |
| GCCTTGAGCC | GGACGGACGG | CAGGTGCGCG | ACGTACACCG | CGACCGGGCC | CTGGGGGGTG | 29460 |
| GTGACCCGGG | CCCGGAAGGC | CCTGGTCCAA | CCGATCTTCA | GGTCCACCGA | GGAGACCTCG | 29520 |
| CCGATCGGGT | ACTTCGACCA | GAGTCCGACC | GTCCCCTCCA | CCGTGTGGTG | CGGGTACGCC | 29580 |
| CCGGCGAGCC | CGGTCTCGTA | CGACCGCAGC | TGGTTGCCGG | CCAGTTCCTG | GAGCGCGACG | 29640 |
| ATCTGGGCGT | CCGAGGCGAC | CAGGCCGCGG | ATGGTGCCCG | GCACGTCGGT | GTTCCCGGCC | 29700 |
| TCGACGTTGT | GGGTGACCAC | CGTCCAGTCG | CCGGTGCCGC | CGCTCTTGTC | GGACACCAGC | 29760 |
| CCGCCGAACA | GGTTGGCCCA | CAGCACGGCG | GGCACCAGCA | GGGCGAGCAG | CGCGGTGGCG | 29820 |
| GAGCGGCGCA | GCAGCGCGGG | CACCAGCAGC | ACCGGGACGG | CCAGGCCGAC | CCAGGGCAGG | 29880 |
| AAGGTCTCCA | GCAGGCTGCC | GAGGTTGCCG | ACGCTGTTCG | GCATCTCGGC | GTGGAAGGCC | 29940 |
| AGCAGCACCG | CGGTGAGCAG | GGCCAGCAGG | GCGATCGGCC | AAGTGGGCGG | CCGTCGGGAT | 30000 |
| C | | | | | | 30001 |

What is claimed is:

1. A purified and isolated nucleic acid molecule encoding the proteins of the biosynthetic pathway for tetracycline, chlortetracycline, 6-demethylchlortetracycline, demethyltetracycline, 7-chloro-5a, 11a-dehydrotetracycline or 2-decarboxamido-2-acetyltetracycline, wherein said nucleic acid molecule is isolated from an antibiotic-producing wild-type or mutant Streptomyces.

2. The nucleic acid molecule according to claim 1, wherein the nucleic acid molecule is DNA.

3. The nucleic acid molecule according to claim 1, wherein the molecule has, as the coding portion of its nucleotide sequence, the sequence depicted in FIG. 4 and identified as SEQ I.D. NO. 1, and said sequence encodes the proteins of the entire biosynthetic pathway for chlortetracycline.

4. The nucleic acid molecule according to claim 1, wherein the nucleic acid molecule is isolated from an antibiotic-producing wild-type or mutant *Streptomyces aureofaciens*.

5. A DNA sequence which hybridizes under standard or stringent conditions to the sequence of the nucleic acid molecule of claim 1 and encodes the proteins of the biosynthetic pathway for tetracycline, chlortetracycline, 6-demethylchlortetracycline, 6-demethyltetracycline, 7-chloro-5a, 11a-dehydrotetracycline or 2-decarboxamido-2-acetyltetracycline.

6. A vector comprising the sequence of the nucleic acid molecule of claim 1.

7. A vector comprising the DNA sequence of claim 5.

8. The vector according to claim 6, wherein said vector is designated $LP^2127$ or $LP^2128$ and has a characteristic structure as shown in FIGS. 2 and 3.

9. A host cell stably transformed or transfected by a vector comprising the sequence of the nucleic acid molecule of claim 1.

10. The host cell according to claim 9, wherein said host is *Escherichia coli*, Actinomycetales, Bacillus or Cornebacteria.

11. The host cell according to claim 10, wherein said Actinomycetales is *Streptomyces lividans, Streptomyces griseofuscus, Streptomyces ambofaciens* or Thermoactinomyces.

12. The host cell according to claim 11, wherein said Actinomycetales is *Streptomyces lividans*.

13. A host cell stably transformed or transfected by a vector comprising the DNA sequence of claim 5.

* * * * *

UNITED STATES PATENT AND TRADEMARK OFFICE
CERTIFICATE OF CORRECTION

PATENT NO. : 5,589,385
DATED : December 31, 1996
INVENTOR(S) : Michael J. Ryan; Jason A. Lotvin; Nancy Strathy; Susan E. Fantini It is certified that error appears in the above-indentified patent and that said Letters Patent is hereby corrected as shown below:

Column 3, line 57, "plasmid A" should read --plasmid B--. Column 7, line 66, "pHS" should read --pH8--. Column 9, line 7, "6 Kb fragment" should read --6.1 Kb fragment--. Column 10, line 13, "safcosine" should read --sarcosine--; line 22, "mE" should read --mL--; and line 27, "dired" should read --dried--. Column 11, line 55, "L coli" should read --*E. coli*--; and line 67, "BamKI" should read --BamHI--. Column 12, line 5, "ESaRV" should read --EcoRV--; line 13, "Trish" should read --Tris--; line 15, "0.SM" should read --0.5M--; and line 20, "pHS" should read --pH8--. Column 13, line 1, "pHS" should read --pH8--; and line 3, "microlugs" should read --microfuge--. Column 14, line 22, "T$^1$325" should read --T1325--; and line 32, "EL531" should read --LL531--. Column 15, lines 34-35, "American Type Cell Culture, 12301 Parklawn Drive, Rockville, Md." should read --American Type Culture Collection, 10801 University Boulevard, Manassas, Va. 20110-2209 USA--; and line 50, "Rive." should read --Rev.--. Column 16, line 13, "Duggat" should read --Duggar--.

UNITED STATES PATENT AND TRADEMARK OFFICE
CERTIFICATE OF CORRECTION

PATENT NO. : 5,589,385
DATED : December 31, 1996
INVENTOR(S) : Michael J. Ryan; Jason A. Lotvin; Nancy Strathy; Susan E. Fantini It is certified that error appears in the above-indentified patent and that said Letters Patent is hereby corrected as shown below:

Claim 1, column 43, lines 26-27, "demethyltetracycline" should read --6-demethyltetracycline--.

Signed and Sealed this

Twenty-sixth Day of October, 1999

Attest:

Q. TODD DICKINSON

Attesting Officer

Acting Commissioner of Patents and Trademarks